US009489854B2

(12) United States Patent
Haruta et al.

(10) Patent No.: US 9,489,854 B2
(45) Date of Patent: Nov. 8, 2016

(54) COMPUTING TECHNOLOGIES FOR DIAGNOSIS AND THERAPY OF LANGUAGE-RELATED DISORDERS

(71) Applicants: Pau-San Haruta, Hyde Park, NY (US); Charisse Si-Fei Haruta, Hyde Park, NY (US); Kieran Bing-Fei Haruta, Hyde Park, NY (US)

(72) Inventors: Pau-San Haruta, Hyde Park, NY (US); Charisse Si-Fei Haruta, Hyde Park, NY (US); Kieran Bing-Fei Haruta, Hyde Park, NY (US)

( * ) Notice: Subject to any disclaimer, the term of this patent is extended or adjusted under 35 U.S.C. 154(b) by 124 days.

(21) Appl. No.: 14/527,379

(22) Filed: Oct. 29, 2014

(65) Prior Publication Data

US 2015/0118661 A1 Apr. 30, 2015

Related U.S. Application Data

(60) Provisional application No. 61/898,052, filed on Oct. 31, 2013.

(51) Int. Cl.
  *G09B 5/00* (2006.01)
  *G09B 19/04* (2006.01)
  *G09B 7/00* (2006.01)
  *G06F 19/00* (2011.01)
  *A61B 5/16* (2006.01)

(52) U.S. Cl.
  CPC . *G09B 5/00* (2013.01); *A61B 5/16* (2013.01); *G06F 19/345* (2013.01); *G09B 7/00* (2013.01); *G09B 19/04* (2013.01)

(58) Field of Classification Search
  CPC .......... G09B 7/00; G06F 19/345; A61B 5/16
  USPC ....................................................... 434/169
  See application file for complete search history.

(56) References Cited

U.S. PATENT DOCUMENTS

| 5,911,581 | A | 6/1999 | Reynolds et al. |
| 6,045,515 | A | 4/2000 | Lawton |
| 6,146,147 | A | 11/2000 | Wasowicz |
| 6,159,014 | A | 12/2000 | Jenkins et al. |
| 6,413,098 | B1 | 7/2002 | Tallal et al. |
| 6,699,188 | B2 * | 3/2004 | Wessel .......................... 600/300 |
| 2002/0001791 | A1 | 1/2002 | Wasowicz et al. |

(Continued)

FOREIGN PATENT DOCUMENTS

| WO | WO8201613 | 5/1982 |
| WO | WO9618184 | 6/1996 |

(Continued)

OTHER PUBLICATIONS

"Phonemic Awareness and Rapid Naming," internet URL http://web.archive.org/web/20130127144546/http://www.proedinc.com/customer/productView.aspx?id=5187 retrieved on Apr. 29, 2015; wayback machine date of Jan. 27, 2013.*

(Continued)

*Primary Examiner* — Michael Grant
(74) *Attorney, Agent, or Firm* — Dentons US LLP

(57) ABSTRACT

The present disclosure relates to computing technologies for diagnosis and therapy of language-related disorders. Such technologies enable computer-generated diagnosis and computer-generated therapy delivered over a network to at least one computing device. The diagnosis and therapy are customized for each patient through a comprehensive analysis of the patient's production and reception errors, as obtained from the patient over the network, together with a set of correct responses at each phase of evaluation and therapy.

20 Claims, 11 Drawing Sheets

(56) References Cited

U.S. PATENT DOCUMENTS

| | | | |
|---|---|---|---|
| 2004/0230430 A1 | 11/2004 | Gupta et al. | |
| 2007/0191727 A1 | 8/2007 | Fadem | |
| 2008/0241804 A1* | 10/2008 | Pennebaker | 434/178 |
| 2008/0243038 A1 | 10/2008 | Bennett | |
| 2010/0221688 A1* | 9/2010 | Reeves et al. | 434/236 |
| 2011/0015929 A1* | 1/2011 | Fantin | G06F 3/0219 704/260 |
| 2012/0270199 A1* | 10/2012 | Malik | 434/322 |
| 2013/0063494 A1 | 3/2013 | Kirschner et al. | |

FOREIGN PATENT DOCUMENTS

| | | |
|---|---|---|
| WO | WO0112058 | 2/2001 |
| WO | WO0160233 | 8/2001 |
| WO | WO0160243 | 8/2001 |
| WO | WO0171697 | 9/2001 |
| WO | WO03015014 | 2/2003 |
| WO | WO2006009771 | 1/2006 |
| WO | WO2012137131 | 10/2012 |

OTHER PUBLICATIONS

Academic Communication Associates, Assessment of Sound Awareness and Production (ASAP) kit and multicultural CD (#40441-IN), http://www.acadcom.com/ACAwebsite/prodView.asp?idProduct=628, 2014a, date accessed on internet Sep. 12, 2014, 3 pages.
Aleks, Assessment and Learning, K-12, http://www.aleks.com/, date accessed on internet Oct. 21, 2013, 1 page.
American Speech-Language-Hearing Association, Assessment and evaluation of speech-language disorders in schools, http://www.asha.org/SLP/Assessment-and-Evaluation-of-Speech-Language-Disorders-in-Schools/, 2014, date accessed on internet Sep. 17, 2014, 3 pages.
Anderson-Inman et al., Supported eText: Assistive technology through text transformations, Reading Research Quarterly, 2007, vol. 42, No. 1, pp. 153-160.
Andresen, Literacy, assistive technology and e-inclusion, Journal of Assistive Technologies, 2007, vol. 1, No. 1, pp. 10-14.
Archibald, Phonological acquisition and phonological theory, 1995, Lawrence Erlbaum, Hillsdale, NJ.
Arrow et al., The emergent literacy approach to effective teaching and intervention, Perspectives on Language and Literacy, 2011, vol. 37, No. 4, pp. 35-38.
Baddeley et al., The essential handbook of memory disorders for clinicians, 2004, John Wiley, Southern Gate, UK.
Barone et al., Best practices in early literacy instruction, 2013, Guilford Press, New York.
Berninger, Past, present, and future contributions of cognitive writing research to cognitive psychology, 2012, Psychology Press, New York.
Biemiller et al., A longitudinal study of the effects of the "Bridge" reading program for children at risk for reading failure, Learning DisabilityQuarterly, 1997, vol. 20, No. 2, pp. 83-92.
Bishop et al., Developmental Dyslexia and Specific Language Impairment: Same or different? Psychological Bulletin, 2004, vol. 130, No. 6, pp. 858-886.
Bishop et al., Language development in exceptional circumstances, 1993, Lawrence Erlbaum, Hove, UK.
Bloom et al., Discourse analysis and applications: Studies in adult clinical populations, 1994, Lawrence Erlbaum, Hillsdale, NJ.
Bradley et al., Response to intervention, Journal of Learning Disabilities, 2005, vol. 38, No. 6, pp. 485-486.
Brauth et al., Plasticity of development, Chapter 5 by Kuhl, Perception, cognition, and the ontogenetic and phylogenetic emergence of human speech, In, 1991, MIT Press, Cambridge, MA, pp. 73-102.
British Dyslexia Association, website, http://www.bdadyslexia.org.uk/, date accessed on internet Sep. 17, 2014, List of Software Available, 3 pages.
Cain et al., Children's comprehension problems in oral and written language: A cognitive perspective, 2007, The Guilford Press, New York.
Calfee et al., Acoustic-phonetic skills and reading—Kindergarten through twelfth grade, Journal of Educational Psychology, 1973, vol. 84, No. 3, pp. 283-298.
Caravolas et al., The influences of syllable structure and reading ability on the development of phoneme awareness: A longitudinal, cross-linguistic study, Scientific Studies of Reading, 2010, vol. 14, No. 5, pp. 464-484.
Carlson et al., Advances in cognition and educational practice, Introduction by Carver, Relating reading achievement to intelligence and memory capacity, 1998, JAI Press, Stamford, CT, pp. 143-173.
Castles et al., Varieties of developmental dyslexia, Cognition, 1993, vol. 47, No. 2, pp. 149-180.
Caverly et al., Techtalk: Assistive technology, Journal of Developmental Education, 2007, vol. 31, No. 1, pp. 38-39.
Center for Reading and Language Research at Tufts University, The Rave-O Curriculum, http://ase.tufts.edu/crlr/RAVE-O/index.htm, 2014, date accessed on internet Sep. 18, 2014, 1 page.
Center for the Study of Learning at Georgetown University Medical Center, Frequently asked questions about dyslexia, date accessed on internet Sep. 9, 2014, 1 page.
Chapman et al., Reading Recovery®: Does it work? Perspectives on Language and Literacy, 2011, vol. 37, No. 4, pp. 21-24.
Chastain, Native speaker evaluation of student composition errors,The Modern Language Journal, 1981, vol. 65, No. 3, pp. 288-294.
Chik et al., Contribution of discourse and morphosyntax skills to reading comprehension in Chinese dyslexic and typically developing children, Annals of Dyslexia, 2012, vol. 62, pp. 1-18.
Chun, A survey of research in second language acquisition, The Modern Language Journal, 1980, vol. 64, No. 3, pp. 287-296.
Claro Software, Claro Solutions Bundle, http://www.claroread.com/, 2014, date accessed on internet Sep. 18, 2014, 3 pages.
Cohen, Error correction and the training of language teachers, The Modern Language Journal, 1975, vol. 59, No. 8, pp. 414-422.
Coleman, Early intervention: A pathway for success, Perspectives on Language and Literacy, 2011, vol. 37, No. 3, p. 7.
Conway et al., Neural substrates related to auditory working memory comparisons in dyslexia: An fMRI study, Journal of the International Neuropsychological Society, 2008, vol. 14, pp. 629-639.
Copple et al., Developmentally appropriate practice in early childhood programs serving children from birth through age 8-Third edition, 2009, National Association for the Education of Young Children, Washington, DC, 8 pages.
Corder, Error analysis and interlanguage, 1982, Oxford University Press, Oxford.
Crews et al., Subtyping children's reading disabilities using a comprehensive neuropsychological measure, International Journal of Neuroscience, 2009, vol. 119, pp. 1615-1639.
Cronin, RAN and Double-Deficit Theory, Journal of Learning Disabilities, 2011, vol. 46, No. 2, pp. 182-190.
Cummings, Assistive and adaptive technology resources, Knowledge Quest, 2011, vol. 39, No. 3, pp. 70-73.
Daigle et al., Graphophonological processes in dyslexic readers of French: A longitudinal study of the explicitness effect of tasks, Annals of Dyslexia, 2012, vol. 62, pp. 82-99.
Davis Dyslexia Association International, website, http://dyslexia.com, date accessed on internet Sep. 17, 2014, 3 pages.
Dehn, Essentials of processing assessment, 2013, John Wiley & Sons, Somerset, NJ.
Denckla et al., Rapid 'Automatized' Naming (R.A.N.): Dyslexia differentiated from other learning disabilities, Neuropsychologia, 1976, vol. 14, pp. 471-479.
Divenyi et al., Dynamics of speech perception and production, 2006, IOS Press, Amsterdam, NLD.
Dodigovic, Artificial intelligence in second language learning: Raising error awareness, 2005, Multilingual Matters, Clevedon, UK.

(56) References Cited

OTHER PUBLICATIONS

Don Johnston_1, Dyslexia Products Page, http://donjohnston.com/dyslexia/#.VBosLhbupp9, date accessed on internet Sep. 17, 2014, 3 pages.
Don Johnston_2, Earobics, http://donjohnston.com/earobics-learning/#.VBxX3BawS3M, ndb, date accessed on internet Sep. 18, 2014, 2 pages.
Don Johnston_3, Simon S.I.O., http://donjohnston.com/simonsio/#.VBxdaRawS3M, ndc, date accessed on internet Sep. 18, 2014, 2 pages.
Don Johnston_4, Write:OutLoud, http://donjohnston.com/writeoutloud/#.VByplhawS3M, ndf, date accessed on internet Sep. 18, 2014, 2 pages.
Don Johnston_5, Co:Writer Universal, http://donjohnston.com/cowriter/#.VBytgBawS3M, ndg, date accessed on internet Sep. 18, 2014, 3 pages.
Don Johnston_6, WordMaker, http://donjohnston.com/wordmaker/#.VBxkVBawS3M, ndd, date accessed on internet Sep. 18, 2014, 2 pages.
Don Johnston_7, Read:OutLoud, http://donjohnston.com/readoutloud/#.VBynsxawS3M, nde, date accessed on internet Sep. 18, 2014, 2 pages.
Duncan et al., How do children read multisyllabic words? Some preliminary observations, Journal of Research in Reading, 2003, vol. 26, No. 2, pp. 101-120.
Edwards et al., Phonology: Applications in communicative disorders, 1983, College-Hill Press, San Diego, CA.
Elliott et al., The dyslexia debate, 2014, Cambridge University Press, New York.
Elman et al., Rethinking innateness: A connectionist perspective on development, Chapter 7 Where does knowledge come from?, 1999, MIT Press, Cambridge, MA, pp. 357-396.
Engstrom, Reading, writing, and assistive technology: An integrated developmental curriculum for college students, Journal of Adolescent and Adult Literacy, 2005, vol. 49, No. 1, pp. 30-39.
Erickson, Reading and assistive technology: Why the reader's profile matters, Perspectives on Language and Literacy, 2013, vol. 39, No. 4, pp. 11-14.
Ericsson et al., Long-term working memory, Psychological Review, 1995, vol. 102, No. 2, pp. 211-245.
Farrall, Reading assessment. Linking language, literacy, and cognition, 2012, John Wiley & Sons, Hoboken, NJ.
Fast ForWORD, Scientific Learning Products, http://www.scilearn.com/products/fast-forword, date accessed on internet Oct. 21, 2014, 5 pages.
Ferlito, Sortegories user guide, http://ferlito.weebly.com/uploads/1/4/8/5/14855104/sortegories_user_guide.pdf, nd, date accessed on internet Sep. 18, 2014, 5 pages.
Fletcher et al., Language acquisition: Studies in first language development, 1986, Cambridge University Press, Cambridge, MA.
Fletcher et al., Learning disabilities: From identification to intervention, 2006, The Guilford Press, New York.
Frawley, Linguistic semantics, 1992, Lawrence Erlbaum, Hillsdale, NJ.
Freedman et al., Learning to write: First language/second language, Chapter 2 by Bereiter et al., Does learning to write have to be so difficult? 1983, Longman, London, pp. 20-33.
Fulmer, The Slingerland tests: Reliability and Validity, Journal of Learning Disabilities, 1983, vol. 16, No. 10, pp. 591-595.
Gaab et al., Neural correlates of rapid auditory processing are disrupted in children with developmental dyslexia and ameliorated with training. An fMRI study, Restorative Neurology and Neuroscience, 2007, vol. 25, pp. 295-310.
Garton, Social interaction and the development of language and cognition, 1992, Lawrence Erlbaum, Hove, UK.
Gathercole et al., Developmental impairments of working memory: Profiles and interventions, Perspectives on Language and Literacy, 2014, vol. 40, No. 2, pp. 36-39.

Geiser et al., Auditory temporal structure processing in dyslexia: processing of prosodic phrase boundaries is not impaired in children with dyslexia, Annals of Dyslexia, vol. 64, pp. 77-90.
Ghotit, Dyslexia writing and reading assistant, http://www.ghotit.com/, 2012, date accessed on internet Sep. 18, 2014, 2 pages.
Gillingham et al., The Gillingham manual: Remedial training for students with specific disability in reading, spelling, and penmanship, 1997, Educators Publishing Service, Cambridge, MA.
Gillis, Promoting success: Early indicators of learning disabilities in preschool children, Perspectives on Language and Literacy, 2011, vol. 37, No. 3, pp. 29-31.
Ginger Software, Home Page, http://www.gingersoftware.com/, 2014, date accessed on internet Sep. 18, 2014, 1 page.
Givón, Functionalism and grammar, 1995, John Benjamins, Amsterdam, NLD.
Gomez et al., Central auditory processing ability in children with ADHD with and without learning disabilities, Journal of Learning Disabilities, 1999, vol. 32, No. 2, pp. 150-158.
Gordon-Pershey, Executive Functioning and Language: A Complementary Relationship That Supports Learning, Perspectives on Language and Literacy, 2014, vol. 40, No. 2, pp. 23-26.
Goswami, Phonology, reading development, and dyslexia: A cross-linguistic perspective, Annals of Dyslexia, 2002, vol. 52, No. 1, pp. 141-163.
Grammarcheck, website, http://www.grammarcheck.net/, 2014, date accessed on internet Sep. 18, 2014, 2 pages.
Griffiths et al., Auditory word identification and phonological skills in dyslexic and average readers, Applied Psycholinguistics, 2001, vol. 22, pp. 419-439.
Guan et al., Are poor Chinese text comprehenders also poor in written composition? Annals of Dyslexia, 2013, vol. 63, pp. 217-238.
Haaf et al., Computer-based language assessment software: The effects of presentation and response format, Language, Speech & Hearing Services in Schools, 1999, vol. 30, No. 1, pp. 68-74.
Habib, The neurological basis of developmental dyslexia: An overview and working hypothesis, Brain, 2000, vol. 123, pp. 2373-2399.
Hagan-Burke et al., The convergent validity of the Dynamic Indicators of Basic Early Literacy Skills and the Test of Word Reading Efficiency for the beginning of First Grade, Assessment for Effective Intervention, 2006, vol. 31, No. 1, pp. 1-15.
Haight, Test review: Wagner, R. K., Torgesen, J. K., & Rashotte, C. A. (1999). Comprehensive Test of Phonological Processing (CTOPP). Austin, TX: PRO-ED, Assessment for Effective Intervention, 2006, vol. 31, pp. 81-83.
Hairston et al., Altered temporal profile of visual-auditory multisensory interactions in dyslexia, Experimental Brain Research, 2005, vol. 166, pp. 474-480.
Halle et al., Linguistic theory and psychological reality, Chapter 8 by Carey, The child as word learner, 1983, MIT Press, Cambridge, MA, pp. 264-302.
Haruta et al., Struggling readers gain segmentation skill through responsive intervention, The Journal of Special Education, under review, 25 pages.
Haruta, What reading teachers don't see: Problems and progress in a student with dyslexia, The Reading Teacher, under review, 28 pages.
Hasbrouck, Diagnosis of auditory perceptual disorders in previously undiagnosed adults, Journal of Learning Disabilities, 2001, vol. 16, No. 4, pp. 206-208.
Heath et al., Auditory temporal processing in disabled readers with and without oral language delay, Journal of Child Psychology and Psychiatry, 1999, vol. 40, No. 04, pp. 637-647.
Heller et al., International handbook of giftedness and talent, Chapter 9 by Yewchuk et al., Inclusive education for gifted students with disabilities, 2000, Elsevier, Amsterdam, pp. 659-670.
Hendrickson, Error correction in foreign language teaching: Recent theory, research, and practice, The Modern Language Journal, 1978, vol. 62, No. 8, pp. 387-398.
Hinshaw et al., The ADHD explosion: Myths, medication, money, and today's push for performance, 2014, Oxford University Press, Oxford.

(56) References Cited

OTHER PUBLICATIONS

Hoh, Error analysis in the spoken English of Malaysian Chinese university students: A conversational approach, 1984, B.A. thesis, Universiti Sains Malaysia, Malaysia.

Hoh, Symbiotic phonological development in a Cantonese-English-speaking child, Meeting Handbook of the Linguistic Society of America, Jan. 8-11, 1998, New York, p. 73.

Hoh, The linguistic advantage of the intellectually gifted child: An empirical study of spontaneous speech, Roeper Review, 2005, vol. 27, No. 3, pp. 178-185.

Hoh, Writing as the second phase of language acquisition: Emergent grammar in basic writing, 1992, Ph.D. thesis, University of Delaware, Newark, DE.

Hua et al., Phonological development and disorders in children: A multilingual perspective, 2006, Multilingual Matters, Clevedon, UK.

Huber et al., Workshop on assistive augmentation, Proceedings of CHI 2014, Apr. 26-May 1, 2014, Toronto, ON, Canada, pp. 103-106.

Ibanescu et al., Aphasia: Symptoms, diagnosis, and treatment, 2009, Nova Science Publishers, New York.

Ingram, First language acquisition: Method, description, and explanation, 1989, Cambridge University Press, Cambridge.

Institute for Multi-Sensory Education, Shopping Catalog, http://orton-gillingham.com, date accessed on internet Sep. 17, 2014, 5 pages.

International Dyslexia Association, Information on Interventions and Instructions, http://www.interdys.org, nd, date accessed on internet Sep. 14, 2014, 4 pages.

Keenan et al., Test differences in diagnosing reading comprehension deficits, Journal of Learning Disabilities, 2014, vol. 47, pp. 125-135.

Klingberg et al., Microstructure of temporo-parietal white matter as a basis for reading ability: Evidence from diffusion tensor magnetic resonance imaging, Neuron, 2000, vol. 25, pp. 493-500.

Kovelman et al., Brain basis of phonological awareness for spoken language in children and its disruption in dyslexia, Cerebral Cortex, 2012, vol. 22, pp. 754-764.

Krasegnor et al., Biological and behavioral determinants of language development, Chapter 19 by RICE, Children with Specific Language Impairment: Toward a model of teachability, 1991, Lawrence Erlbaum, Hillsdale, NJ, pp. 447-465.

Krzeszowski, Contrasting languages: The scope of contrastive linguistics, 1990, Mouton de Gruyter, Berlin.

Kurtz, Understanding controversial therapies for children with autism, attention deficit disorder, and other learning disabilities, 2008, Jessica Kingsley Publishers, London.

Kurzweil Education, Dyslexia and Kurzweil 3000, http://www.kurzweiledu.com/default.html, date accessed on internet Sep. 18, 2014, 4 pages.

Laasonen et al., Project DyAdd: Implicit learning in adult dyslexia and ADHD, Annals of Dyslexia, 2014, vol. 64, pp. 1-33.

Lacerda et al., Emerging Cognitive Abilities in Early Infancy, Chapter 5 by Lacerda et al. Auditory and Articulatory Biases Influence the Initial Stages of the Language Acquisition Process, Lawrence Erlbaum Associates Publishers, 2001, pp. 91-110.

Lahm, Assistive technology specialists: Bringing knowledge of assistive technology to school districts, Remedial and Special Education, 2003, vol. 24, No. 3, pp. 141-153.

Laing et al., Phonological and semantic processes influence beginning readers' ability to learn to read words, Journal of Experimental Child Psychology, 1999, vol. 73, No. 3, pp. 183-207.

Larkin et al., Comparing phonological skills and spelling abilities in children with reading and language impairments, International Journal of Language and Communication, 2008, vol. 43, No. 1, pp. 111-124.

Larsen-Freeman, Second language acquisition research: Staking out the territory, TESOL Quarterly, 1991, vol. 25, No. 2, pp. 315-350.

Leach et al., Late-emerging reading disabilities, Journal of Educational Psychology, 2003, vol. 95, No. 2, pp. 211-224.

Lee et al., The nation's report card: Reading 2007 (NCES 2007-496), 2007, National Center for Education Statistics, Institute of Education Sciences, US Department of Education, Washington, DC, 68 pages.

Leonard et al., Cerebral asymmetry and cognitive development: A magnetic resonance imaging study, Psychological Science, 1996, vol. 7, No. 2, pp. 89-95.

Levy et al., Fast and slow namers: benefits of segmentation and whole word training, Journal of Experimental Child Psychology, 1999, vol. 73, No. 2, pp. 115-138.

Lexercise, website, http://www.lexercise.com, date accessed on internet Sep. 17, 2014, 3 pages.

Lindamood, The need for phonemic awareness, American Speech Language Hearing Association, 1998, vol. 40, No. 2, pp. 44-45.

Lindamood-Bell, website, http://www.lindamoodbell.com, date accessed on internet Dec. 17, 2014, 4 pages.

Loban, A study of the use and control of language and the relations among speaking, reading, writing, and listening, NCTE Research Report No. 1, 1963, National Council of Teachers of English, Champaign, IL.

Lorusso et al., Neuropsychological treatment of dyslexia: Does type of treatment matter? Journal of Learning Disabilities, 2011, vol. 44, pp. 136-149.

Ludlow, Blurring the line between assistive and mainstream technologies, Teaching Exceptional Children, 2014, vol. 47, No. 1, p. 7.

MacArthur, Assistive technology for struggling writers, Perspectives on Language and Literacy, 2009, vol. 35, No. 3, pp. 31-33.

MacWhinney, The emergence of language, 1999, Lawrence Erlbaum, Mahwah, NJ.

Markey et al., Exceptional writing in a young adult with Down syndrome, Down Syndrome Research and Practice, 2009, doi:10.3104/case-studies.2030, pp. 1-10.

Martin et al., Test of Auditory Processing Skills (TAPS-3) (#1018-IN), Academic Communication Associates, http://www.acadcom.com/ACAwebsite/prodView.asp?idproduct=801, 2005, date accessed on internet Sep. 12, 2014, 2 pages.

Martin, English text: System and structure, 1992, John Benjamins, Philadelphia, PA.

Mates, Assistive technologies in the library, 2011, American Library Association, Chicago.

Mather et al., Chapter 5 Individual assessment of academic achievement, APA Handbook of Testing and Assessment in Psychology: vol. 3, American Psychological Association, 2013, pp. 101-128.

Mattes et al., Language Exercises for Auditory Processing (LEAP) (#40081DL-IN), Academic Communication Associates, 1996, 1 page.

Mayo Clinic, Dyslexia—Definition, http://www.mayoclinic.org/diseases-conditions/dyslexia/basics/definition/con-20021904, 2014, date accessed on internet Sep. 7, 2014, 1 page.

McCawley, The syntactic phenomena of English—vol. 1, Chapter 1, 1988, The University of Chicago Press, Chicago, pp. 1-11.

McCutchen, Knowledge, processing, and working memory: Implications for a theory of writing, Educational Psychologist, 2000, vol. 35, No. 1, pp. 13-23.

McGraw-Hill Education, Early interventions in reading 2012 SRA, https://www.mheonline.com/program/view/4/1/2542/SRAEIRLV11/, 2014c, date accessed on internet Sep. 18, 2014, 4 pages.

McGraw-Hill Education, Fast Track Reading, https://www.mheonline.com/program/view/4/1/124/0076034240/, 2014b, date accessed on internet Sep. 18, 2014, 2 pages.

McGraw-Hill Education, FLEXLiteracy, https://www.mheonline.com/assets/pdf/program/flex_overview_brochure.pdf, 2014a, date accessed on internet Sep. 18, 2014, 16 pages.

McGraw-Hill Education, Overview of ALEKS, http://www.aleks.com/about_aleks/course_products, 2014d, date accessed on internet Sep. 30, 2014, 3 pages.

McIntyre et al., Exploring the potential of LiPS instruction for beginning readers, Developmental Disabilities Bulletin, 2008, vol. 36, No. 1 & 2, pp. 18-48.

Menyuk et al., Early language development in full-term and premature infants, 1995, Lawrence Erlbaum, Hillsdale, NJ.

(56) References Cited

OTHER PUBLICATIONS

Menyuk, Language and maturation, 1977, MIT Press, Cambridge, MA.
Moats et al., Knowledge and practice standards for teachers of reading, http://www.interdys.org/EWEBEDITPRO5/UPLOAD/KPS3-1-12.PDF, 2010, International Dyslexia Association, Baltimore, MD, 35 pages.
Multi-Sensory Learning, website, http://msl-online.net, 2014, date accessed on internet Sep. 17, 2014, 2 pages.
National Early Literacy Panel, Developing early literacy: Report of the National Early Literacy Panel, 2008, National Institute for Literacy, Washington, DC.
National Geographic Learning, High Point, http://www.ngsptechnology.com/tabid/88/Defauit.aspx, date accessed on internet Sep. 18, 2014, 3 pages.
National Institute of Child Health and Human Development, Learning Disabilities Research Centers (LDRC) Consortium, http://www.nichd.nih.gov/research/supported/pages/ldrc.aspx, date accessed on internet Sep. 17, 2014, 4 pages.
National Reading Panel, Teaching children to read: An evidence-based assessment of the scientific literature on reading and its implications for reading instruction, 2000, National Institute of Child Health and Human Development, Bethesda, MD.
Neitzel, Current research on early intervening services for young children at risk for learning difficulties, Perspectives on Language and Literacy, 2011, vol. 37, No. 3, pp. 13-15.
Nespor et al., Prosodic phonology, 2007, Mouton de Gruyter, Berlin.
Neuman et al., Handbook of early literacy research, 2002, Guilford Press, New York.
Newman et al., Students with Both Gifts and Learning Disabilities, Identification, Assessment and Outcomes, Kluwer Academic/Plenum Publishers, Preface, 2004, 4 pages.
Nicholson et al., Matthew effects and reading interventions, Perspectives on Language and Literacy, 2011a, vol. 37, No. 4, pp. 28-33.
Nicholson, Beyond Reading Recovery®—What works best? Perspectives on Language and Literacy, 2011b, vol. 37, No. 4, pp. 7-12.
Nicolson et al., Development of objective procedures for screening and assessment of dyslexic students in higher education, Journal of Research in Reading, 1997, vol. 20, No. 1, pp. 77-83.
Norton, Using cognitive neuroscience to examine the brain basis of pre-reading skills in kindergarten children and subtypes of risk for dyslexia: Toward MRI and EEG prediction of reading outcomes, Ph.D. dissertation, 2012, Tufts University.
O'Grady, Principles of grammar and learning, 1987, The University of Chicago Press, Chicago.
Okolo et al., Disciplinary literacy and technology for students with learning disabilities, Perspectives on Language and Literacy, 2013, vol. 39, No. 4, pp. 29-33.
Olson et al., A cognitive strategies approach to reading and writing instruction for English language learners in secondary school, Research in the Teaching of English, 2007, vol. 41, No. 3, pp. 269-303.
Olson, Evaluation of Fast ForWord® language effects on language and reading, Perspectives on Language and Literacy, 2011, vol. 37, No. 1, pp. 11-15.
One Minute Reader, Application for iPad, http://www.oneminutereader.com/, 2014, date accessed on internet Sep. 18, 2014, 2 pages.
Parkin et al., Are we yet able to hear the signal through the noise? A comprehensive review of central auditory processing disorders: Issues of research and practice, Canadian Journal of School Psychology, 2003, vol. 18, No. 1/2, pp. 153-182.
Pearson Education, CELF®-4 (Clinical Evaluation of Language Fundamentals—$4^{th}$ edition), 2008, PsychCorp, San Antonio, TX.
Pennington, Controversial therapies for dyslexia, Perspectives on Language and Literacy, 2011, vol. 37, No. 1, pp. 7-8.
Plucker et al., Critical issues and practices in gifted education: What the research says, Chapter 5 by Hoh, Cognitive characteristics of the gifted, 2008, Prufrock Press, Waco, TX, pp. 57-81.
Poldrack et al., Relations between the neural bases of dynamic auditory processing and phonological processing: Evidence from fMRI, Journal of Cognitive Neuroscience, vol. 13, No. 5, pp. 687-697.
Popović et al., Towards automatic error analysis of machine translation output, Computational Linguistics, 2011, vol. 37, No. 4, pp. 657-688.
Psychcorp, Process Assessment of the Learner—$2^{nd}$ edition: Diagnostics for Reading and Writing (PAL-II Reading and Writing), http://www.pearsonclinical.com/education/products/100000583/process-assessment-of-the-learner-second-edition-diagnostics-for-reading-and-writing-pal-ii-reading-and-writing.html, 2014, date accessed on internet Sep. 18, 2014, 3 pages.
Rakhlin et al., Spelling well despite developmental language disorder: What makes it possible? Annals of Dyslexia, 2013, vol. 63, pp. 253-273.
Randolph et al., Assessing fit of nontraditional assistive technologies, ACM Transactions on Accessible Computing, 2010, vol. 2, No. 4, Article 16, 31 pages.
Raschle et al., Structural brain alterations associated with dyslexia predate reading onset, NeuroImage, 2011, vol. 57, pp. 742-749.
Raver et al., At the crossroads of education and developmental neuroscience: Perspectives on executive function, Perspectives on Language and Literacy, 2014, vol. 40, No. 2, pp. 27-30.
Reiter et al., Reading disabilities related to word recognition: Underlying deficits and diagnostic approaches, Canadian Journal of School Psychology, 2001, vol. 17, No. 1, pp. 65-84.
Richgels, Professional Library: Phonemic awareness, The Reading Teacher, 2001, vol. 55, No. 3, pp. 274-278.
Ritchey et al., Orton-Gillingham and Orton-Gillingham-based reading instruction: A review of the literature, The Journal of Special Education, Fall 2006, vol. 40, No. 3, pp. 171-183.
Rose et al., Orton-Gillingham methodology for students with reading disabilities: 30 years of case law, The Journal of Special Education, 2007, vol. 41, No. 3, 171-185.
Rose, Identifying and teaching children and young people with dyslexia and literacy difficulties, The Rose Report, 2009, DCSF Publications, Nottingham, UK.
Sadoski et al., Effects of a theoretically based large-scale reading intervention in a multicultural urban school district, American Educational Research Journal, 2006, vol. 43, No. 1, pp. 137-154.
Sanders, Error analysis in purely syntactic parsing of free input: The example of German, CALICO Journal, 1991, vol. 9, No. 1, pp. 72-89.
Saville-Troike, Introducing second language acquisition, $2^{nd}$ edition, 2012, Cambridge University Press, New York.
Schaffhauser, Assistive tech goes mainstream, The Education Digest, Dec. 2013, pp. 51-56.
Scholastic, Read 180, http://teacher.scholastic.com/products/read180/read-180-experience/reading-program-design.htm, 2013, date accessed on internet Sep. 18, 2014, 4 pages.
Scientific Learning Corporation, Fast ForWord® Language Series, http://scilearn.com/products/fast-forword-language-series, 2014, date accessed on internet Sep. 17, 2014, 7 pages.
Shaywitz et al., Persistence of dyslexia: The Connecticut longitudinal study at adolescence, Pediatrics, 1999, vol. 104, No. 6, pp. 1351-1359.
Shaywitz, Overcoming dyslexia: A new and complete science-based program for reading problems at any level, 2003, Alfred A. Knopf, New York.
Shrank et al., Woodcock-Johnson® IV, 2014, Riverside Publishing, Rolling Meadows, IL.
Smythe, Dyslexia in the digital age: Making IT work, 2010, Continuum, London.
Snow, Preventing reading difficulties in young children, 1998, National Academy Press, Washington, DC.
Snow, Reading for understanding, 2002, RAND, Santa Monica, CA.
Snowling, Dyslexia, 2000, Blackwell Publishers, Oxford, UK.
Spreen et al., Assessment of aphasia, 2003, Oxford University Press, Oxford.

(56) References Cited

OTHER PUBLICATIONS

Sprenger-Charolles et al., Prevalence and reliability of phonological, surface, and mixed profiles in dyslexia: A review of studies conducted in languages varying in orthographic depth, Scientific Studies of Reading, 2011, vol. 15, No. 6, pp. 498-521.
ST4 Learning, WordQ, http://www.goqsoftware.com/wordQ.php?gclid=CN6P3K-18KwCFRECQAod9TKxKg, nd, date accessed on internet Sep. 18, 2014, 2 pages.
Stark et al., Cognitive abilities of language-delayed children, The Journal of Psychology, 1983, vol. 114, pp. 9-19.
Sternberg et al., Our labeled children: What every parent and teacher needs to know about learning disabilities, 1999, Perseus, Cambridge, MA.
Stollman et al., Development of an auditory test battery for young children: A pilot study, International Journal of Audiology, 2004, vol. 43, pp. 330-338.
Stone et al., Handbook of language and literacy: Development and disorders, $2^{nd}$ edition, 2014, Guilford Press, New York.
Strickland, Teaching phonics today: Word study strategies through the grades, $2^{nd}$ edition, 2011, International Reading Association, Newark, DE.
Swanson et al. Handbook of learning disabilities, $2^{nd}$ edition, 2013, The Guilford Press, New York.
Talking Fingers, Read, Write & Type, http://www.talkingfingers.com/product_tour/, date accessed on internet Sep. 18, 2014, 6 pages.
Talking Fingers, Wordy Qwerty, http://www.talkingfingers.com/spelling-software-wordyqwerty/reading-spelling-fluency.html, date accessed on internet Sep. 18, 2014, 2 pages.
Tallal, Improving neural response to sound improves reading, PNAS, Oct. 9, 2012, vol. 109, No. 41, pp. 16406-16407.
Tallal, Language learning disabilities: Integrating research approaches, Current Directions in Psychological Science, 2003, vol. 12, No. 6, pp. 206-211.
Tam et al., A reading instruction intervention program for English-language learners who are struggling readers, The Journal of Special Education, 2006, vol. 40, No. 2, pp. 79-93.
Tamboer et al., Identifying dyslexia in adults: An iterative method using the predictive value of item scores and self-report questions, Annals of Dyslexia, 2014, vol. 64, pp. 34-56.
Tartter, Language processes, 1986, Holt, Rinehart and Winston, New York.
Taub et al., Dyslexia, Journal of Behavioral Optometry, 2011, vol. 22, No. 2, pp. 48-49.
Temple et al., Brain mechanisms of quantity are similar in 5-year-old children and adults, PNAS, Jun. 1998, vol. 95, pp. 7836-7841.
Temple et al., Disrupted neural responses to phonological and orthographic processing in dyslexic children: An fMRI study, NeuroReport, 2001, vol. 12, No. 2, pp. 299-307.
Temple, Brain mechanisms in normal and dyslexic readers, Current Opinion in Neurobiology, 2002, vol. 12, pp. 178-183.
Temple, Changes in brain function in children with dyslexia after training, The Phonics Bulletin, May 2003, vol. 1, pp. 1-3.
Thomas et al., Are developmental disorders like cases of adult brain damage? Implications from connectionist modelling, Behavioral and Brain Sciences, 2002, vol. 25, pp. 727-788.
Tong et al., Morphological and syntactic awareness in poor comprehenders: Another piece of the puzzle, Journal of Learning Disabilities, 2014, vol. 47, pp. 22-33.
Tops et al., Identifying students with dyslexia in higher education, Annals of Dyslexia, 2012, vol. 62, pp. 186-203.
Tops et al., Spelling in adolescents with dyslexia: Errors and modes of assessment, Journal of Learning Disabilities, 2014, vol. 47, pp. 295-306.
Torgesen et al., Preventing reading failure in young children with phonological processing disabilities: Group and individual responses to instruction, Journal of Educational Psychology, 1999, vol. 91, No. 4, pp. 579-593.
Torgesen, The prevention of reading difficulties, Journal of School Psychology, 2002, vol. 40, No. 1, pp. 7-26.
Törmänen et al., Auditory-visual matching and language-based learning disorders: Two studies of specific language impairment and developmental dyslexia, International Journal of Education, 2009, vol. 1, No. 1, pp. 1-26.
Tzouveli et al., Adaptive reading assistance for the inclusion of students with dyslexia: The AGENT-DYSL approach, http://www.math.ntua.gr/~symvonis/publications/c_2008_TSSSK_Adaptive Reading Assistance for the Inclusion of Students with Dyslexia The AGENT-DYSL approach.pdf, 8th IEEE International Conference on Advanced Learning Technologies, 2008, date accessed on internet Sep. 14, 2014, 5 pages.
Vellutino et al., Specific reading disability (dyslexia): What have we learned in the past four decades? Journal of Child Psychology and Psychiatry, 2004, vol. 45, No. 1, pp. 2-40.
Vihman, Phonological development: The first two years, $2^{nd}$ edition, 2014, Wiley Blackwell, Southern Gate, UK.
Vukovic et al., The Double-Deficit Hypothesis: A comprehensive analysis of the evidence, Journal of Learning Disabilities, 2006, vol. 39, No. 1, pp. 25-47.
Wallach, Peeling the onion of auditory processing disorder: A language/curricular-based perspective, Language, Speech, and Hearing Services in Schools, 2011, vol. 42, pp. 273-285.
Wanner, Selected lexical and grammatical issues in the Meaning—Text Theory, 2007, John Benjamins, Amsterdam.
Wanzek et al., Research-based implications from extensive early reading interventions, School Psychology Review, 2007, vol. 36, No. 4, pp. 541-561.
Wechsler Adult Intelligence Scale, Fourth Edition (WAIS-IV), Pearson http://www.pearsonclinical.com/education/products/100000392/wechsler-adult-intelligence-scalefourth-edition-wais-iv.html, 2008, date accessed on internet Sep. 14, 2014, 1 page.
Wegner et al., Language-based learning disorders, Pediatric Annals, 2005, vol. 34, No. 4, pp. 300-309.
Weiss et al., Newborn Attention, Biological Constraints and the Influence of Experience, Chapter 11 by Lewkowicz, Development of Intersensory Functions in Human Infancy: Auditory/Visual Interactions, Alex Publishing Corporation, 1991, pp. 308-338.
Weissenborn et al., Theoretical issues in language acquisition: Continuity and change in development, 1992, Lawrence Erlbaum, Hillsdale, NJ.
West, RTI approaches to early intervening supports, Perspectives on Language and Literacy, 2011, vol. 37, No. 3, pp. 17-20.
Wiederholt et al., GORT-5: Gray Oral Reading Tests—$5^{th}$ edition, 2012, PRO-ED, Austin, TX.
Wilson et al., Effects of a perceptual remediation program on reading performance, Journal of Learning Disabilities, 1976, vol. 9, No. 10, pp. 62-70.
Wilson Language Training®, Wilson Reading System® description, http://www.wilsonlanguage.com/fs_program_wrs.htm, 2010, date accessed on internet Sep. 7, 2014, 1 page.
Winters et al., Mobile instructional and assistive technology for literacy, Perspectives on Language and Literacy, 2013, vol. 39, No. 4, pp. 42-46.
Wolff, RAN as a predictor of reading skills, and vice versa: Results from a randomised reading intervention, Annals of Dyslexia, 2014, vol. 64, pp. 151-165.
Yale Center for Dyslexia and Creativity, website, http://dyslexia.yale.edu, 2014, date accessed on internet Sep. 14, 2014, 1 page.
Yin, Dyslexia in Chinese: Clues from Cognitive Neuropsychology, Annals of Dyslexia, 2003, vol. 53, pp. 255-279.
International Search Report and Written Opinion dated Feb. 19, 2015 in related PCT Application No. PCT/US14/62946 filed Oct. 29, 2014 (8 pages).

\* cited by examiner

WORD SEGMENTATION
Stimulus Item *be*
Task: Patient is asked to segment the word *be* into its individual sounds.

COMPUTING TECHNOLOGIES FOR DIAGNOSIS AND THERAPY OF LANGUAGE-RELATED DISORDERS

CROSS-REFERENCE TO RELATED APPLICATIONS

The present application claims priority to U.S. Provisional Patent Application Ser. No. 61/898,052, filed on Oct. 31, 2013, which is herein fully incorporated by reference for all purposes.

TECHNICAL FIELD

Generally, the present disclosure relates to computing. More particularly, the present disclosure relates to computing technologies for diagnosis and therapy of language-related disorders.

BACKGROUND

In the present disclosure, where a document, an act and/or an item of knowledge is referred to and/or discussed, then such reference and/or discussion is not an admission that the document, the act and/or the item of knowledge and/or any combination thereof was at the priority date, publicly available, known to the public, part of common general knowledge and/or otherwise constitutes prior art under the applicable statutory provisions; and/or is known to be relevant to an attempt to solve any problem with which the present disclosure is concerned with. Further, nothing is disclaimed.

Language underlies much of human mental and communicative functioning. Consequently, a disorder which hampers a part of language performance can carry broad or significant detrimental effects. Some prevalent examples of such disorder comprise a language-related disorder such as dyslexia, specific language impairment (SLI), auditory processing disorder (APD), aphasia, or others. For instance, although dyslexia is commonly considered a reading disorder, individuals with such condition often experience a host of other difficulties as well. Among such difficulties are problems with speech articulation, attention, or memory. Accordingly, some of such individuals can often struggle in school, especially at great personal cost, since dyslexia affects many basic language and cognitive functions. Others often drop out of school and suffer self-esteem or other psycho-social problems. However, despite pervasiveness of such language disorders, a large number of professionals, such as teachers or therapists, are not trained accordingly.

Such problematic state of being is further compounded by a fact that some language-related disorders, such as dyslexia, cover a broad spectrum of deficits. Resultantly, whether such disorders are even useful as a construct for research and evaluation remains questionable. Furthermore, many existing diagnostic tests for language-related disorders are not designed for administration to large groups, while allowing for self-pacing and customization according to each individual user's deficit(s). Worse, many providers simply stop at diagnosis and do not proceed to recommend therapy to address even most of the deficits found based on the diagnosis. At best, some providers, who do link therapy to diagnosis, use evaluation results to select preset therapy modules intended for all users performing at a certain level of competency.

Although intervention can be useful in treating such disorders, at present, a state of intervention therapy for reading disability is discouraging. For example, some reading disability interventions in middle schools have yielded disappointing results. Furthermore, some popular methodologies of reading instruction, such as Orton-Gillingham approach or Orton-Gillingham-based approaches, have not produced sufficient scientific evidence of efficacy in part or in whole.

BRIEF SUMMARY

The present disclosure at least partially addresses at least one of the above. However, the present disclosure can prove useful to other technical areas. Therefore, the claims should not be construed as necessarily limited to addressing any of the above.

A system of one or more computers can be configured to perform particular operations or actions by virtue of having software, firmware, hardware, or a combination of them installed on the system that in operation causes or cause the system to perform the operations or the actions. One or more computer programs can be configured to perform particular operations or actions by virtue of including instructions that, when executed by a data processing apparatus, cause the apparatus to perform the operations or the actions.

An example embodiment of the present disclosure includes a method comprising: diagnosing a language-related disorder via: obtaining a first set of criteria via a first computer, wherein the first set of criteria is based on a first analysis of a patient data structure against a master data structure, wherein the patient data structure comprising a set of actual patient task responses, wherein the master data structure comprising a set of cell generation data and a set of predicted patient task responses for a plurality of patients; storing a first result in the patient data structure via the first computer, wherein the first result is received from a second computer, wherein the first result is based on the first computer selecting a first diagnostic shell based on the first set of criteria, generating a first diagnostic cell based on the first diagnostic shell and the set of cell generation data, and communicating the first diagnostic cell to the second computer; obtaining a second set of criteria via the first computer, wherein the second set of criteria is based on a second analysis of the patient data structure, including the first result, against the master data structure; and determining at least one of whether to generate a second diagnostic cell and whether to select a second diagnostic shell via the first computer, wherein the second diagnostic cell is based on the first diagnostic shell, wherein the first diagnostic shell and the second diagnostic shell are different in task type.

An example embodiment of the present disclosure includes a system comprising: a first computer facilitating a diagnosis of a language-related disorder via: obtaining a first set of criteria, wherein the first set of criteria is based on a first analysis of a patient data structure against a master data structure, wherein the patient data structure comprising a set of actual patient task responses, wherein the master data structure comprising a set of cell generation data and a set of predicted patient task responses for a plurality of patients; storing a first result in the patient data structure, wherein the first result is received from a second computer, wherein the first result is based on the first computer selecting a first diagnostic shell based on the first set of criteria, generating a first diagnostic cell based on the first diagnostic shell and the set of cell generation data, and communicating the first diagnostic cell to the second computer; obtaining a second set of criteria, wherein the second set of criteria is based on a second analysis of the patient data structure, including the first result, against the master data structure; determining at least one of whether to generate a second diagnostic cell and whether to select a second diagnostic shell, wherein the second diagnostic cell is based on the first diagnostic shell, wherein the first diagnostic shell and the second diagnostic shell are different in task type.

An example embodiment of the present disclosure includes a non-transitory, computer-readable storage medium storing a set of instructions for execution via a hardware processor, wherein the set of instructions instructing the hardware processor to implement a method, the method comprising: diagnosing a language-related disorder via: obtaining a first set of criteria via a first computer, wherein the first set of criteria is based on a first analysis of a patient data structure against a master data structure, wherein the patient data structure comprising a set of actual patient task responses, wherein the master data structure comprising a set of cell generation data and a set of predicted patient task responses for a plurality of patients; storing a first result in the patient data structure via the first computer, wherein the first result is received from a second computer, wherein the first result is based on the first computer selecting a first diagnostic shell based on the first set of criteria, generating a first diagnostic cell based on the first diagnostic shell and the set of cell generation data, and communicating the first diagnostic cell to the second computer; obtaining a second set of criteria via the first computer, wherein the second set of criteria is based on a second analysis of the patient data structure, including the first result, against the master data structure; and determining at least one of whether to generate a second diagnostic cell and whether to select a second diagnostic shell via the first computer, wherein the second diagnostic cell is based on the first diagnostic shell, wherein the first diagnostic shell and the second diagnostic shell are different in task type.

BRIEF DESCRIPTION OF THE DRAWINGS

The accompanying drawings illustrate example embodiments of the present disclosure. Such drawings are not to be construed as necessarily limiting the disclosure. Like numbers and/or similar numbering scheme can refer to like and/or similar elements throughout.

DETAILED DESCRIPTION OF THE PREFERRED EMBODIMENTS

Figure 1:
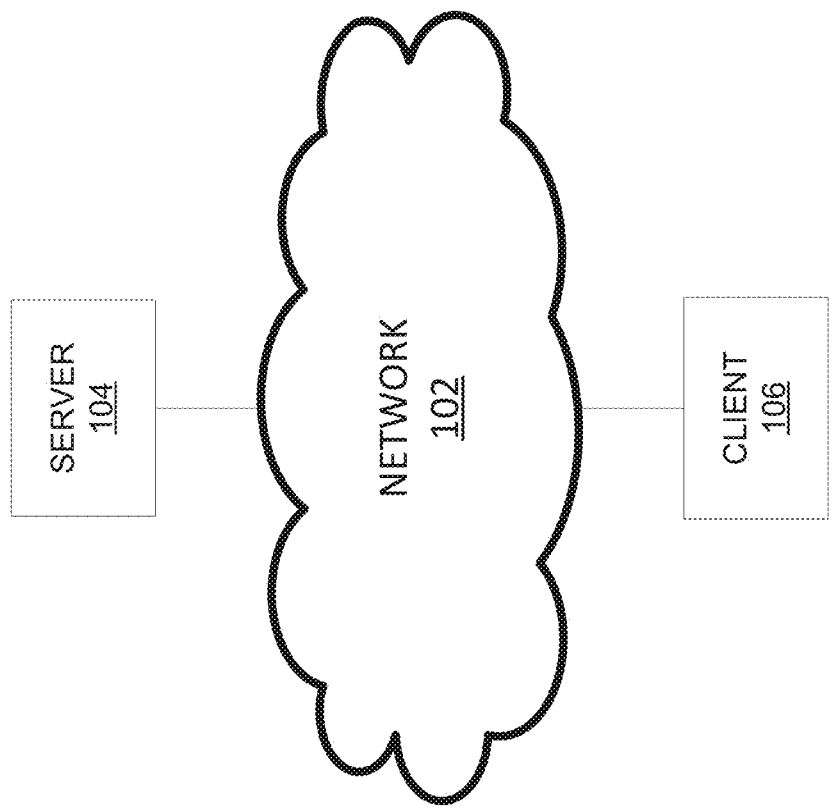
FIG. 1 shows a schematic view of an example embodiment of a computer network model according to the present disclosure.

The present disclosure is now described more fully with reference to the accompanying drawings, in which example embodiments of the present disclosure are shown. The present disclosure may, however, be embodied in many different forms and should not be construed as necessarily being limited to the example embodiments disclosed herein. Rather, these example embodiments are provided so that the present disclosure is thorough and complete, and fully conveys the concepts of the present disclosure to those skilled in the relevant art.

Features described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity in any manner.

The terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

The terminology used herein is for describing particular example embodiments and is not intended to be necessarily limiting of the present disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

As used herein, the term "about" and/or "substantially" refers to a +/−10% variation from the nominal value/term. Such variation is always included in any given value/term provided herein, whether or not such variation is specifically referred thereto.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

In some embodiments, the present disclosure enables a computing technology for providing individualized diagnosis and therapy to patients with language-related disorders. The technology enables computer-generated diagnosis and computer-generated therapy delivered over a network to at least one computing device. The diagnosis and therapy are customized for each patient through a comprehensive analysis of the patient's production and reception errors, as obtained from the patient over the network, together with a set of correct responses at each level of evaluation and therapy. The technology performs such error analysis via matching the patient's responses to a preset matrix of all possible correct and incorrect responses predicted for a patient population involved. This error analysis enables the technology to provide individual-specific diagnostic and therapy cells that efficiently and comprehensively target a specific language-processing deficit underlying the patient's disability. Each of the cells is a test and/or a practice unit focused on an aspect of language and/or language function. The technology further enables a database storing the patient's correct responses and ill-formed productions based on which a learning analytics computer algorithm or a similar approach is employed to monitor and improve an efficacy of the technology in correcting language-processing deficits. As the present disclosure relates to language processing, the scope of the present disclosure further extends beyond language structures to communicative and/or cognitive functions served by language. As scientific understanding of language-related disorders and disabilities improves, the present disclosure can also serve as a preventive program for populations identified to be at risk. Note that although the language-related disorder comprises at least one of dyslexia, specific language impairment, auditory processing disorder, and aphasia, other language-related disorders are included as well.

In some embodiments, the present disclosure enables a use of the patient's diagnostic results to generate the content of the patient's customized therapy. Via using a computerized diagnostic and therapy program, while delivering network services to a variety of remote devices, the present disclosure is both relatively efficient and cost-effective in reaching large numbers of patients with disorders affecting language processing, such as speech disorders, dyslexia, aphasia, or others known to skilled artisans. Via using cloud computing and/or other network technologies with comparable advantages, the present disclosure offers convenience as a computerized program accessible to a plurality of mobile users at any time or day, thus strengthening the program's efficacy. The present disclosure enables both running the program and saving at least some patient data on remote servers, thereby expanding a number of remote devices which can be employed by patients.

The present disclosure aims to diagnose, evaluate, and treat language-related disorders in several unique respects. First, in some embodiments, a diagnosis based on the present disclosure is definitive because the diagnosis is based at least in part on a deterministic model, identifying a set of specific problem areas in the language functions and structures of each patient. Each level of evaluation confirms and validates the analyses of prior levels. Currently, there is no comparable definitive diagnostic test for dyslexia known, as dyslexia in a patient is gauged through a set of tests covering a broad spectrum of verbal and cognitive abilities, since dyslexia is considered an unexpected anomaly in an otherwise fully functioning individual with an intelligence quotient (IQ) in a normal range. Therefore, to diagnose dyslexia, a psychologist presently may administer a Wechsler Intelligence Scale for Children-IV Integrated (WISC-IV), Wechsler Individual Achievement Test-Ill (WIAT-III), Boston Naming Test, Menyuk Syntax Comprehension Test, Wide Range Assessment of Memory and Learning-II (WRAML-II), Peabody Picture Vocabulary Test-IV, together with a neuropsychological assessment and tests of executive functioning. Such tests are time-consuming for certified specialists to administer and therefore are too costly for most families. Furthermore, diagnoses based on such testing are typically probabilistic, based on normative data. Although some segments of scientific community state currently that IQ testing is unnecessary to diagnose dyslexia, the relevant field still lacks a reliable diagnostic instrument.

Second, in some embodiments, the present disclosure enables a creation of an individualized evaluation and therapy. The present disclosure enables a more definitive diagnosis and an efficient and effective therapy because the disclosed technology analyzes and/or addresses each patient's reception and production errors at every phase of her training. The program individually customizes diagnostic and therapy cells to address the underlying language-processing problems of each user. For example, if a patient makes errors with the /ϴ/ ("th") sound during a phoneme identification test during a diagnosis phase, then words with this /Θ/ sound are included in a word segmentation test during further diagnostic testing to confirm the problem and obtain finer details of her processing deficit. These details may include a sound environment in which such problems with /Θ/ occurs. The sound environment is a phonological context surrounding a particular phoneme, such as a sound adjacent to that phoneme and/or the position of that phoneme in a word, such as word-initial, word-medial, and/or word-final position. For example, a patient may have difficulty with the phoneme /Θ/ in the word-final position, such as tee<u>th</u>, but not in the word-initial position, such as <u>th</u>ink. In contrast, currently, many clinicians use pre-set diagnostic tests, which are uniformly applied to all patients. Moreover, currently used methodologies that purport to be "individual-based" merely move users to the next pre-set test and/or training at a higher or same level of difficulty based on prior performance. Such pre-set, linear programs cannot "fine-tune" their training regime because such programs cannot analyze the patterns of errors created by users during their performance of tasks and use the analysis results to develop subsequent therapy, which the present disclosure enables. Moreover, the present disclosure enables "future-proofing" i.e. a response to newly discovered processing problems at any stage of therapy by generating new therapy cells to correct based thereon. More particularly, diagnosis, evaluation, and/or therapy are tightly integrated in the present disclosure in a non-linear, generative manner, which is important because language-related disorders tend to occur on a continuum with wide individual variation.

Third, in some embodiments, the present disclosure enables correction of—not compensation for—language-processing deficits. More particularly, treatments of dyslexia can generally be divided into those with corrective approaches and those with compensatory approaches. Most providers focus on compensatory techniques and thus typically accept dyslexia as a life-long disability. Indeed, some experts label dyslexia as a life-long condition. The few providers who do attempt to correct the problem have yet to do so successfully in a way that is replicable for the population involved. While some cognitive scientists remain hopeful, such goal is still elusive in the field. Further, some scientists conclude that corrective programs, such as Fast ForWord by Scientific Learning Corporation, have failed to achieve this goal. One reason for this gap between hope and realization is clear in a context of the present disclosure: corrective programs, such as Fast ForWord, cannot address most individual's language-processing problems directly because the corrective programs are based on linear models with pre-set modules. In contrast, the present disclosure is non-linear and responsive to each user's performance at every stage of training. Moreover, such existing methods artificially modify speech input and use non-speech sounds to focus on processing speed. In contrast, the present disclosure does not digitally alter speech signals in such a way that the input no longer sounds like natural speech. Natural speech is an oral production of native speakers with no speech impairments and is produced spontaneously during human interaction in natural settings. Certain prosodic features of natural speech, however, may be exaggerated during moments of excitability or interactions with young children. Indeed, the present disclosure may use as an input a live and/or recorded speech of speakers who exaggerate the prosody of natural speech (i.e., length, pitch, stress) to help users hear the input clearly. The present disclosure does not focus only on auditory processing speed but analyzes the user's production and reception of all components of the language and addresses most, if not all, other underlying issues as well, including lexical (word) representation and retrieval.

Fourth, in some embodiments, the present disclosure enables a comprehensive correction of each user's language-processing problems. One reason why such type of language-related disorder, such as dyslexia, persists is that existing diagnostic, evaluation, and therapy methods are not sensitive to multiple facets of each individual's language deficit. Most current methodologies, at most, record the patients' correct responses and discard incorrect ones. In contrast, the present disclosure enables analysis of the patient's incorrect responses to find patterns of errors identifying specific areas of difficulty. The present technology uses such patterns of errors to build a model of the patient's language reception and production faculties to serve as a roadmap for therapy that targets and corrects only and all the problems specific (or unique) to each person. In the present disclosure, an error analysis is used to compare the patient's actual responses to a set of targeted correct responses. For example, the error analysis may reveal that the patient has difficulty processing articles (the, a, an), based on the patient's omission and incorrect substitutions in contexts requiring the substitutions. This ongoing error analysis throughout a therapy phase allows a computer program to update therapy and evaluation continually, revising as needed. These unique strengths of the program are made possible by the program's predictive feature, which is built on a vast knowledge base of a set of verbal behaviors and outputs of patient populations with such language-processing disorders and a typical population. Therefore, the present disclosure enables an individualized, data-driven methodology, given an absence of an effective standardized approach in reading intervention currently.

Fifth, in some embodiments, the present disclosure enables an application of learning analytics algorithms and other intelligent data processing techniques and/or artificial intelligence (AI) techniques, such as IBM Watson, Apple Siri, Google Now, or Microsoft Cortana, to at least one database of stored patient responses to improve the program efficacy continually. The present disclosure enables data mining of accumulated information to discover, for example, what types of test items are generated frequently and which evaluation units are repeated due to first-attempt failures. The program uses this type of stored information to focus resources on improving content of the most frequently used types of tests and on enhancing an effectiveness of certain therapy cells, as described herein. Such information is stored in a learning analytics database, as described herein. For example, since the program can identify which specific functional areas of the patient's brain are affected, such information, as collected in this database from large groups of users, can be used to predict a path of progress of each new patient, project her therapy schedule, and/or estimate duration of therapy.

In some embodiments, the present disclosure enables a computer program comprising a diagnostic phase and a therapy phase, both of which are based on data hosted in at least one computerized database, in any manner. The program interfaces with at least one database over a network. Note that at least one of the diagnostic phase and the therapy phase can occur, whether in whole or in part, without an intervention of a language-related disorder clinician, whether directly or indirectly.

The diagnostic phase, which can be at least partially performed via a hardware module and/or a software module, comprises a deployment of a plurality of diagnostic shells and a plurality of diagnostic cells. In some embodiments, at least one of the diagnostic shells can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. Each of the diagnostic shells is a procedure for a prescribed activity serving as a test of a language function. Such procedure does not contain any test items. Instead, a test is delivered through a diagnostic cell, which is generated via an insertion of a test item into the diagnostic shell. More particularly, each diagnostic shell is a type of test, while each diagnostic cell is an actual, specific test. In some embodiments, at least one of the diagnostic cells can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. The technology disclosed herein enables generation of diagnostic tests for each patient by placing content into the diagnostic shells. Each test thus generated is a diagnostic cell. For example, if a diagnostic shell involves lexical (word) retrieval, then the program generates a first diagnostic cell involving nouns and a second diagnostic cell involving verbs. The program generates a diagnostic cell via retrieving specific items and/or a specific set of items from a first data structure, such as a master matrix. Note that other types of data structures can be used as well, such as a queue, a stack, a deck, a linked list, a table, a tree, or others. Further, note that the first data structure can be at least one of indexed and searchable.

Some embodiments of the present disclosure comprise a sound-symbol matching diagnostic shell. For example, such shell involves a patient inputting, such as via a keyboard, whether physical and/or virtual, coupled to a computer running the program and/or such as via selecting from a set of options displayed on a display coupled to the computer running the program, a symbol, such as a letter and/or a character, via matching a sound heard by the patient in an audio recording, such as via typing h for the heard sound /h/, output via the program. The program then matches patient's response against a set of stored correct responses in the data structure, such as the master matrix, and provides a total of the patient's correct responses and other feedback, as needed. The program then matches the patient's incorrect responses to a set of predicted errors, as stored in the data structure, such as the master matrix, to generate a new diagnostic cell and/or a therapy cell.

Some embodiments of the present disclosure comprise a lexical access diagnostic shell. For example, such shell involves a patient listing words according to a specified criterion, such as words that start with "B," by speaking, within set time constraints, into a microphone, which is coupled to a computer running the program, or by typing via a keyboard, whether physical and/or virtual, coupled a computer running the program. The program then matches the patient's responses against a set of correct responses in the data structure, such as the master matrix, and provides a total of the patient's correct responses and other feedback, as needed. The program then classifies the patient's incorrect responses into a set of categories, such as sound-based or phonological errors, meaning-based or semantic errors, and matches the incorrect responses to a set of predicted errors in a relevant category, as stored in the data structure, such as the master matrix, to generate a new diagnostic cell and/or a therapy cell.

Some embodiments of the present disclosure comprise a lexical retrieval diagnostic shell. For example, such shell involves a patient naming an object, as an image of the object is displayed on a display coupled to a computer, via speaking into a microphone, which is coupled to the computer running the program, or selectively activating/clicking on a name from a list/screens of options displayed on the display. The program then matches the patient's responses against a set of stored correct responses in the data structure, such as the master matrix, and provides a total of the patient's correct responses and other feedback, as needed. The program then classifies the patient's incorrect responses into a set of categories, such as sound-based or phonological errors, meaning-based or semantic errors, and matches the incorrect responses to a set of predicted errors in a relevant category, as stored in the data structure, such as the master matrix, to generate a new diagnostic cell and/or a therapy cell.

Some embodiments of the present disclosure comprise a syllabification diagnostic shell. For example, such shell involves a patient breaking up a word, whether auditory output via a speaker coupled to a computer running the program and/or visual output via a display coupled to the computer running the program. Such word break-up occurs via inputting, such as via typing into a keyboard, whether physical or virtual, coupled to the computer running the program and/or speaking into a microphone coupled to the computer running the program, a number of individual syllables in the word in order, such as un-der-stand. The program then matches the patient's responses against a set of stored correct responses, as stored in the data structure, such as the master matrix, and provides a total of the patient's correct responses and other feedback, as needed. The program then matches incorrect responses to a set of predicted errors, as stored in the data structure, such as the master matrix, to generate a new diagnostic cell and/or a therapy cell.

Some embodiments of the present disclosure comprise a word segmentation diagnostic shell. For example, such shell involves a patient breaking up a word displayed on a display coupled to a computer running the program. Such word break-up occurs via speaking the word's individual sound segments in order, such as /klɪ k/ for click into a microphone coupled to the computer running the program. The program then matches the patient's responses against a set of stored correct responses, as stored in the data structure, such as the master matrix, and provides a total of the patient's correct responses and other feedback, as needed. The program then matches incorrect responses to a set of predicted errors, as stored in the data structure, such as the master matrix, to generate a new diagnostic cell and/or a therapy cell.

Some embodiments of the present disclosure comprise a word recognition diagnostic shell. For example, such shell involves a patient hearing a recorded sound or word and/or seeing a symbol or word displayed on a display coupled to a computer running the program. From a passage displayed on the display, the patient picks out any words in print with that sound and/or symbol or that match the uttered word via highlighting, such as via an input device, for instance a keyboard or a touchpad, or clicking on any of such words, such as via an input device, for instance, a mouse. The program then matches the patient's response against a set of correct responses, as stored in the data structure, such as the master matrix, and provides a total of the patient's correct responses and other feedback, as needed. The program then matches incorrect responses to a set of predicted errors, as stored in the data structure, such as the master matrix, to generate a new diagnostic cell and/or a therapy cell.

Some embodiments of the present disclosure comprise a phoneme identification diagnostic shell. For example, such shell involves a patient picking out any word containing a certain sound from a string of output words, whether visually, such as via a display coupled to a computer running the program, and/or auditorily, such as via a speaker coupled to the computer running the program. Such picking out is performed via clicking on a button, whether physical or virtual, on the display and/or repeating the selected word, into the microphone. The program then matches the patient's response against a set of correct responses, as stored in the data structure, such as the master matrix, and provides a total of patient's correct responses and other feedback, as needed. The program then matches the patient's incorrect responses to a set of predicted errors, as stored in the data structure, such as the master matrix, to generate a new diagnostic cell and/or a therapy cell.

Some embodiments of the present disclosure comprise a rhyming diagnostic shell. For example, such shell involves a patient picking out any word that rhymes (response words) with an output word (stimulus word). The output word is output, whether visually, such as via a display coupled to a computer running the program, and/or auditory, such as via a speaker coupled to the computer running the program. Such picking out is performed via clicking on a button, whether physical or virtual, on the display as a response word appears or via speaking a word that rhymes with the output word (stimulus word) into the microphone. The program then matches the patient's response against a set of correct responses, as stored in the data structure, such as the master matrix, and provides a total of the patient's correct responses and other feedback, as needed. The program then matches incorrect responses to a set of predicted errors, as stored in the data structure, such as the master matrix, to generate a new diagnostic cell and/or a therapy cell.

Some embodiments of the present disclosure comprise a morpheme recognition diagnostic shell. For example, such shell involves a patient highlighting with an input device, such as a mouse coupled to a computer running the program and/or typing on a keyboard coupled to the computer running the program, affixes found in any word displayed on a display coupled to the computer running the program. The program then matches the patient's response against a set of correct responses, as stored in the data structure, such as the master matrix, and provides a total of the patient's correct responses and other feedback, as needed. The program then matches incorrect responses to a set of predicted errors, as stored in the data structure, such as the master matrix, to generate a new diagnostic and/or a therapy cell.

Some embodiments of the present disclosure comprise a rapid naming diagnostic shell. For example, such shell involves a patient reading into a microphone, which is coupled to a computer running the program, a word flashed on a display, which is coupled to the computer running the program, under set time constraints or at accelerating speeds. The word may display in any manner, such as one letter at a time from left to right or some letters in different colors or forms. The program then matches the patient's response against a set of correct responses, as stored in the data structure, such as the master matrix, and provides a total of the patient's correct responses at targeted speeds and other feedback, as needed. The program then matches incorrect responses to a set of predicted errors, as stored in the data structure, such as the master matrix, to generate a new diagnostic cell and/or a therapy cell.

Some embodiments of the present disclosure comprise a rapid processing diagnostic shell. For example, such shell involves a patient performing one or more of tests in at least one other diagnostic shell under set time constraints or at accelerating speeds. The program then matches the patient's response against a set of correct responses, as stored in the data structure, such as the master matrix, and provides a total of the patient's correct responses at targeted speeds and other feedback, as needed. The program then matches incorrect responses to a set of predicted errors, as stored in the data structure, such as the master matrix, to generate a new diagnostic cell and/or a therapy cell.

Some embodiments of the present disclosure comprise a reading fluency diagnostic shell. For example, such shell involves a patient reading a passage displayed on a display, which is coupled to a computer running the program, into a microphone, which is coupled to the computer running the program. The program then uses voice or speech recognition software or a live assistant to identify and record reading errors and gives feedback, as needed. The live assistance can be contacted via at least one method, such as a telephone call, a teleconferencing session, a chat, or others. The program then classifies any caught reading errors into a set of categories, such as sound-based or phonological errors, meaning-based or semantic errors, and matches the patient's errors to a set of predicted errors, as stored in the data structure, such as the master matrix, to generate a new diagnostic cell and/or a therapy cell.

Note that any cell test or cell task may be performed through a new modality or a device, such as a touchscreen feature, a clicker, or app. Further, note that any cell test or cell task may be repeated in one cell. Additionally, note that any cell test or cell task may be designed as age-appropriate interactive games.

The therapy phase, which can be at least partially performed via a hardware module and/or a software module, whether distinct from the diagnosis module or as one module, comprises a deployment of a plurality of therapy shells and a plurality of therapy cells. In some embodiments, at least one of the therapeutic shells can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. Note that such embodiments can be identical to and/or be dissimilar to the at least one of the therapeutic shells. The therapy cells are generated from the therapy shells similarly to the diagnosis cells being generated from the diagnosis shells. In some embodiments, at least one of the therapeutic cells can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. Note that such embodiments can be identical to and/or be dissimilar to the at least one of the therapeutic cells. Further, each therapy cell contains a training unit and an evaluation unit. The training unit allows practice with a new drill, while the evaluation unit assesses performance on aspects covered previously or presently. However, in other embodiments, the therapy cells are generated from the therapy shells dissimilarly to the diagnosis cells being generated from the diagnosis shells. Also, in some embodiments, at least one of the training units can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. Furthermore, in some embodiments, at least one of the evaluation units can be embodied via at least one of a set of instructions, a function, a procedure, a call, a routine, a subroutine, a vector, an algorithm, a heuristic, a parameter, a criterion, an applet, a library, an operation, a command, a module, a data structure, for instance, a matrix, a queue, an array, a stack, a deck, a linked list, a table, a tree, or others, a class, an object, a node, a flag, an alphanumeric value, a symbolic value, a hash, a file, a driver, a software application, and/or any combinations and/or equivalents thereof. Note that such embodiments can be identical to and/or be dissimilar to the at least one of the training units.

Some embodiments of the present disclosure comprise a phoneme discrimination therapy shell. For example, such shell involves a computer display showing a minimal pair, such as pit and bit. An audio recording plays one word at a time in random order at a specified speed. The patient selects/clicks on that word, or presses on an arrow key representing each word, as such word is uttered, before the recording plays the next word. The program then matches the patient's responses against a set of stored correct responses in the first data structure, such as the master matrix, and provides a total of the patient's correct responses and other feedback, as needed. The program then matches a total of the patient's correct responses to specified criteria in the first data structure, such as the master matrix, to generate new therapy cells. Note that as part of the therapy phase, the patient may go through an identical phoneme discrimination cell, with an identical minimal pair, multiple times at increasing speeds to improve her auditory processing speed.

Some embodiments of the present disclosure comprise a rapid word recognition therapy shell. For example, such shell involves a computer display showing a minimal pair, such as pit and bit. One of such two words is highlighted, one word at a time in random order at a specified speed. The patient reads that highlighted word by speaking into a microphone as that word is highlighted, before a next word is illuminated. The program then matches the patient's responses against a set of stored correct responses in the first data structure, such as the master matrix, and provides a total of the patient's correct responses and other feedback, as needed. The program matches a total of the patient's correct responses to specified criteria in the first data structure, such as the master matrix, to generate new therapy cells. Note that as part of the therapy phase, the patient may go through an identical rapid word recognition cell, with an identical minimal pair, multiple times at increasing speeds to improve her reading speed.

Some embodiments of the present disclosure comprise a word amplification therapy shell. For example, such shell involves the program playing an audio file and/or a video file of a speaker elongating and amplifying a prosodic feature of a word, such as a /br/ segment in brick or an intonational contour of variety. Alternatively, such amplification is done through a live assistant functionality and/or animation. The patient records her imitation of the amplified form by speaking into a microphone or by using a camera, whether included in and/or coupled to a computer, with or without bodily gestures, such as using a chopping motion to indicate syllable breaks or waving her hand high or low to signal pitch. The program matches the patient's recording against a set of stored parameters in the first data structure, such as the master matrix, and provides a corrective or evaluative feedback as needed, such as lengthen /br/ clusters further to create two distinct segments. The patient answers a series of questions on her articulation of the word in question, such as "Where is the tip of your tongue when you say the /l/ in help?" The program then matches the patient's responses against a set of stored correct responses in the first data structure, such as the master matrix, and provides a total of patient's correct responses and other feedback as needed. The program then matches a total of patient's correct responses to specified criteria in the first data structure, such as the master matrix, to generate new therapy cells.

In the training unit, in some embodiments, each therapy cell focuses on only one specific language-processing problem identified in the patient's response during diagnosis and/or therapy. Each cell is designed to correct only one such problem through sufficient practice, followed by an evaluation to confirm that the deficit has been addressed satisfactorily. For example, if the patient has difficulty processing words with the /ʃ/ sound, then the program generates from the data structure, such as the master matrix, a list containing this /ʃ/ phoneme as well as a syllable, such as /ʃi/, , ə , a real word and/or a nonsense word, such as sure, lush, or shum, and a sentence containing this sound, such as This is surely the best show in town. Each list is then placed into separate shells specifying different tasks. For example, in one such therapy cell, the patient may practice articulating such sound precisely by imitating a syllable or word containing /ʃ/ each time she hears a prompt in a form of a sound recording of this phoneme. Alternatively, she may be required to draw out this sibilant (hissing) sound for a specified duration as indicated by prompts on a display coupled to a computer running the program. In another embodiment, the program uses voice or speech recognition software to give the patient real-time feedback as to an accuracy of each of her oral responses, once a baseline in terms of fundamental frequency has been set for her particular voice. For example, the patient's speech signal is represented as a spectrogram (voiceprint) that is converted by the program into a visual cue on the display indicating a distance between her production and a target form as she tries to approximate the target. In another therapy cell, the user may activate/click, such as via an input device, for instance, a keyboard, whether physical or virtual, a touchpad, a mouse, a clicker, a joystick, or a touchscreen, on a word with such sound from a list displayed on the display. The tasks in the therapy cells may mirror those performed for the diagnostic tests. Other therapy cells may cover other reception and/or production difficulties. The tasks may range from attending to phonetic features to full texts. Collectively, a cluster of cells may cover complex tasks such as reading, while individual cells in the cluster may focus on spelling rules and lexical acquisition (vocabulary building).

In the evaluation unit, in some embodiments, after sufficient practice in the training unit of the therapy cell, the patient proceeds to the evaluation unit of that same cell. The patient performs that same task with test items similar or identical to those in the associated training unit. The user has to pass this evaluation before moving on to a next therapy cell. A passing score is pre-specified in the data structure, such as the master matrix, for each evaluation unit. Correct and incorrect responses are recorded in a second data structure, such as a patient matrix, and used for computer-generation, if needed, of a new therapy cell in a manner as described with reference to the first data structure, such as the master matrix, herein. Note that other types of data structures can be used as well, such as a queue, a stack, a deck, a linked list, a table, a tree, or others. Further, note that the first data structure and the second data structure can be a subset of and/or be a parent data structure. The first data structure and the second data structure can be stored in separate computerized databases, whether remote or local to each other, or in one computerized database. Further, note that the second data structure can be at least one of indexed and searchable.

In another embodiment, the evaluation unit may be separate from the training unit, or more than one evaluation units may accompany a training unit in a cell or vice versa, or evaluation may be incorporated into the training phase itself. Cells may also contain other types of units such as practice units, such as viewing a video or webinar, and different modalities, such as described herein. In still another embodiment, the program may administer further diagnostic testing if needed while the patient is in the therapy phase, before she resumes her therapy.

In yet another embodiment, the disclosed technology may employ interactive games, such as to facilitate movement through at least one of the diagnosis phase and the therapy phase. More particularly, a therapy cell may be in a form of an age-appropriate interactive game, with the game being a shell that can house different content appropriate for each user following error analysis of her responses. For example, the articulation therapy cell, as described herein, may use at least one audio-visual cue in a game to prompt the patient to approximate a target sound or word. Various game rewards or penalties may be included to encourage the patient to reach the prescribed goal. Note that such rewards, which can operated based on a loyalty system, can be redeemable, such as for prizes, cash, goods, services, airline miles, extra therapy sessions, a personal diagnosis and/or therapy session, and so forth.

The first data structure, such as the master matrix, contains a set of inventories of predicted responses to assigned tests and tasks as well as information needed to generate a diagnostic cell and/or a therapy cell. As described herein, the first data structure can be embodied in a computerized database, whether in whole or in part. In other embodiments, the first data structure is embodied among a plurality of databases, whether similar or dissimilar to each other, such as a relational database or a non-relational database, whether hosted remotely and/or locally from each other in any manner, whether directly and/or indirectly. The first data structure is hosted/residing remotely, such as on a server computer, as described herein, instead of a patient's computer, thus allowing more flexibility for end users, such as patients, while providing for more efficient content updates due to such residence/hosting. However, in other embodiments, the first data structure can be hosted/residing locally on the patient's computer, whether in whole or in part, whether directly and/or indirectly. Such configuration can enable a periodic update, such as weekly or monthly, whether in whole or in part, whether directly and/or indirectly from a central data repository, such as a computerized database. For example, in such configuration, the first data structure hosted/residing locally on the patient's computer, whether in whole or in part, is at least a partial copy of the first data structure hosted/residing remotely from the patient's computer.

In some embodiments, the first data structure, contains most, if not all, predicted responses, and feeds data to a computer, as described herein, such as when the first data structure is a database. The computer is configured to direct/generate cell content and shells based on such data feed. The first data structure contains inventories of responses predicted to be made by a given population with language-processing problems, while performing a task based on a diagnostic cell and/or a therapy cell according to the program. If desired, then, the computer initially classifies the incorrect responses into categories, such as phonological, semantic, morphological, or lexical, and sub-classifies, such as morphological>affixes>prefixes, in visual depictions, such as graphs, for instance, a mathematical object comprising a vertex and/or an arc, for storage in the first data structure. The first data structure can also contain phonemes, a lexicon (vocabulary), phrasal and/or sentence patterns as well as other components of a target language needed to generate a diagnostic cell and/or a therapy cell. For example, the target language may be any natural language (i.e., a first language spoken by any group of people in any world region).

Figure 9:
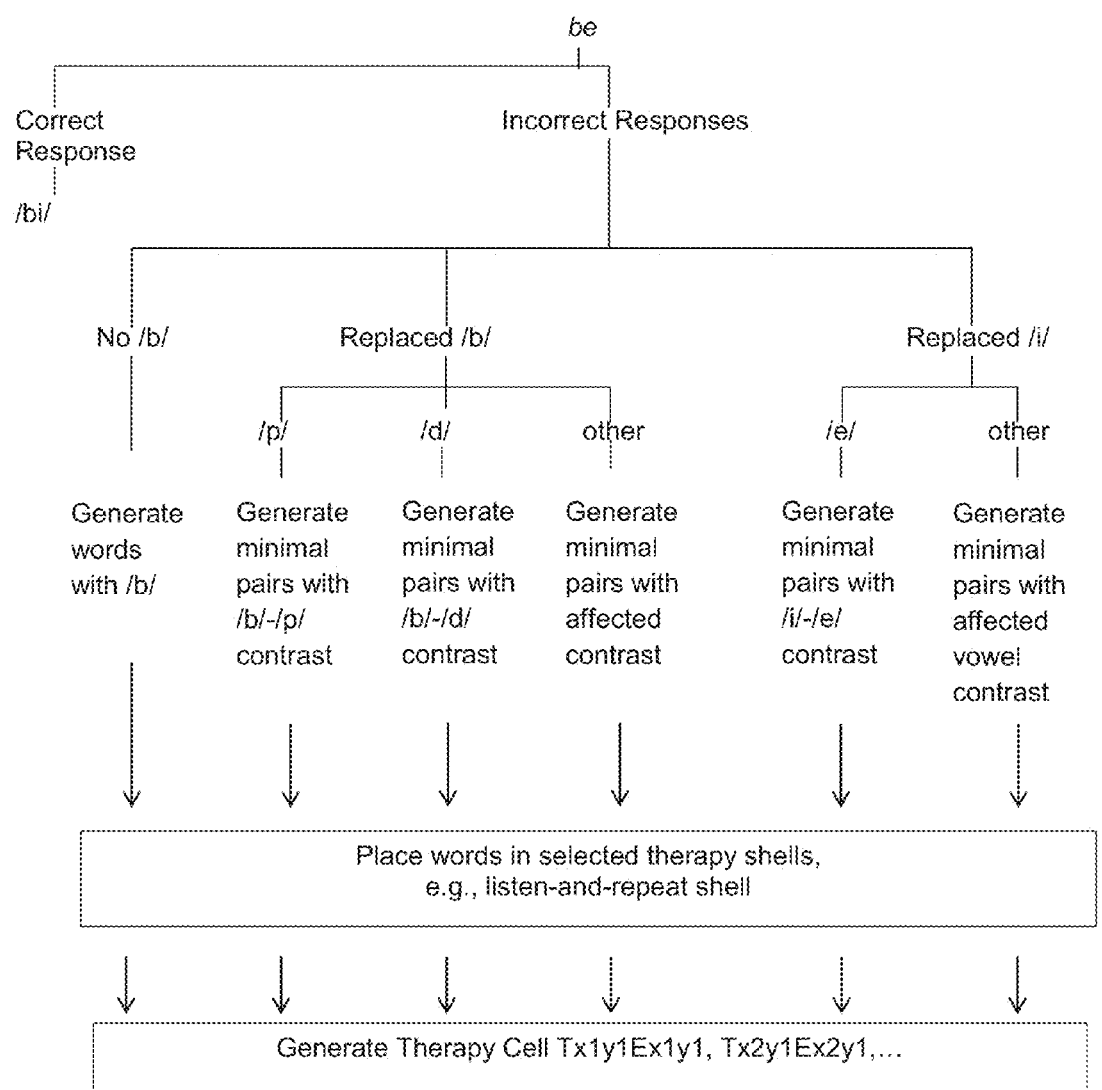
FIG. 9 shows a diagram of an example embodiment of a process for a diagnosis and a therapy according to the present disclosure.

For example, as shown and described in reference to FIG. 9, each stimulus item in a diagnostic cell and/or a therapy cell is represented as a node on a graph, with connected vertices at a next lower level representing most, if not all, possible correct and incorrect responses predicted to be made by a population involved, such as patients with aphasia. The program matches a patient's incorrect response to an identical predicted error (node) in the relevant graph and proceeds down the graph to locate an appropriate set of test and/or practice items to generate a next diagnostic cell and/or a therapy cell. Thus, for an example illustrated in FIG. 9, a stimulus item in the word segmentation diagnostic test is a word be. In such test, the patient has to segment the word into its individual sounds. The corresponding node in the first data structure, such as the master matrix, for this stimulus item is connected to its correct response (/bi/) and predicted incorrect responses. The incorrect responses include most, if not all, possible instances predicted by knowledge of principles and rules of natural languages, linguistics, processes underlying language acquisition or development, as well as processes governing exceptional languages (i.e., language of speakers outside a typical population, such as individuals with communicative disorders). In the case of the stimulus word be, the predicted incorrect responses include instances whereby users omit the consonant /b/ or replace this consonant or the vowel /i/. Knowledge from a set of fields at least identified above helps to predict that, say, if /b/ is replaced, then a likely substituted phoneme is /p/ or /d/ due to their phonetic similarity. The graph also allows for other possible substitutions. Further, a patient's particular incorrect response, such as no /b/, leads to a particular computer operation (Generate words with /b/). The words generated may be real words in the lexicon or nonsense words with the desired sound combinations. When the patient's incorrect response is a substitution error, such as /p/ for /b/, at least one pair of words with the crucial contrast are computer generated, such as minimal pair pit /pɪt/ v. bit /bɪt/). If a patient's response contains more than one error, then most, if not all, the affected nodes on the graph are activated, which means that the patient has to practice with more than one list of words in the therapy phase. When this list of words is placed in the listen-and-repeat therapy shell, then the patient performs a required task by going through each word in such list one by one. Additionally, as a full test usually contains several stimulus items, such test may yield more than one incorrect response from a patient. Thus, several graphs may be activated in the first data structure, such as the master matrix, from one test output. For example, the rapid naming diagnostic test may yield errors involving several words. In such a case, a computer-implemented priority ranking algorithm determines which set of test or practice items to present to the patient next.

The second data structure, such as the patient matrix, is uniquely associated with each patient. As described herein, the second data structure can be embodied in a computerized database, whether in whole or in part. In other embodiments, the second data structure is embodied among a plurality of databases, whether similar or dissimilar to each other, such as a relational database or a non-relational database, whether hosted remotely and/or locally from each other in any manner, whether directly and/or indirectly. The second data structure is hosted/residing remotely, such as on a server computer, as described herein, instead of a patient's computer, thus allowing more flexibility for end users, such as patients, while providing for more efficient content updates due to such residence/hosting. However, note that the server computer can host the first data structure and the second data structure or the first data structure and the second data structure are hosted/reside on different server computers, as described herein. Further, note that, in other embodiments, the second data structure can be hosted/residing locally on the patient's computer, whether in whole or in part, whether directly and/or indirectly. Such configuration can enable a periodic update, such as weekly or monthly, whether in whole or in part, whether directly and/or indirectly from a central data repository, such as a computerized database. For example, in such configuration, the second data structure hosted/residing locally on the patient's computer, whether in whole or in part, is at least a partial copy of the second data structure hosted/residing remotely from the patient's computer. In further embodiments, the first data structure and the second data structure are one data structure, which can be hosted in whole or in part in any way as described herein with reference to at least one of the first data structure and the second data structure individually.

The second data structure stores patient personal information, such as a user identification (ID), a name, a domicile address, a background, whether personal, medical, sociological, ethnic, racial, or others, as well as her responses to diagnostic and evaluation tests. Furthermore, the second data structure can be updated dynamically and automatically, via a computer, whether via a service requester segment, as described herein, or via a service provider segment, as described herein. Such update can occur after each new response from that patient is filtered through the first data structure via the computer. Further, the second data structure contains an inventory of errors and correct responses produced by a particular patient, while performing a task via a diagnostic cell and/or a therapy cell in the program. The patient's errors are classified, via the computer, into categories, such as phonological, semantic, morphological, or lexical, and sub-classified, such as morphological>affixes>prefixes, in graphs in the manner of the first data structure, such as the master matrix.

When a patient's incorrect response is located on a node on one of the graphs in the first data structure, such as the master matrix, the connected vertices at the next lower level of this graph and a computer implemented priority ranking algorithm determine a next diagnostic cell and/or a therapy cell for this patient. The second data structure, such as the patient matrix, is continually updated throughout therapy as the patient makes new errors and/or provides all correct responses for a previously identified problem. The second data structure, such as the patient matrix, is used to track the patient's progress, and the patient may access her progress report in a suitable format, such as a spreadsheet document, a visual depiction document, a word processor document, or any combinations thereof, in real-time. Pertinent information in the second data structure, such as the patient matrix, is sent to the learning analytics database for analysis and monitoring of an efficiency of the program, in whole or in part.

The technology is further enabled via a database storing the patient's correct responses and ill-formed productions based on which a learning analytics computer algorithm or a similar approach is employed to monitor and improve an efficacy of the technology in correcting language-processing deficits. For example, the program's efficacy is enhanced by mining stored patient data using learning analytics or similar approaches such as via the second data structure(s), which contains a lot of useful information, such as patient demographics, common types of errors, for instance, phonological, morphological, lexical, semantic, or syntactic errors, success rates of different therapy cells, and so forth. Efficient data management and retrieval of individual and group information by specified criteria yield useful insight for research and therapy enhancement. Furthermore, the learning analytics data can be stored in a computerized database, as described herein with respect to at least one of the first data structure and the second data structure, or in another computerized database, whether in whole or in part. In other embodiments, the learning analytics data is embodied among a plurality of databases, whether similar or dissimilar to each other, such as a relational database or a non-relational database, whether hosted remotely and/or locally from each other in any manner, whether directly and/or indirectly. The learning analytics data is hosted/residing remotely, such as on a server computer, as described herein, instead of a patient's computer, thus allowing more flexibility for end users, such as patients, while providing for more efficient content updates due to such residence/hosting. However, note that the server computer can host the learning analytics data, the first data structure and the second data structure or the learning analytics data, the first data structure and the second data structure are hosted/reside on different server computers, as described herein. Further, note that, in other embodiments, the learning analytics data can be hosted/residing locally on the patient's computer, whether in whole or in part, whether directly and/or indirectly. Such configuration can enable a periodic update, such as weekly or monthly, whether in whole or in part, whether directly and/or indirectly from a central data repository, such as a computerized database. For example, in such configuration, the learning analytics data hosted/residing locally on the patient's computer, whether in whole or in part, is at least a partial copy of the learning analytics data hosted/residing remotely from the patient's computer. In further embodiments, the learning analytics data, the first data structure and the second data structure are one data structure, which can be hosted in whole or in part in any way as described herein with reference to at least one of the learning analytics data, the first data structure and the second data structure individually.

The learning analytics database can be employed in a backend computer infrastructure that collects and stores most, if not all, results of patient performance history including game play. A computer-implemented learning analytics algorithm running on the backend infrastructure analyzes such results to determine themes, such as a common performance problem or an error, a frequency of live assistance invoked, a frequency of a type of a game played and/or a task performed, a type of game or a task prone to repeated failures, a time of play by time of day and a day of a week, a duration of continuous play, an interval between plays, a frequency with which the patient requested help for assistance, and so forth. Based on such algorithm analysis, changes to the first data structure, such as the master matrix, may be implemented to help enhance a speed and/or an efficiency of patients' progress. Such changes may be implemented with a rapid reboot of a server computer to bring new changes to all patients immediately. Alternatively, such changes may be implemented live, in real-time, without a reboot of the server computer.

Data stored in the learning analytics database may be analyzed by a computer algorithm running on the backend computer infrastructure or viewed by themes or diagrams by a system administrator to identify a trend and/or troubleshoot quickly. Such algorithm may be designed to remotely alert the system administrator of trouble spots via a message, such as an email, a text, a chat, a sound, a vibration, a visual cue, or others, allowing for more rapid or real-time changes to at least one of the service provider or service requester technologies described herein. Similar mechanisms may be deployed to identify particular patients needing immediate or extra attention.

In some embodiments, the disclosed technology enables a computer-implemented error analysis algorithm. More particularly, the program performs the error analysis algorithm via processing a test output through the first data structure against a set of pre-specified, predicted patient responses. For example, for a question asking a patient to identify an affix in a word hunter, the predicted responses comprise 1) -er (correct), 2) hunt (incorrect), 3) none (incorrect), 4) hunter (incorrect), or 5) other (incorrect). Therefore, the error analysis algorithm entails an analysis of learners' errors using knowledge of structures and processes (principles and rules) of natural languages to identify patterns of errors and trace sources of errors as problems arise. As described herein, such error analysis algorithm is used to compare the patient's actual responses to a set of targeted correct responses. For example, an error analysis of a patient's productions may reveal that she consistently fails to recognize common affixes such as -er (hunt<u>er</u>), -or (edit <u>or</u>), and -tion (act<u>ion</u>). In this case, a result of the analysis algorithm is based at least in part on a word formation process (morphological); but such error analysis can cover any component of language (phonological, semantic, lexical, syntactic) and can be based on any defined dimension. Note that the error analysis algorithm can be run on the backend computer infrastructure. Further, note that the error analysis algorithm is adopted from a field of second language acquisition.

In some embodiments, the disclosed technology enables a computer-implemented priority ranking algorithm. More particularly, most, if not all, category and/or item in the first data structure, such as the master matrix, is assigned a weighted value based on a frequency of occurrence in a language, a communicative function, a significance of impact from its omission or ill-formedness, and so forth. This value determines which diagnostic or therapy item or cell will be presented next. The priority ranking algorithm would select the article the over the adjective unimportant since the former occurs more frequently than the latter. Note that the priority ranking algorithm can be run on the backend computer infrastructure.

In some embodiments, the disclosed technology enables a live assistant functionality. More particularly, if a patient is unable to pass a cell's evaluation test after several tries, such as two, or if the patient produces responses that are not predicted via a content of the first data structure, then a live assistant may step in to help the patient proceed to a next stage. For example, such live assistance takes a form of an automated program with an advanced speech recognition, a human-computer interaction, and/or a communicative capability. Alternatively, such live assistance takes a form of a communication with a live human operator, such as in a call center. For example, such communication can comprise a telephone communication, a teleconference, a chat, or a personal visit, such as when the disclosed technology is embodied in an office-lab setting.

In some embodiments, for ease of accessibility, the present disclosure enables patient diagnosis and/or patient therapy from an internet-based website or an online portal and runs the program on a cloud server. However, such delivery method can be complemented and/or supplemented, in whole or in part, via a mobile app, as described herein. One convenience of such deployment a relatively simple maintenance of a patient's profile and allowance of an easy access to her diagnosis and/or therapy program through a network. Note that different apps may be developed for different therapy shells (tasks). Further, note that such deployment may allow a temporary halt and resumption of at least one of diagnosis and therapy. Therefore, such functionality can be utilized over periods of time, such as over several months.

In some embodiments, the present disclosure enables multiple modalities. More particularly, diagnostic and/or therapy cells may use any or a combination of modalities including video, audio, text, graphics, animation, web conferencing, or others enabled by new technologies. Patient may employ electronic and/or physical supports, such as self-facing or rear-facing cameras during speech articulation practices, and other future technologies. The program may also employ voice and/or speech recognition software to train as well as to receive and analyze input from patients. Biometric monitoring and feedback may be incorporated to increase the program's sensitivity to patients' performance and responses, and thus the program's efficacy. This may be particularly useful for those with attention deficits. Sensing systems may be installed with the program to collect biometric data, which may include eye gaze (to monitor focus of attention), pulse and blinking rates (to monitor stress and mental fatigue), and lip movements (to monitor articulation). Such sensors may provide biometric feedback to the program as well as to the patient. When the patient receives such information as instantaneous feedback, the program—especially if delivered unobtrusively on a wearable or other portable device—can become seamlessly integrated into her daily life. In this embodiment, the program may provide real-time corrections to her language errors as she commits them in her daily functions.

In some embodiments, the present disclosure enables a performance trail/patient's performance history. More particularly, the program not only stores the patient's correct and incorrect responses in the second data structure, such as the patient matrix, but displays in an easily accessible format her scores from all previously completed diagnostic and therapy cells. The patient's progress report may be updated continually as she completes each cell. The program may display a comparison of the patient's performance history and the projected prescribed path of development. This visual display encourages the patient to keep working towards her prescribed goal—a satisfactory removal of all language-processing problems identified.

In some embodiments, the present disclosure enables a reward system. More particularly, a diagnostic test, an evaluation test, and/or a training practice may be delivered as age-appropriate interactive games. The patient's performance for each part may be scored and converted to reward points that the patient can trade for virtual or physical objects, earned time for multiplayer games or such like, or other forms of incentives to motivate the patient to put in the effort to complete her training satisfactorily. Note that such rewards, which can be operated based on a loyalty system, can be redeemable, such as for prizes, cash, goods, services, airline miles, extra therapy sessions, personal diagnosis and/or therapy session, and so forth.

FIG. 1 shows a schematic view of an example embodiment of a computer network model according to the present disclosure. A computer network model 100 comprises a network 102, a server 104, and a client 106. Such distributed operation model allocates tasks/workloads between the server 104, which provides a resource/service, and the client 106, which requests the resource/service. The server 104 and the client 106 illustrate different computers/applications, but in other embodiments, the server 104 and the client 106 reside in one system/application. Further, in some embodiments, the model 100 entails allocating a large number of resources to a small number of computers, such as the servers 104, where complexity of the client 106 depends on how much computation is offloaded to the number of computers, i.e., more computation offloaded from the clients 106 onto the servers 104 leads to lighter clients 106, such as being more reliant on network sources and less reliant on local computing resources.

The network 102 includes a plurality of nodes, such as a collection of computers and/or other hardware interconnected via a plurality of communication channels, which allow for sharing of resources and/or information. Such interconnection can be direct and/or indirect. The network 102 can be wired and/or wireless. The network 102 can allow for communication over short and/or long distances, whether encrypted and/or unencrypted. The network 102 can operate via at least one network protocol, such as Ethernet, a Transmission Control Protocol (TCP)/Internet Protocol (IP), and so forth. The network 102 can have any scale, such as a personal area network, a local area network, a home area network, a storage area network, a campus area network, a backbone network, a metropolitan area network, a wide area network, an enterprise private network, a virtual private network, a virtual network, a satellite network, a computer cloud network, an internetwork, a cellular network, and so forth. The network 102 can be and/or include an intranet and/or an extranet. The network 102 can be and/or include Internet. The network 102 can include other networks and/or allow for communication with other networks, whether sub-networks and/or distinct networks, whether identical and/or different from the network 102. The network 102 can include hardware, such as a computer, a network interface card, a repeater, a hub, a bridge, a switch, an extender, and/or a firewall, whether hardware based and/or software based. The network 102 can be operated, directly and/or indirectly, by and/or on behalf of one and/or more entities, irrespective of any relation to contents of the present disclosure.

The server 104 can be hardware-based and/or software-based. The server 104 is and/or is hosted on, whether directly and/or indirectly, a server computer, whether stationary or mobile, such as a kiosk, a workstation, a vehicle, whether land, marine, or aerial, a desktop, a laptop, a tablet, a mobile phone, a mainframe, a supercomputer, a server farm, and so forth. The server computer can be touchscreen enabled and/or non-touchscreen. The server computer can include and/or be a part of another computer system and/or a cloud computing network. The server computer can run any type of operating system (OS), such as iOS®, Windows®, Android®, Unix®, Linux® and/or others. The server computer can include and/or be coupled to, whether directly and/or indirectly, an input device, such as a mouse, a keyboard, a camera, whether forward-facing and/or back-facing, an accelerometer, a touchscreen, a biometric reader, a clicker, and/or a microphone. The server computer can include and/or be coupled to, whether directly and/or indirectly, an output device, such as a display, a speaker, a headphone, a joystick, a videogame controller, a vibrator, and/or a printer. In some embodiments, the input device and the output device can be embodied in one unit. The server computer can include circuitry for global positioning determination, such as via a global positioning system (GPS), a signal triangulation system, and so forth. The server computer can be equipped with near-field-communication (NFC) circuitry. The server computer can host, run, and/or be coupled to, whether directly and/or indirectly, a database, such as a relational database or a non-relational database, which can feed data to the server 104, whether directly and/or indirectly.

The server 104, via the server computer, is in communication with the network 102, such as directly and/or indirectly, selectively and/or unselectively, encrypted and/or unencrypted, wired and/or wireless, via contact and/or contactless. Such communication can be via a software application, a software module, a mobile app, a browser, a browser extension, an OS, and/or any combination thereof. For example, such communication can be via a common framework/application programming interface (API), such as Hypertext Transfer Protocol Secure (HTTPS).

The client 106 can be hardware-based and/or software-based. The client 106 is and/or is hosted on, whether directly and/or indirectly, a patient computer, whether stationary or mobile, such as a terminal, a kiosk, a workstation, a vehicle, whether land, marine, or aerial, a desktop, a laptop, a tablet, a mobile phone, a mainframe, a supercomputer, a server farm, and so forth. The patient computer can be touchscreen enabled and/or non-touchscreen. The patient computer can include and/or be a part of another computer system and/or cloud computing network. The patient computer can run any type of OS, such as iOS®, Windows®, Android®, Unix®, Linux® and/or others. The patient computer can include and/or be coupled to an input device, such as a mouse, a keyboard, a camera, whether forward-facing and/or back-facing, an accelerometer, a touchscreen, a biometric reader, a clicker, and/or a microphone, and/or an output device, such as a display, a speaker, a headphone, a joystick, a videogame controller, a vibrator, and/or a printer. In some embodiments, the input device and the output device can be embodied in one unit. The patient computer can include circuitry for global positioning determination, such as via a GPS, a signal triangulation system, and so forth. The patient computer can be equipped with NFC circuitry. The patient computer can host, run and/or be coupled to, whether directly and/or indirectly, a database, such as a relational database or a non-relational database, which can feed data to the patient 106, whether directly and/or indirectly.

The client 106, via the patient computer, is in communication with network 102, such as directly and/or indirectly, selectively and/or unselectively, encrypted and/or unencrypted, wired and/or wireless, via contact and/or contactless. Such communication can be via a software application, a software module, a mobile app, a browser, a browser extension, an OS, and/or any combination thereof. For example, such communication can be via a common framework/API, such as HTTPS.

In other embodiments, the server 104 and the client 106 can also directly communicate with each other, such as when hosted in one system or when in local proximity to each other, such as via a short range wireless communication protocol, such as infrared or Bluetooth®. Such direct communication can be selective and/or unselective, encrypted and/or unencrypted, wired and/or wireless, via contact and/or contactless. Since many of the clients 106 can initiate sessions with the server 104 relatively simultaneously, in some embodiments, the server 104 employs load-balancing technologies and/or failover technologies for operational efficiency, continuity, and/or redundancy.

Note that other computing models are possible as well. For example, such models can comprise decentralized computing, such as peer-to-peer (P2P), for instance Bit-Torrent®, or distributed computing, such as via a computer cluster where a set of networked computers works together such that the computer can be viewed as a single system.

Figure 2:
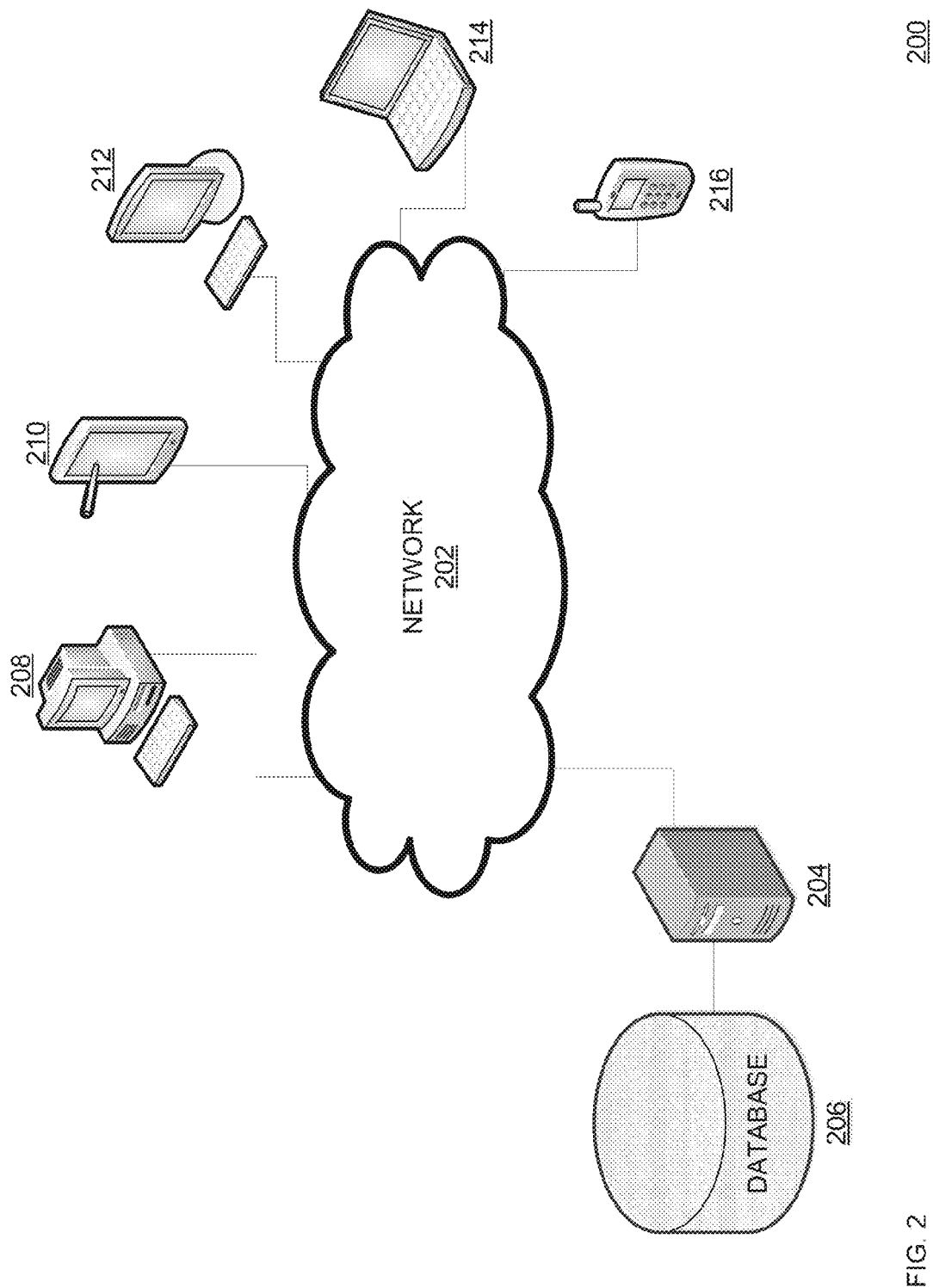
FIG. 2 shows a schematic view of an example embodiment of a computer network architecture according to the present disclosure.

FIG. 2 shows a schematic view of an example embodiment of a computer network architecture according to the present disclosure. A computer network architecture 200 comprises a network 202 in communication with a service provider segment and with a service requester segment. The service provider segment comprises a server computer 204 and a database 206. The service requester segment comprises a workstation computer 208, a tablet computer 210, a desktop computer 212, a laptop computer 214, and a mobile phone 216. The architecture 200 operates according to the model 100. However, in other embodiments, the architecture 200 operates according to other computing models, as described herein, such as direct communication, decentralized computing, distributed computing, and/or any combinations thereof. The network 202 operates according to the network 102. However, in other embodiments, the network 202 operates according to other network types, as described herein.

Note that the service provider segment can comprise more than one server computer 204 and/or more than one database 206, whether structurally and/or functionally identical and/or different from each other, whether communicatively coupled to each other and/or not communicatively coupled to each other, such as directly and/or indirectly, wired and/or wireless, selectively and/or unselectively, encrypted and/or unencrypted, via contact and/or contactless, whether synchronous and/or asynchronous, whether controlled via a single entity and/or via a plurality of entities, irrespective of any relation to contents of the present disclosure. Likewise, note that the service requester segment can comprise less than five and/or more than five computers 208, 210, 212, 214, 216 whether structurally and/or functionally identical and/or different from each other, whether communicatively coupled to each other and/or not communicatively coupled to each other, such as directly and/or indirectly, wired and/or wireless, selectively and/or unselectively, encrypted and/or unencrypted, via contact and/or contactless, whether synchronous and/or asynchronous, whether controlled via a single entity and/or via a plurality of entities, irrespective of any relation to contents of the present disclosure.

The computer 204 is in communication with the network 202, such as directly and/or indirectly, wired and/or wireless, selectively and/or unselectively, encrypted and/or unencrypted, via contact and/or contactless, whether synchronous and/or asynchronous. The computer 204 facilitates such communication via a hardware unit, such as a hardware component of the computer 204, for example, a network card. However, in other embodiments, the computer 204 facilitates such communication via a software unit, such as a software application, a software module, a mobile app, a browser, a browser extension, an OS, and/or any combination thereof. For example, such communication can be via a common framework/API, such as HTTPS. Due to a size of the service requester segment, the computer 204 employs load-balancing technologies and/or failover technologies for operational efficiency, continuity, and/or redundancy.

The computer 204 is operably coupled to the database 206 such that the computer 204 is in communication with the database 206, such as directly and/or indirectly, wired and/or wireless, selectively and/or unselectively, encrypted and/or unencrypted. The computer 204 facilitates such communication via a hardware unit, as a hardware component of the computer 204, for example, a network card. However, in other embodiments, the computer 204 facilitates such communication via a software unit, such as a software application, a software module, a mobile app, a browser, a browser extension, an OS, and/or any combination thereof. For example, such communication can be via a common framework/API, such as HTTPS, employed via a database management system (DBMS) hosted on the computer 204, such as MySQL®, Oracle®, or other suitable systems. Also, note that the computer 204 can host the database 206 locally and/or access the database 206 remotely. Alternatively, the computer 204 and the database 206 can be in one locale, yet distinctly embodied. Further, note that the computer 204 can host and/or be operably coupled to more than one database 206, such as directly and/or indirectly, wired and/or wireless, selectively and/or unselectively, encrypted and/or unencrypted, via contact and/or contactless, whether synchronous and/or asynchronous. Also, note that the database 206 can be hosted on more than one computer 204, such as directly and/or indirectly, wired and/or wireless, selectively and/or unselectively, encrypted and/or unencrypted, via contact and/or contactless, whether synchronous and/or asynchronous.

The database 206 comprises an organized collection of data. The data can be of any type, whether a primitive type, such as a Boolean and/or a character, a composite type, such as an array and/or a union, and/or an abstract data type, such as a list, a queue, a deck, a stack, a string, a tree, and/or a graph. The data can be organized of any structure, such as a linear structure, such as an array, a map, a table, a matrix, a vector, and/or a list, a tree structure, such as a tree, a pagoda, a treap, a heap, and/or a trie, a hash structure, such as a table, a list, and/or a filter, a graph structure, such as a graph, a matrix, a stack, and/or a diagram, and/or any combinations of any thereof. The organized collection of data can contain content, such as patient information, language-related disorder shell information, language-related disorder cell information, patient matrix information, master matrix information, analytics information, and/or other relevant information. The database 206 is accessed via the computer 204, such as via the DBMS running on the computer 206. The database 206 is a relational database, but other database models are possible, such as post-relational. Note that although the computer 204 and the database 206 are distinctly positioned from each other, in other embodiments, the computer 204 hosts the database 206. Note that the computer 204 and the database 206 are operated via a single actor, but in other embodiments, the computer 204 and the database 206 are operated via different actors. Further, note that the database 206 can be in communication with the network 202 such that the computer 204 communicates with the database 206 via the network 202.

The workstation computer 208, the tablet computer 210, the desktop computer 212, the laptop computer 214, and the mobile phone 216 are in communication with the network 202, such as directly and/or indirectly, wired and/or wireless, selectively and/or unselectively, encrypted and/or unencrypted, synchronous and/or asynchronous, on-demand and/or non-on-demand. In any combinatory manner, the workstation computer 208, the tablet computer 210, the desktop computer 212, the laptop computer 214, and the mobile phone 216 facilitate such communication via a hardware unit, such as a hardware component of the workstation computer 208, the tablet 210, the desktop computer 212, the laptop computer 214, and the mobile phone 216, for example, a transceiver and/or a network card. In other embodiments, the workstation computer 208, the tablet computer 210, the desktop computer 212, the laptop computer 214, and the mobile phone 216 facilitate such communication via a software unit, such as a software application, a software module, a mobile app, a browser, a browser extension, an OS, and/or any combination thereof. For example, such communication can be via a common framework/API, such as HTTPS. Further, note that other types of service requesters are possible, such as a standalone camera, an automated teller machine (ATM), a crypto-currency miner, a kiosk, a terminal, a wearable computer, such as an eyewear computer, an implanted computer, or other suitable computing devices.

Note that at least two of the workstation computer 208, the tablet computer 210, the desktop computer 212, the laptop computer 214, and the mobile phone 216 can communicate via the network 202 concurrently and/or non-concurrently, in an identical manner and/or in a different matter. Further, note that the workstation computer 208, the tablet computer 210, the desktop computer 212, the laptop computer 214, and the mobile phone 216 are operated via different actors, but in other embodiments, at least two of the workstation computer 208, the tablet 210, the desktop computer 212, the laptop computer 214, and the mobile phone 216 are operated via a single actor.

The service provider segment serves data via the network 202 to the service requester segment. Such serving can be via push technology and/or pull technology. For example, the push technology enables request initiation via the service provider segment, such as via the computer 204. Resultantly, periodically updateable information can be pushed via the computer 204, such as via synchronous conferencing, messaging, and/or file distribution, onto the service requester segment. Also, for example, the pull technology enables request initiation via the service requester segment, such as via the mobile phone 216. Resultantly, information can be pulled via the mobile phone 216, such as via web browsing, and/or web feeding, from the service provider segment.

In one mode of operation, language-related disorder diagnosis data and/or therapy data based thereon is provided via the service provider segment to the service requester segment via the network 202. For example, the computer 204 feeds the diagnosis data and/or the therapy data from the database 206 onto the mobile phone 216, on-demand, as operated via a language-related disorder patient. The computer 204 receives patient responses from the mobile phone 216 and processes such responses dynamically and iteratively for more granular diagnosis and/or therapy. An operator of the computer 204 and/or the database 206 can control how such feeding takes place, such as via patient subscription, and/or update the diagnosis data and/or the therapy data, such as based on data obtained iteratively from other language-related disorder patients dynamically.

Figure 3:
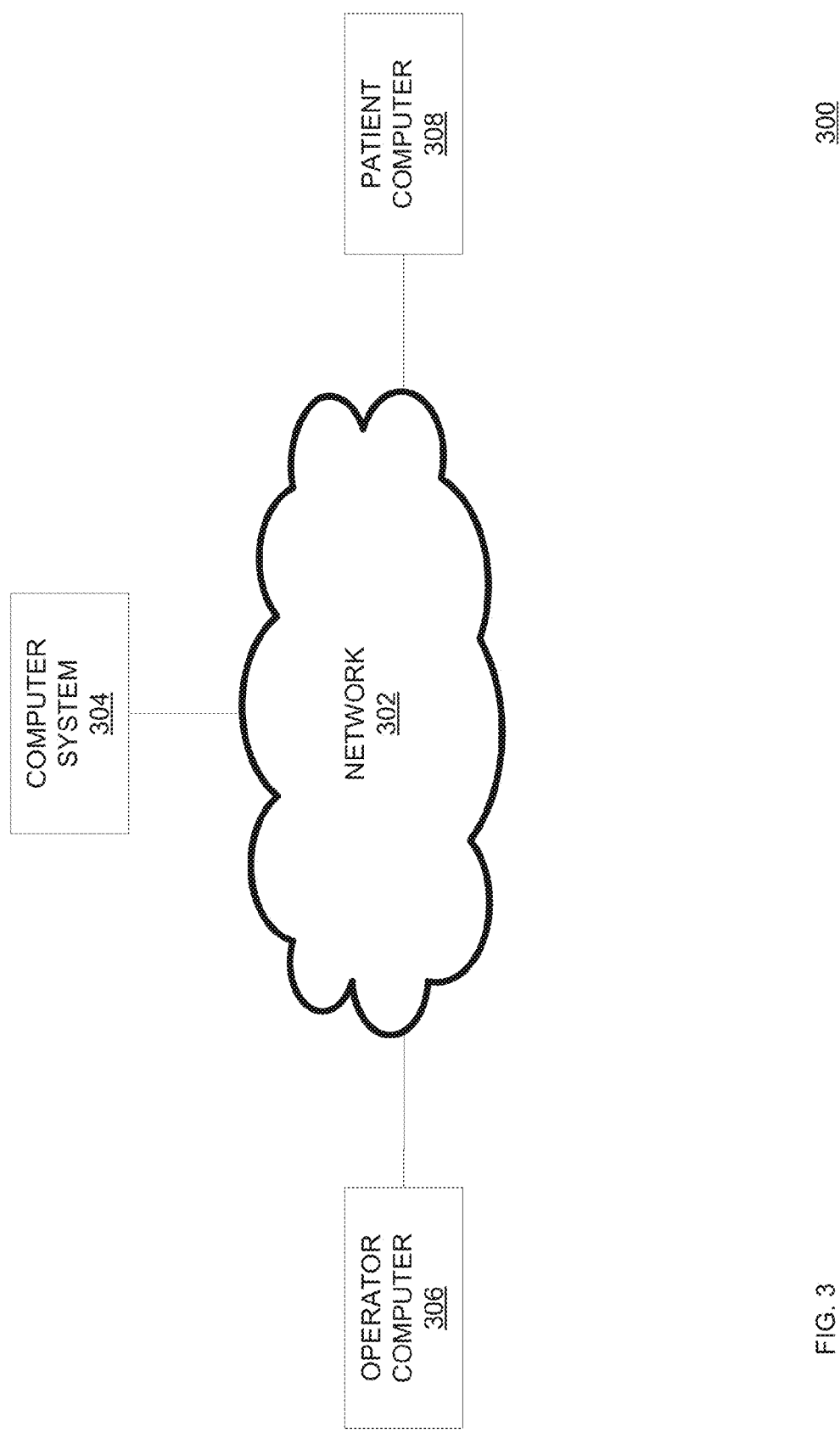
FIG. 3 shows a schematic view of an example embodiment of a computer network diagram according to the present disclosure.

FIG. 3 shows a schematic view of an example embodiment of a computer network diagram according to the present disclosure. A computer network diagram 300 comprises a network 302, a computer system 304, an operator computer 306, and a patient computer 308. The network 302 operates according to the network 202, but other network types are possible, as described herein. The service provider segment comprises the system 304, which functions as a network-based telemedicine service, such as for network-based language-related disorder diagnosis and/or therapy. The system 304 is in communication with the network 302, as described herein. The operator computer 308, such as at least one of the workstation computer 208, the tablet computer 210, the desktop computer 212, the laptop computer 214, and the mobile phone 216, is able to communicate with the system 304, such as for control of how such feeding takes place, such as via patient subscription, and/or update the diagnosis data and/or the therapy data, such as based on data obtained iteratively from other language-related disorder patients dynamically. The service requester segment comprises the patient computer 308, such as at least one of the workstation computer 208, the tablet computer 210, the desktop computer 212, the laptop computer 214, and the mobile phone 216. In another embodiment, the operator computer 306 and the patient computer 308 are a single computer. The operator computer 306 and the patient computer 308 are in communication with the network 302, as described herein. Further, the operator computer 306 can be configured for providing the live assistance functionality, whether in whole or in part, to the patient computer 308, whether directly or indirectly, such as via a telephone call, a teleconference, a chat, or others.

Figure 4:
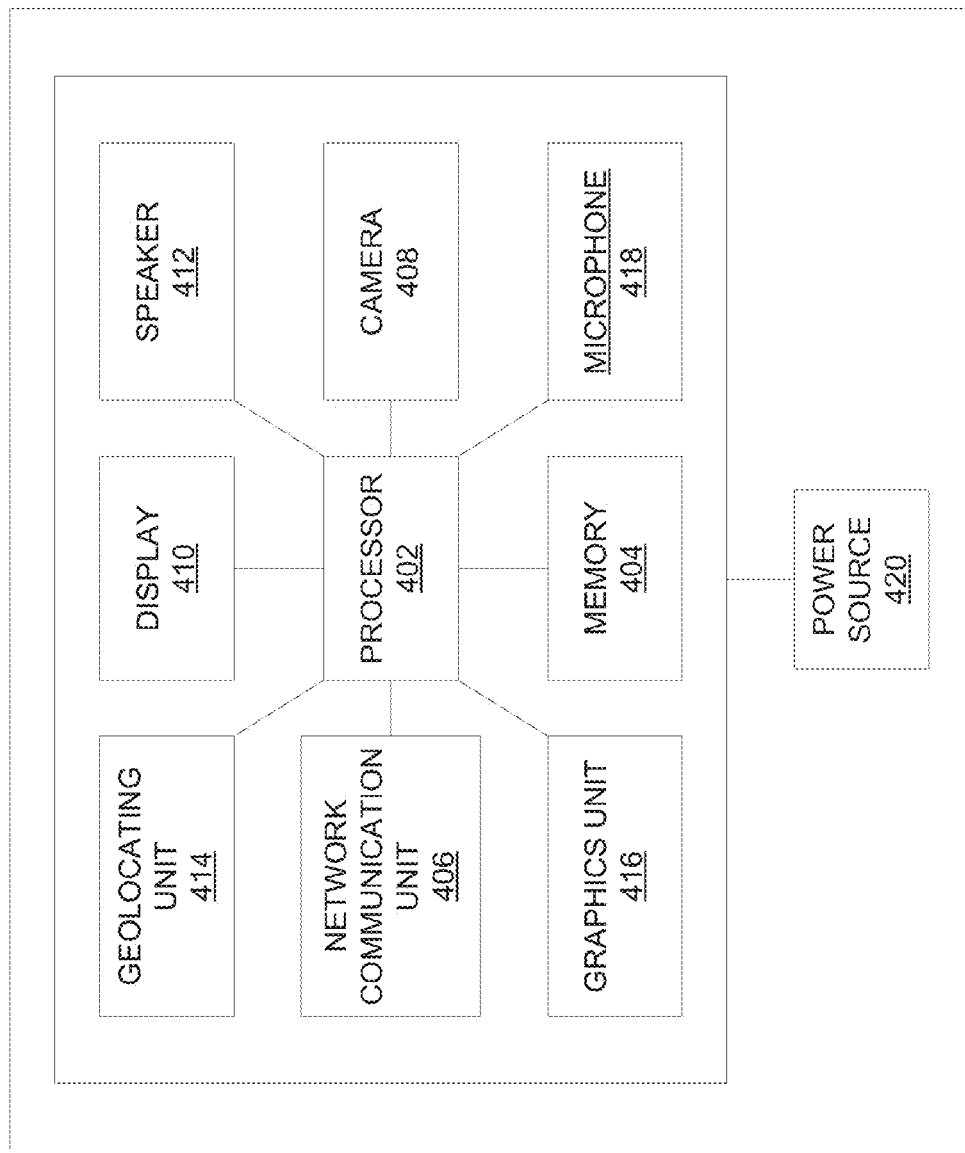
FIG. 4 shows a schematic view of an example embodiment of a computer according to the present disclosure.

FIG. 4 shows a schematic view of an example embodiment of a computer according to the present disclosure. A computer 400 comprises a processor 402, a memory 404 operably coupled to the processor 402, a network communication unit 406 operably coupled to the processor 402, a camera 408 operably coupled to the processor 402, a display 410 operably coupled to the processor 402, a speaker 412 operably coupled to the processor 402, a geolocating unit 414 operably coupled to the processor 402, a graphics unit 416 operably coupled to the processor 402, and a microphone 418 operably coupled to the processor 402. The computer 400 comprises a power source 420, which powers the processor 402, the memory 404, the network communication unit 406, the camera 408, the display 410, the speaker 412, the geolocating unit 414, the graphics unit 416, and the microphone 418. Although at least two of the processor 402, the memory 404, the network communication unit 406, the camera 408, the display 410, the speaker 412, the geolocating unit 414, the graphics unit 416, the microphone 418, and power source 420 are embodied in one unit, at least one of the processor 402, the memory 404, the network communication unit 406, the camera 408, the display 410, the speaker 412, the geolocating unit 414, the graphics unit 416, the microphone 418, and power source 420 can be operably coupled to the computer 400 when standalone, such as locally or remotely, directly or indirectly. Further, in other embodiments, the computer 400 lacks at least one of the network communication unit 406, the camera 408, the display 410, the speaker 412, the geolocating unit 414, the graphics unit 416, and the microphone 418. Note that the computer 400 can comprise other units, whether an input unit and/or an output unit, such as a biometric reader, a clicker, a vibrator, a printer, and so forth.

The processor 402 comprises a hardware processor, such as a multicore processor. For example, the processor 402 comprises a central processing unit (CPU).

The memory 404 comprises a computer-readable storage medium, which can be non-transitory. The medium stores a plurality of computer-readable instructions, such as a software application, for execution via the processor 402. The instructions instruct the processor 402 to facilitate performance of a method for diagnosis and/or therapy of language-related disorder, as described herein. Some examples of the memory 404 comprise a volatile memory unit, such as random access memory (RAM), or a non-volatile memory unit, such as a hard disk drive or a read only memory (ROM). For example, the memory 404 comprises flash memory. The memory 404 is in wired communication with the processor 402. Also, for example, the memory 402 stores a plurality of computer-readable instructions, such as a plurality of instruction sets, for operating at least one of the network communication unit 406, the camera 408, the display 410, the speaker 412, the geolocating unit 414, the graphics unit 416, the microphone 418, or other input and/or output units.

The network communication unit 406 comprises a network interface controller for computer network communication, whether wired or wireless, direct or indirect. For example, the network communication unit 406 comprises hardware for computer networking communication based on at least one standard selected from a set of Institute of Electrical and Electronics Engineers (IEEE) 802 standards, such as an IEEE 802.11 standard. For instance, the network communication unit 406 comprises a wireless network card operative according to a IEEE 802.11(g) standard. The network communication unit 406 is in wired communication with the processor 402.

The camera 408 comprises a lens for image capturing, such as a photo and/or a video. The camera 408 stores captured visual information on the memory 404, which can be in a compressed format or an uncompressed format. The camera 408 can allow image display on the display 410, such as before, during and/or after image capture. The camera 408 can comprise a flash illumination unit. The camera 408 can allow for zooming, whether optical or software based. The camera 408 is in wired communication with the processor 402. The camera 408 can also be remotely coupled to the processor 402, such as wirelessly.

The display 410 comprises an area for displaying visual and/or tactile information. The display 410 comprises at least one of an electronic visual display, a flat panel display, a liquid crystal display (LCD), and a volumetric display. For example, the display 410 comprises a touch-enabled computer monitor. The display 410 is in wired communication with the processor 402. The display 410 can also be remotely coupled to the processor 402, such as wirelessly.

The speaker 412 comprises a loudspeaker, such as an electroacoustic transducer providing sound responsive to an electrical audio signal input. For example, the speaker 412 is a dynamic speaker. The speaker 412 is in wired communication with the processor 402. The speaker 412 can also be remotely coupled to the processor 402, such as wirelessly.

The geolocating unit 414 comprises a GPS receiver. The geolocating unit 414 is in communication with the processor 402. Note that other types of geolocation are possible, such as via cell site signal triangulation. The geolocating unit 414 can also be remotely coupled to the processor 402, such as wirelessly.

The graphics unit 416 comprises a graphics processing unit (GPU) for image processing. The graphics unit 416 is a graphics dedicated unit, but in other embodiments, the processor 402 is integrated with the graphics unit 416. For example, the graphics unit 416 comprises a video card. The graphics unit 416 is in wired communication with the processing unit 402.

The microphone 418 comprises an acoustic-to-electric transducer/sensor operative to convert sound in air into an electrical signal for subsequent use, such as output via the speaker 412. The microphone 418 can be electromagnetic induction based, capacitance change based, or piezoelectric based. The microphone 418 can be coupled to a preamplifier upstream from an audio power amplifier. For example, the microphone 418 is a dynamic microphone. The microphone 418 can also be remotely coupled to the processor 402, such as wirelessly.

The power source 420 powers the computer 400. The power source 420 comprises at least one of an onboard rechargeable battery, such as a lithium-ion battery, and an onboard renewable energy source, such as a photovoltaic cell, a wind turbine, and/or a hydropower turbine. Note that such power can be via mains electricity, such as via a power cable.

Note that the computer 400 can also include and/or be operably coupled to at least one input device, such as a computer keyboard, a computer mouse, a touchpad, a clicker, a scanner, a fax, a biometric reader, a pointer, or other suitable input devices. Likewise, the computer 400 can include and/or be operably coupled to at least one output device, such as a printer, a projector, or other suitable output devices. Further, at least one of the computer 204, the workstation computer 208, the tablet 210, the desktop computer 212, the laptop computer 214, and the mobile phone 216 can be built according to the computer 400 schematic.

Figure 5:
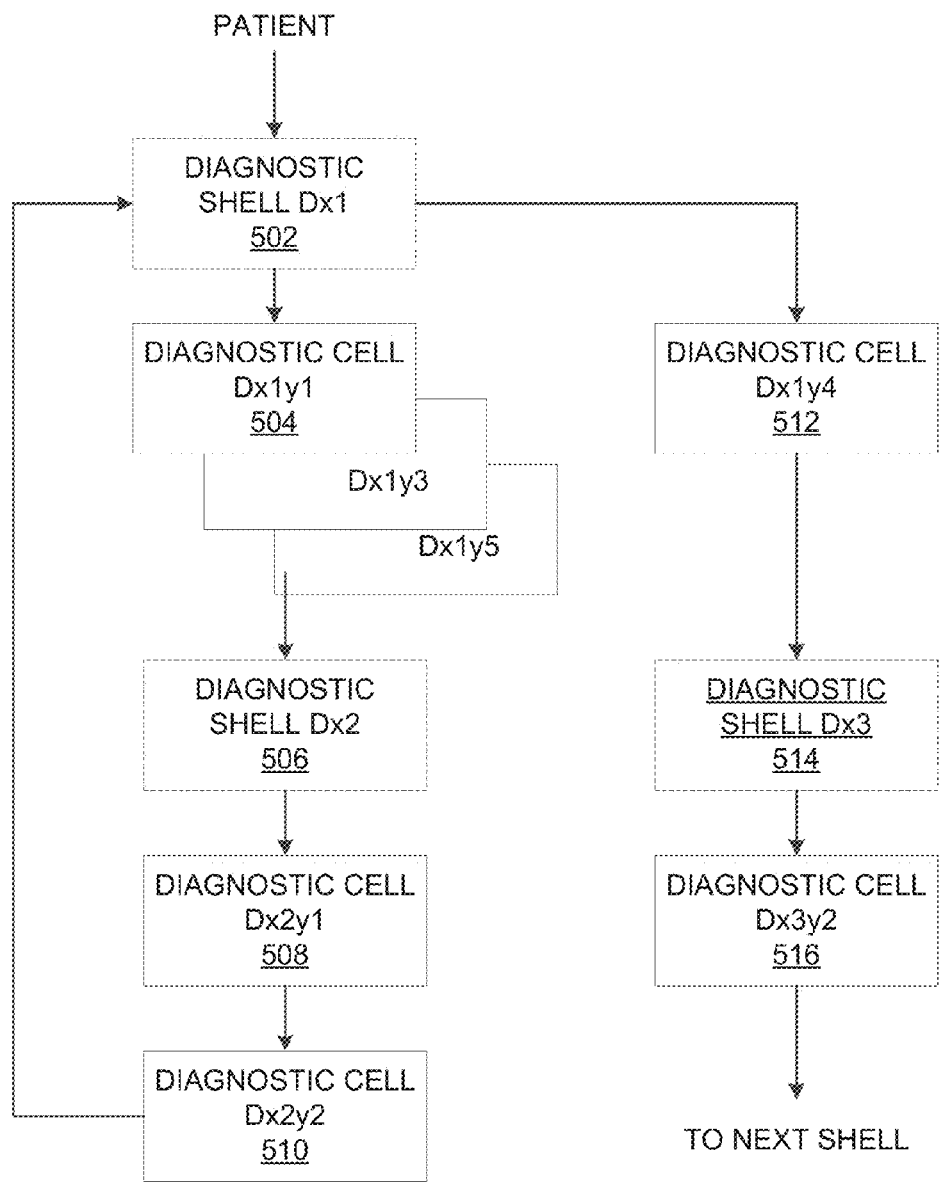
FIG. 5 shows a flowchart of an example embodiment of a process for diagnosis based on a generative model according to the present disclosure.

FIG. 5 shows a flowchart of an example embodiment of a process for diagnosis based on a generative model according to the present disclosure. The process, as computer implemented via at least one of the service provider segment and the service requester segment, employs a plurality of diagnosis shells 502, 506, 514. The process further employs a plurality of diagnosis cells 504, 508, 510, 512, 516. Note that any number of shells or cells can be used in any combinatory manner. The process, based on which the program can operate, employs the first data structure, such as the master matrix, and patient information in the second data structure, such as the patient matrix, to select a first diagnostic shell 502 ($Dx_1$, represented by dotted rectangle) to activate. Each diagnostic shell specifies a particular task to be performed by the patient, such as matching sounds to letters or symbols. From the diagnostic shell 502 ($Dx_1$), the program generates at least one content-specific test cell 504 (Diagnostic Cells $Dx_1y_{1-n}$) by inserting selected information from the first data structure, such as the master matrix, into the shell 502. Note that such computerized generation can be concurrent, simultaneous, real-time, contemporaneous, batch-processed, multithreaded, or any negatives thereof, such as non-concurrent, non-simultaneous, and so forth. For example, if the diagnostic shell $Dx_1$ specifies a task of naming objects shown on a computer display, then particular diagnostic cells $Dx_1y_1$, $Dx_1y_3$, $Dx_1y_5$ and so forth may involve a naming of a different category of objects each, such as household objects, tools, or things whose names begin with the letter "B." The cells 504 are administered to the patient in an order that is optimal, such as most efficacious, for this particular patient, based on a set of specified criteria in the first data structure, such as the master matrix. The cells 504 may be administered in a non-sequential order because the present disclosure does not necessarily prescribe a pre-set sequence for diagnosis and therapy.

Further, $Dx_1y_1$ is followed by $Dx_1y_3$ and $Dx_1y_5$. This does not necessarily mean that $Dx_1y_1$, $Dx_1y_3$, and $Dx_1y_5$ are pre-defined cells with pre-defined content provided in a pre-defined order. Rather, such cells are generated following an analysis of each patient's results. As such, the process may deploy a different set of diagnostic cells from that same diagnostic shell for another patient, a different sequence of those same set of cells, or skip such shell altogether depending on an at least one underlying language problem identified.

Further, the process enables a generation of the diagnostic cells 504 ($Dx_1y_1$, $Dx_1y_3$, $Dx_1y_5$) all together, but the patient takes such tests consecutively in an order dynamically set via the first data structure, such as the master matrix. The patient's responses based on the cells 504 enable an automatic selection of the diagnostic shell 506 ($Dx_2$) to generate a next test in the cell 508 ($Dx_2y_1$). The patient's responses to the cell 508 ($Dx_2y_1$) leads to an automatic generation of yet another cell 510 ($Dx_2y_2$) for further testing. The patient's results for the cell 510 ($Dx_2y_2$) then enables the process to automatically return to selecting the shell 502 again for further, more granular testing, but this time with new content retrieved from the first data structure, such as the master matrix, to generate the diagnostic cell 512 ($Dx_1y_4$). Based on her results, the patient then proceeds to the next diagnostic shell 514 ($Dx_3$) and then the cell 516 ($Dx_3y_2$) in an order dynamically set via the first data structure, such as the master matrix.

Figure 6:
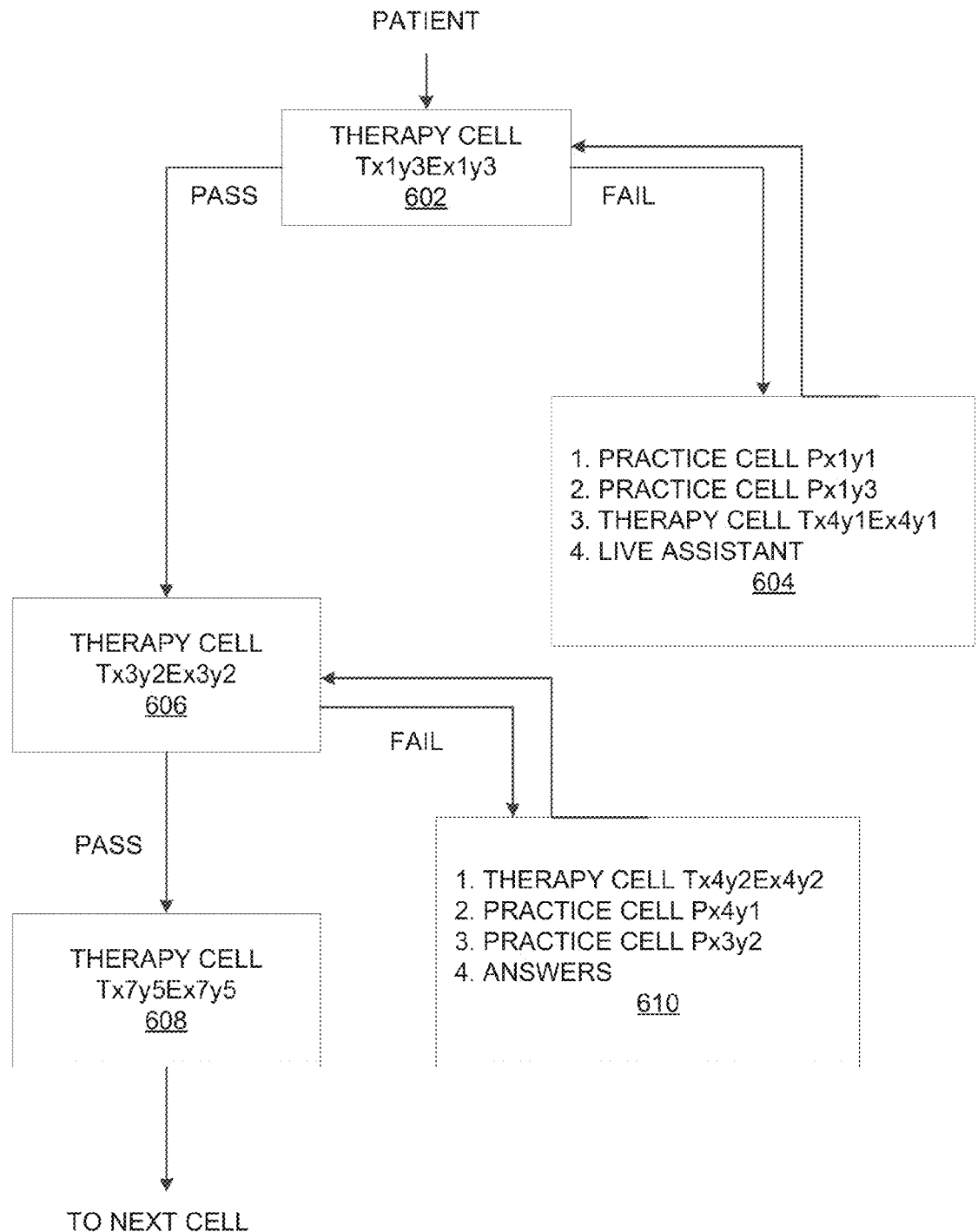
FIG. 6 shows a flowchart of an example embodiment of a process for therapy based on a generative model according to the present disclosure.

FIG. 6 shows a flowchart of an example embodiment of a process for therapy based on a generative model according to the present disclosure. Each shell in the therapy phase contains a training unit ($Tx_{1-n}$) and an evaluation unit ($Ex_{1-n}$). The process, based on which the program can execute, initially uses the patient's performance history from the diagnostic phase, as contained in the second data structure, such as the patient matrix, to generate a therapy cell for therapy based at least in part on a therapy shell via comparing, analyzing, or filtering the second data structure, such as the patient matrix, against the first data structure, such as the master matrix. The patient's performance on earlier therapy cells then determines subsequent cells to be administered as information is continually updated in the second data structure, such as the patient matrix. The cells in the therapy phase are generated from their corresponding shells in a same or similar manner such as in the diagnostic phase. Note that any number of shells or cells can be used.

As shown in FIG. 6, the process captures a portion of the therapy phase for one patient. Such process can be computer implemented via at least one of the service provider segment and the service requester segment. At a stage of the process illustrated, the therapy cell 602 ($Tx_1y_3Ex_1y_3$) is administered, such as via a computer architecture in FIGS. 1-4. To proceed to a next cell, the patient is obliged to pass an evaluation contained in this cell 602 according to a criteria specified by the first data structure, such as the master matrix. If the patient passes, then the process continues onto a generation of a next cell 606 ($Tx_3y_2Ex_3y_2$) from the shell $Tx_3Ex_3$ via again retrieving selected content from the first data structure, such as the master matrix. However, if the patient fails to pass the evaluation of cell 602 ($Tx_1y_3Ex_1y_3$), then the process, as per block 604, generates a practice cell ($Px_1y_1$) to help the patient build up a needed skill to pass. Repeated failures entail more practice cells ($Px_1y_3$) or other therapy cells ($Tx_4y_1Ex_4y_1$). Other therapy cells ($Tx_4y_1Ex_4y_1$) may be deployed to help this patient build up the skill needed to pass the original therapy cell ($Tx_1y_3Ex_1y_3$). If the patient still fails to pass that same cell $Tx_1y_3Ex_1y_3$ after several attempts, such as two, then live assistance functionality, as described herein, is invoked.

The patient proceeds to the generated therapy cell 606 ($Tx_3y_2Ex_3y_2$) upon successfully performing tasks based on the cell 602, as evaluated against the second data structure, such as the patient matrix. Similarly, if the patient passes, then the patient proceeds to the next cell generated, which is cell 608. However, if the patient fails, then a similar process, as with a cycle involving the cell 602 ($Tx_1y_3Ex_1y_3$) occurs. However, different cycles of failures with different cells may entail different types of cells and different sequences of their presentation. For example in FIG. 6, with the first cycle of failures involving cell 602 ($Tx_1y_3Ex_1y_3$), two practice cells ($Px_1y_1$, $Px_1y_3$) were administered before another therapy cell ($Tx_4y_1Ex_4y_1$). Although the process may deploy similar or different types of practice cells to aid the patient, depending on the problems identified. with the second cycle of failures involving cell 606 ($Tx_3y_2Ex_3y_2$), as per block 610, a therapy cell ($Tx_4y_2Ex_4y_2$) was administered before practice cells. However, the cell 608 is administered upon successful passing of a task based on the cell 606. In some cases, as appropriate, at least some answers are provided before the patient attempts a same evaluation one last time prior to proceeding to the next therapy cell. However, in other cases, instructional videos or other aids may be provided following failed attempts as appropriate. Further, as the process goes on, the patient's responses are recorded in the second data structure, such as the patient matrix, as the patient goes through new therapy cells. Based on such recordation, the process enables a modification and augmentation of the patient's therapy, continually updating a type and an order of cells to activate next based on information from the first data structure, such as the master matrix. At least one of the diagnostic phase and the therapy phase is thus based on a responsive, generative model for a creation of an individualized diagnostic and therapy cells for each patient.

Figure 7:
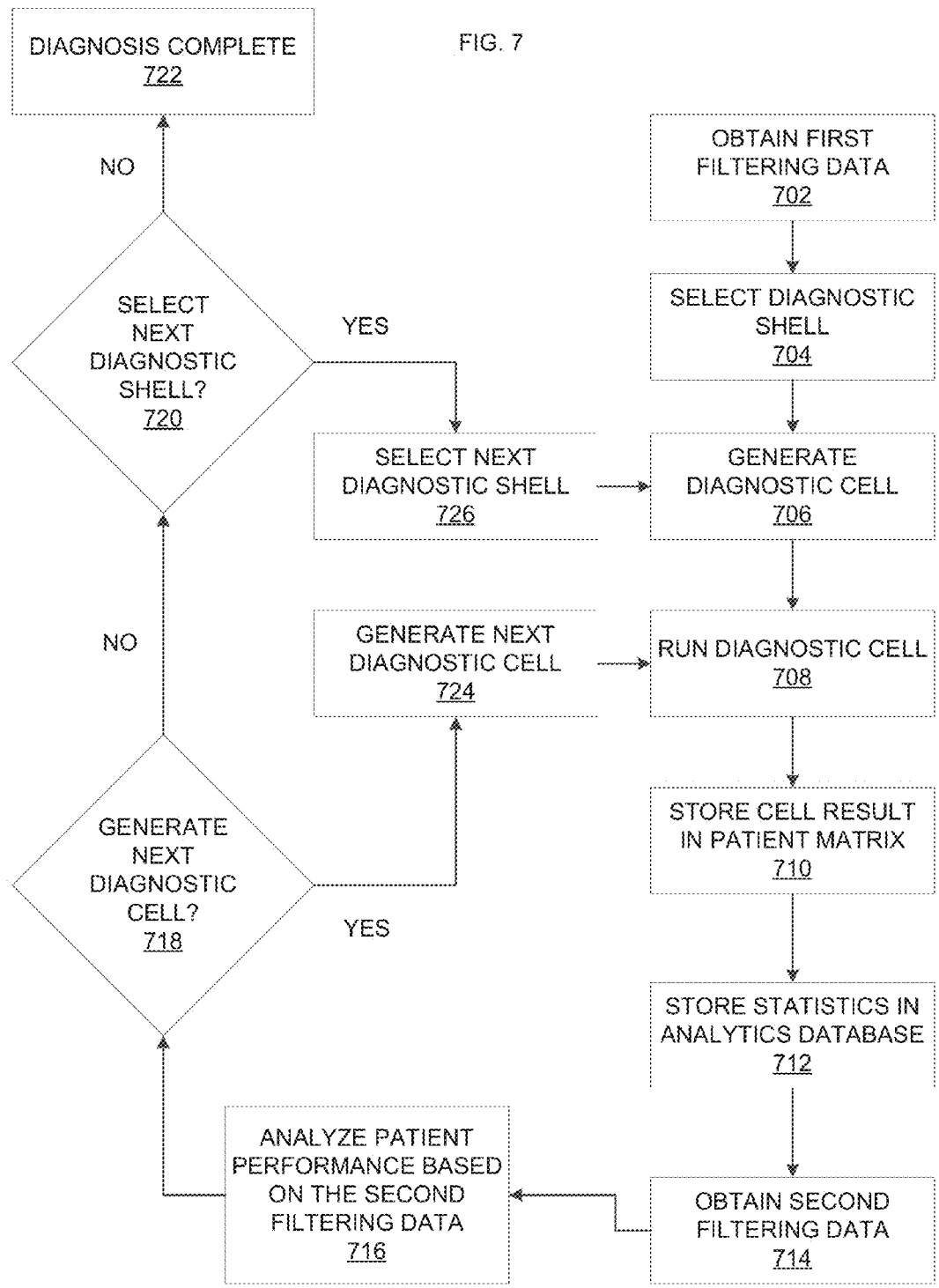
FIG. 7 shows a flowchart of an example embodiment of a process for diagnosis according to the present disclosure.

FIG. 7 shows a flowchart of an example embodiment of a process for diagnosis according to the present disclosure. Such process comprises at least a plurality of blocks 702-726. Further, such process can be performed in sequential numerical order and/or non-sequential numerical order. The process is performed via a computing architecture, as described herein, such as in FIGS. 1-4. Whether domestically and/or internationally, the process can be performed, facilitated for performance, and/or assisted in such performance via at least one actor, such as the service provider segment. For example, such process can be performed via the computer system 304 interfacing with the patient computer 308.

In block 702, the system 304 obtains first filtering data, such as via comparing, analyzing, or filtering the second data structure, such as the patient matrix, against the first data structure, such as the master matrix.

In block 704, the system 304 selects a diagnostic shell based at least in part on the first filtering data from block 702.

In block 706, the system 304 generates a diagnostic cell based at least in part on the diagnostic shell from block 704.

In block 708, the system 304 runs the diagnostic cell selected in block 706. Such run can comprise interfacing with the patient computer 308, such as via network communication with the patient computer 308. The patient computer 308 runs the diagnostic cell to receive patient input.

In block 710, the system 304 stores a result of the diagnostic cell in the second data structure, such as the patient matrix. Such storage, which can be dynamic, is based at least in part on receiving at least some of the patient input from the patient computer 308, whether in real-time or in a delayed manner.

In block 712, the system 304 stores statistics in an analytics data structure, such as a computerized database. Such storage, which can be dynamic, is based at least in part on obtaining the statistics from the result, as stored in the second data structure. Alternatively, the statistics can be obtained based at least in part on receiving at least some of the patient input from the patient computer 308, whether in real-time or in a delayed manner.

In block 714, the system 304 obtains second filtering data, such as via comparing, analyzing, or filtering the second data structure, such as the patient matrix, as updated in block 710, against the first data structure, such as the master matrix.

In block 716, the system 304 analyzes patient performance based at least in part on the second filtering data from block 714. Such analysis enables a determination if another diagnostic cell using that same shell, from block 704, is needed. Further, such analysis is based at least in part on factors, as described herein.

In block 718, the system 304 makes a decision as to whether a generation of a next diagnostic cell should take place. If yes, the process continues onto block 724. Otherwise, the process continues onto block 720.

In block 720, the system 304 makes a decision as to whether a selection of a next diagnostic shell should take place. If yes, the process continues onto block 726. Otherwise, the process continues onto block 722.

In block 722, the system 304 determines that patient diagnosis is complete. Such determination can comprise an output to the patient computer 308. For example, such output can be visual, auditory, vibratory, or other.

In block 724, the system 304 generates a next diagnostic cell based at least in part on the diagnostic shell from block 704. Note that a content of such cell is generated based on the first data structure, such as the master matrix.

In block 726, the system 304 selects a next diagnostic shell for activation. Note that this process goes through as many cycles as needed until information from the first data structure and the second data structure indicates that the diagnostic testing phase is complete for this patient, where the process can optionally continue onto the therapy phase. Further, note that since most steps are performed via the system 304, the patient computer 308 is light on resources for other background tasks. Note that the diagnosis phase can be paused or resumed via the patient at any time.

Figure 8:
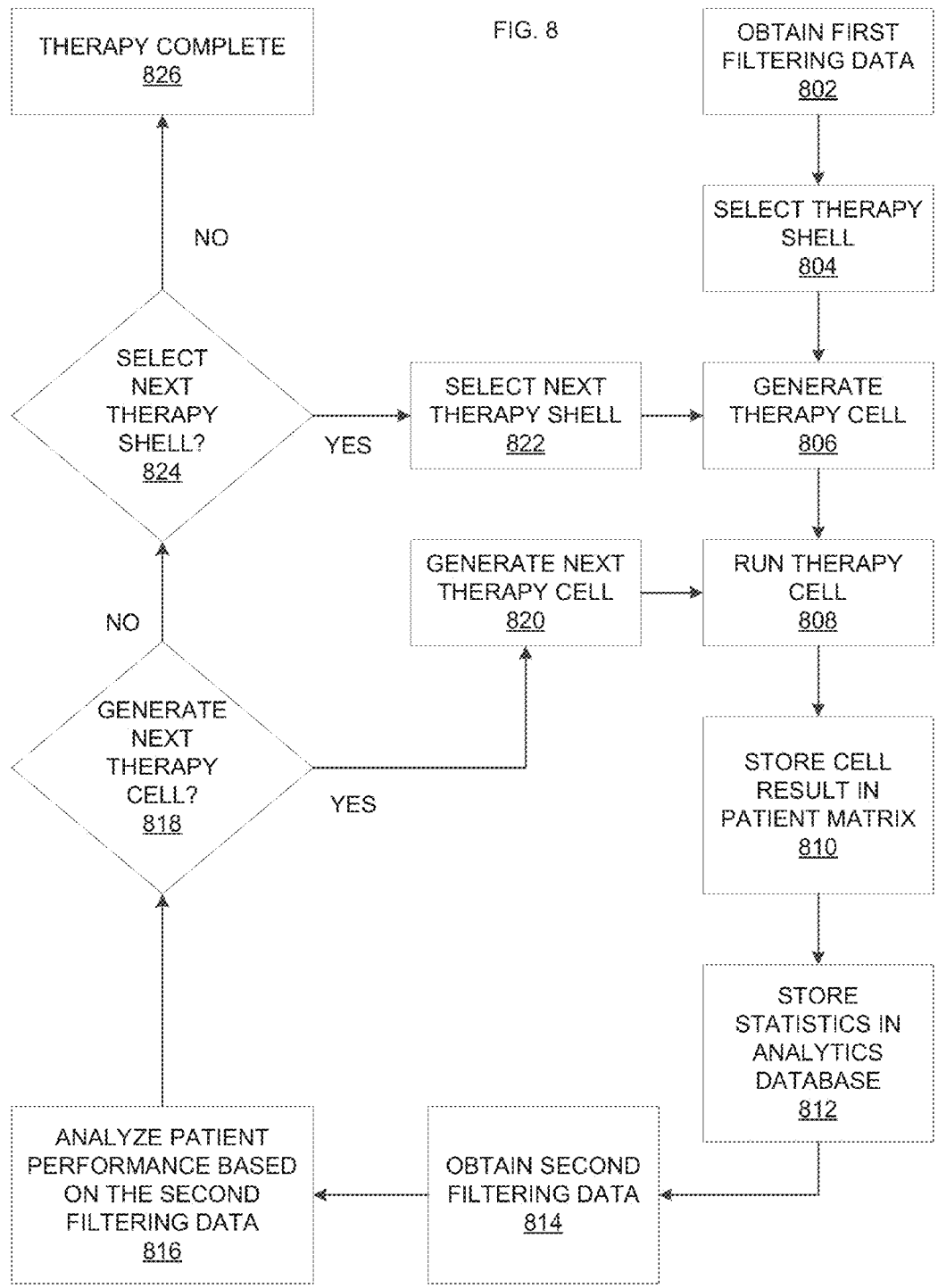
FIG. 8 shows a flowchart of an example embodiment of a process for therapy according to the present disclosure.

FIG. 8 shows a flowchart of an example embodiment of a process for therapy according to the present disclosure. Such process comprises at least a plurality of blocks 802-826. Further, such process can be performed in sequential numerical order and/or non-sequential numerical order. The process is performed via a computing architecture, as described herein, such as in FIGS. 1-4. Whether domestically and/or internationally, the process can be performed, facilitated for performance, and/or assisted in such performance via at least one actor, such as the service provider segment. For example, such process can be performed via the computer system 304 interfacing with the patient computer 308.

In block 802, the system 304 obtains first filtering data, such as via comparing, analyzing, or filtering the second data structure, such as the patient matrix, against the first data structure, such as the master matrix.

In block 804, the system 304 selects a therapy shell based at least in part on the first filtering data from block 802.

In block 806, the system 304 generates a therapy cell based at least in part on the therapy shell from block 804.

In block 808, the system 304 runs the therapy cell selected in block 806. Such run can comprise interfacing with the patient computer 308, such as via network communication with the patient computer 308. The patient computer 308 runs the therapy cell to receive patient input. For example, such therapy cell can be $Tx_i y_j Ex_i y_j$.

In block 810, the system 304 stores a result of the therapy cell in the second data structure, such as the patient matrix. Such storage, which can be dynamic, is based at least in part on receiving at least some of the patient input from the patient computer 308, whether in real-time or in a delayed manner.

In block 812, the system 304 stores statistics in an analytics data structure, such as a computerized database. Such storage, which can be dynamic, is based at least in part on obtaining the statistics from the result, as stored in the second data structure. Alternatively, the statistics can be obtained based at least in part on receiving at least some of the patient input from the patient computer 308, whether in real-time or in a delayed manner.

In block 814, the system 304 obtains second filtering data, such as via comparing, analyzing, or filtering the second data structure, such as the patient matrix, as updated in block 810, against the first data structure, such as the master matrix.

In block 816, the system 304 analyzes patient performance based at least in part on the second filtering data from block 814. Such analysis enables a determination if another therapy cell using that same shell, from block 804, is needed. Further, such analysis is based at least in part on factors, as described herein. Note that both new and previous information entered into the second data structure is compared, analyzed, or filtered through the first data structure to determine if another therapy cell using same shell $Tx_i Ex_i$, as per block 804, is needed.

In block 818, the system 304 makes a decision as to whether a generation of a next therapy cell should take place. If yes, the process continues onto block 820. Otherwise, the process continues onto block 824.

In block 824, the system 304 makes a decision as to whether a selection of a next therapy shell should take place. If yes, the process continues onto block 822. Otherwise, the process continues onto block 826.

In block 820, the system 304 generates a next therapy cell based at least in part on the therapy shell from block 804. Note that a content of such cell is generated based on the first data structure, such as the master matrix.

In block 822, the system 304 selects a next therapy shell for activation. Note that this process goes through as many cycles as needed until information from the first data structure and the second data structure indicates that the therapy phase is complete for this patient. Further, note that since most steps are performed via the system 304, the patient computer 308 is light on resources for other background tasks.

In block 826, the system 304 determines that patient therapy is complete, at least for one therapy session or one therapy act. Such determination can comprise an output to the patient computer 308. For example, such output can be visual, auditory, vibratory, or other. Note that the therapy phase can be paused or resumed via the patient at any time.

FIG. 9 shows a diagram of an example embodiment of diagnosis and therapy according to the present disclosure. A stimulus item in the word segmentation diagnostic test is a word be. In such test, the patient has to segment the word into its individual sounds. The corresponding node in the first data structure, such as the master matrix, for this stimulus item is connected to its correct response (/bi/) and predicted incorrect responses. The incorrect responses include most, if not all, possible instances predicted by knowledge of principles and rules of natural languages, linguistics, processes underlying language acquisition or development, as well as processes governing exceptional languages (i.e., language of speakers outside a typical population, such as individuals with communicative disorders). In the case of the stimulus word be, the predicted incorrect responses include instances whereby users omit the consonant /b/ or replace this consonant or the vowel /i/. Knowledge from a set of fields at least identified above helps to predict that, say, if /b/ is replaced, then a likely substituted phoneme is /p/ or /d/ due to their phonetic similarity. The graph also allows for other possible substitutions. Further, a patient's particular incorrect response, such as no /b/, leads to a particular computer operation (Generate words with /b/). The words generated may be real words in the lexicon or nonsense words with the desired sound combinations. When the patient's incorrect response is a substitution error, such as /p/ for /b/, at least one pair of words with the crucial contrast are computer generated, such as minimal pair pit /pɪt/ v. bit /bɪt/. If a patient's response contains more than one error, then most, if not all, the affected nodes on the graph are activated, which means that the patient has to practice with more than one list of words in the therapy phase. When this list of words is placed in the listen-and-repeat therapy shell, then the patient performs a required task by going through each word in such list one by one. Additionally, as a full test usually contains several stimulus items, such test may yield more than one incorrect response from a patient. Thus, several graphs may be activated in the first data structure, such as the master matrix, from one test output. For example, the rapid naming diagnostic test may yield errors involving several words. In such a case, a computer-implemented priority ranking algorithm determines which set of test or practice items to present to the patient next.

Figure 10:
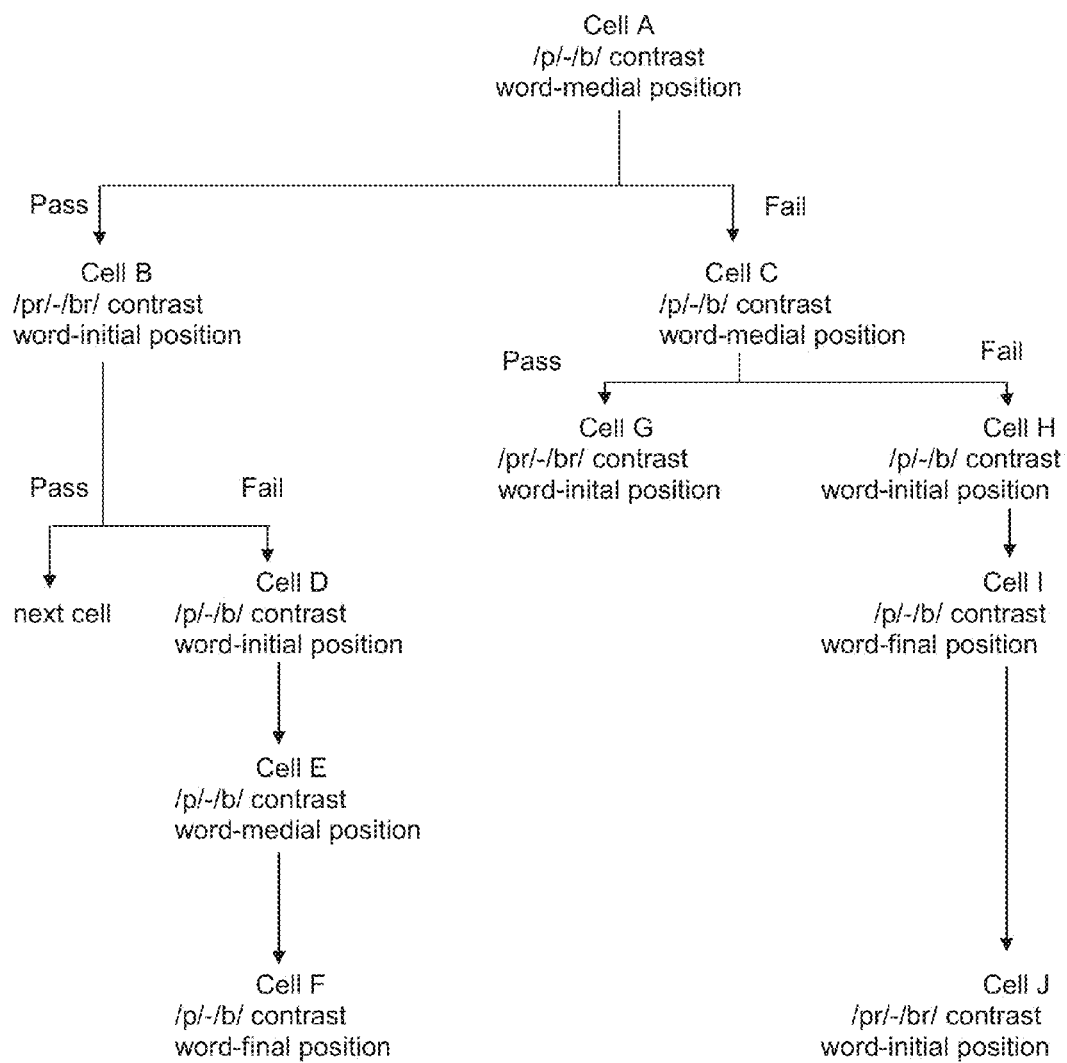
FIG. 10 shows a diagram of an example embodiment of a phoneme identification diagnostic shell and cells for consonants according to the present disclosure.

FIG. 10 shows a diagram of an example embodiment of a phoneme identification diagnostic shell and cells for consonants according to the present disclosure. Such methodology is implemented via the technology described herein.

In one mode of operation, such as based on the computing architecture of FIGS. 1-4, the diagnostic phase is structured to provide a comprehensive profile of the patient's ability to process linguistic information as a speaker, listener, reader, and writer. The underlying structure is designed to allow the patient to move methodically through most, if not all, language components important in performing such roles, with built-in mechanisms to confirm evaluation accuracy. For example, the process starts with the phoneme identification diagnostic shell. The first phoneme identification diagnostic cell generated, cell A, tests patient's ability to distinguish /p/ from /b/ in the word-medial position, such as shown in FIG. 10. The phonemes /p/ and /b/ are distinguished from each other by a phonetic feature of voicing. Pairs of words that are distinguished by just one phonetic feature are called minimal pairs, such as staple and stable. When the phoneme identification diagnostic cell A is administered with the /p/-/b/ contrast, the patient hears strings of words containing /p/ or /b/ in a random order, such as staple, clamber, or flappy. The patient is asked to pick out only words that have /p/. If the patient makes no error in this cell, then the process generates a next cell B with the /pr/-/br/ contrast in word-initial position, such as prim, or brim. If the patient makes no error again, then the process proceeds onto a next phonemic contrast in a sequence, which is /t/-/d/. If the patient commits errors in cell B, then the process generates cells D-F to test her ability to distinguish /p/-/b/ in the word-initial position and the word-final position as well as confirm at least one previous error in word-medial position.

If the patient commits errors in cell A, then the process generates a next cell C with the /p/-/b/ contrast in a word-medial position again to confirm the errors in cell A. From cell C, if the patient commits no error, then the process enables generation of cell G to test her ability to distinguish /pr/-/br/ in the word-initial position. Cells B and G both test the same /pr/-/br/ contrast in word-initial position but are labeled differently to indicate the patient's different paths through the process and to underscore the fact that the process generates each cell with different content because the if patient commits error in cell C, then the process first generates cells H and I containing the /p/-/b/ contrast in the word-initial and the word-final positions before generating cell J with the /pr/-/br/ contrast in the word-initial position. One reason for presenting the word-medial contrast before word-initial is because the former is expected to be more difficult to detect than the latter. Therefore, if the patient can perform a harder task first, then an easier task need not necessarily be administered.

Other contrasts relevant to the phoneme /p/ can be included in the same manner as described above, such as /p/-/t/ (pip, tip), /p/-/f/ (pit, fit), /p/-/k/ (pick, kick) and /p/ v. Ø (keep, key). Consonant clusters such as /pl/-/bl/ (plume, bloom), /pr/-/tr/ (prick, trick), /spl/-/sl/ (splay, slay), both in word-initial and word-final positions can similarly be incorporated into the diagnostic phase through more diagnostic cells.

Note that phoneme identification tasks may incorporate a measuring of processing speed. In such a case, the rapid processing diagnostic shell is used. The phoneme identification task remains as described above, but now the patient performs under a time limit. For example, the patient auditory detects phonemic contrasts at a normally rapid speed of natural speech. If the patient fails to detect most contrasts at this speed, then those same tasks are given at slower speed, such as 60-80 words per minute. A distinct discrepancy between her performances at normal and slow speeds would point to a problem with processing speed.

The process is further uniquely structured to ensure efficiency, rendering an order of presentation of the diagnostic cells important. Finer contrasts are tested before more obvious ones. For example, the patient is only tested on the /o/-/au/contrast (hole, howl) if she fails the /o/-/ɔ/ contrast (h<u>o</u>le, h<u>a</u>ll) because a patient who can detect the latter is likely to be able to detect the former as well and thus need not be necessarily tested on the easier contrast.

Most, if not all, results from the diagnostic cells are recorded in the second data structure, such as the patient matrix, for generation of therapy cells later. This part of the diagnosis phase covers most, if not all, phonemes and phoneme clusters in a language. At an end of such diagnosis, the process yields a substantial, if not complete, phonological profile of the patient that specifies which phonemes and phoneme clusters are problematic in which sound environments.

Diagnostic cells can also be incorporated in the therapy phase. For example, more complicated consonant clusters, such as /spr/-/skr/, can be tested at an end of the therapy phase for /p/ to see if there are still lingering problems with this phoneme.

From the phoneme identification diagnostic shell, the process can proceed to the sound-symbol matching diagnostic shell. The process can use a result of the phoneme identification diagnostic cells to generate the cells for sound-symbol matching. For example, if the patient made errors with the /v/-/w/ contrast in the phoneme identification shell, then the process can generate sound-symbol matching cells that ask the patient to input, such as via typing, letters that match recorded sounds /v/ and /w/. Thus, sound-symbol matching cells can be used to confirm the results of the phoneme identification cells administered earlier.

From the phoneme identification diagnostic shell, the process can separately proceed to syllabification diagnostic shell and onto the word segmentation diagnostic shell. From a sound found to be problematic for the patient from the earlier phoneme identification testing, any words containing these particular phonemes can be generated in the syllabification diagnostic cells. For example, if the patient produced errors in the phoneme identification cells involving /p/ in word-medial and word-final positions, then the syllabification diagnostic cell may include the word harpsichord to see if the patient retains the /p/ sound in breaking this word into its syllables. If the patient omits the /p/, then the subsequent word segmentation diagnostic cell can include more words with /p/ in these positions, such as mishaps and capsized. The patient is then asked to segment these words into individual sounds, giving finer detail of her phonemic ability. In performing these tasks in syllabification and word segmentation shells, new errors may trigger the program to run the phoneme identification cells again for phonemes that were not initially found to be problematic in certain sound environments.

Other kinds of phonological tests can also be administered from phoneme identification, including rhyming. Particularly when the patient commits errors with vowels in the phoneme identification shell, the process can generate rhyming diagnostic cells, such as asking the patient to produce words that rhyme with /iɘ/ when she failed to detect the /i ɘ/-/i/ contrasted earlier in the phoneme identification shell, such as b<u>eer</u> v. b<u>ee</u>). To perform this task, she may record her words using a microphone, type, or select pairs of words that rhyme.

From sound-symbol matching, the diagnosis phase can proceed onto word-level tests such as lexical access and lexical retrieval. If the results of the phoneme identification and sound-symbol matching diagnoses suggest that the patient faces difficulty processing the phoneme /b/ in certain sound environments, then the process can generate lexical access diagnostic cells that ask her to produce, either by recording or typing, as many words as possible with the /b/ sound in word-initial, word-medial, or word-final position within a set time. The process first scores a number of words she can produce within a time limit to determine if accessing words with /b/ is problematic in and of itself. The process then matches her productions against stored words to detect further problems and obtain additional details about her processing difficulties. For example, if she misspells blubber as blummer, then such error confirms that she has difficulty with the /b/-/m/ contrast in the word-medial position. However, if she spells bubble correctly in a same task, then this result would suggest that her problem may be confined to the /b/-/m/ contrast in word-medial position only when the word ends with /r/. In short, subsequent diagnostic cells in the process can confirm and yield finer details about the patient's processing problems.

The lexical retrieval diagnostic shell can follow from or precede the lexical access shell. When following the lexical access shell, the lexical retrieval diagnostic cells can be used to trace in finer detail the parts of the patient's mental lexicon (network of stored words in the brain) that have been adversely affected by processing difficulties at a phonetic level. For example, a lexical retrieval diagnostic cell may require the patient to name the objects pear, rail, and crest from images on the screen. If the patient records her answers as pail, wail, and quest, then such results not only suggest that she has difficulty with the phoneme /r/ in all positions, but also which of her stored words with /r/ are ill-formed due to interference from /l/ and /w/.

From these word-level diagnostic cells, the patient can proceed to others such as morpheme recognition. For example, the process generates a morpheme recognition diagnostic cell that asks the patient to type in words with the suffix -er, based on her earlier errors with the phoneme /r/ in phoneme identification, syllabification, and/or word segmentation.

Another important word-level test is rapid naming. For example, the process generates a rapid naming cell that requires the patient to read words displayed on the display as such words appear. The words used can involve /i/-/I/ vowels if these were found to be problematic in the earlier diagnostic cells, such as beat v. bit. When incorporated in the rapid processing shell, the process requires the patient to recognize words speedily and automatically at a speed necessary for fluent reading.

Other diagnostic shells can involve sentence-level and text-level tests as described in the sample diagnostic shells section. Also, the shells may involve reading or writing. Further, some diagnostic cells are sensitive to an age of the patient, while others are not. For example, most, if not all, patients are expected to have acquired a full inventory of phonemes of the language. However, at least one word used in the cells can be selected based on age.

In the therapy phase, the therapy shells can be used as diagnostic shells and vice versa. Three therapy shells described below are novel to the field: phoneme discrimination as administered here, rapid word recognition, and word amplification.

With respect to therapy cells, problems found via phoneme identification shell in the diagnosis phase can lead the process to activate the phoneme discrimination therapy shell. In the phoneme discrimination shell, a minimal pair of words (e.g., pleats, bleats) is used for a phonemic contrast of interest (/p/-/b/). These two words are shown on the display. An audio recording plays such two words randomly at a set speed while the patient selects, by clicking or other input means, a word that is uttered at that point in time. The patient may begin at a slow speed of 60 words per minute (wpm)

and proceed onto faster and faster speeds exceeding 100 wpm. One goal is to approach a speed needed for auditory discrimination of speech sounds and for automatic recognition of words in fluent reading.

In the rapid word recognition shell, a minimal pair of words is used for the phonemic contrast of interest, as in the phoneme discrimination shell. Such two words are shown on the display. This time, the patient says a word that is highlighted on the display. Again, the patient may begin at a slow speed and proceed onto speeds exceeding 100 wpm. The rapid word recognition shell may be administered independently of the phoneme discrimination shell, or the rapid word recognition shell may follow the phoneme discrimination shell when the patient fails to progress to quicker speeds in the latter. In the second scenario, the rapid word recognition shell shows improvement in a speed for the phoneme discrimination shell.

In the word amplification shell, the patient is taught to attend to prosodic features of a word or phrase, such as intonation, stress pattern, and vowel quality. For example, if a patient registered problems with the /pr/ consonant cluster in the phoneme identification shell during diagnosis, then the process may generate a word amplification cell that plays a video or audio file of a person speaking that elongates a sound segment and exaggerates an intonational contour of the word, especially a beginning /pr/ segment. This may be similar to motherese, language with an exaggerated prosodic pattern that caretakers use with infants. The patient is asked to imitate this amplified pattern by recording and playing back her production or by answering a series of questions about a position and movement of her articulators, such as her lips, tongue, jaws, and so forth or by noting various auditory features, such as pitch and juncture.

One sequence of activating therapy shells depends on a problem identified in the diagnostic phase and new problems discovered in the therapy phase. To illustrate, if the patient displayed problems with the /p/-/b/ contrast in word-initial position in the diagnosis phase, then the process activates an articulation therapy cell that allows the patient to view from a model, practice, record, and review her articulation of the /p/ and /b/ phonemes. Next, the process presents her with a word discrimination cell that requires her to select the right word (or image associated with that word) when an audio recording plays a phrase or sentence. This cell may play five phrases or sentences. Her correct and incorrect responses are entered into the second data structure, such as the patient matrix, for later analysis. Next, the process activates the phoneme discrimination cell with five minimal pairs involving the /p/-/b/ contrast in word-initial position. If there is no error in task performance as described above for this type of cell, then the patient moves from pair to pair and to higher and higher speeds. However, if the patient encounters problems proceeding in this manner, then the process may run other cells, such as rapid word recognition involving a same minimal contrast before returning to phoneme discrimination, to see if the patient can clear the hurdle the second time. Other cells may be invoked on other failed attempts, such as additional articulation therapy cells that give more detailed cues, or live assistant may be called in at this point. Following this, the process activates the spelling pattern cell for /p/, which involves teaching the patient to recognize when p is pronounced as /f/ (ph). Further, the process trains and tests the patient in a rapid naming of words containing the letter p (/p/ or /f/ sound), and the sound /b/. The process may use an error committed earlier in word discrimination and elsewhere to generate the words in the rapid naming cell. The patient may start off slow, at 1.0 second per word, and proceed onto quicker and quicker speeds to approach 0.3 second per word. Note that typically developing students in Grade 4 and above are expected to achieve 120-180 correct words per minute. Once the patient reaches this goal, the training phase for the /p/-/b/ contrast in word-initial position is complete, and the patient proceeds to the next shell or cell. If the patient displayed problems with the /p/-/b/ contrast in word-medial position instead during the diagnosis phase, then the syllabification therapy cell is activated. This is because the syllabification therapy cell can help to train the patient to attend to phonetic features in the middle of words, such as focusing on the difference between flabby (/flæ-bi/) and flappy (/flæ-pi/).

Figure 11:
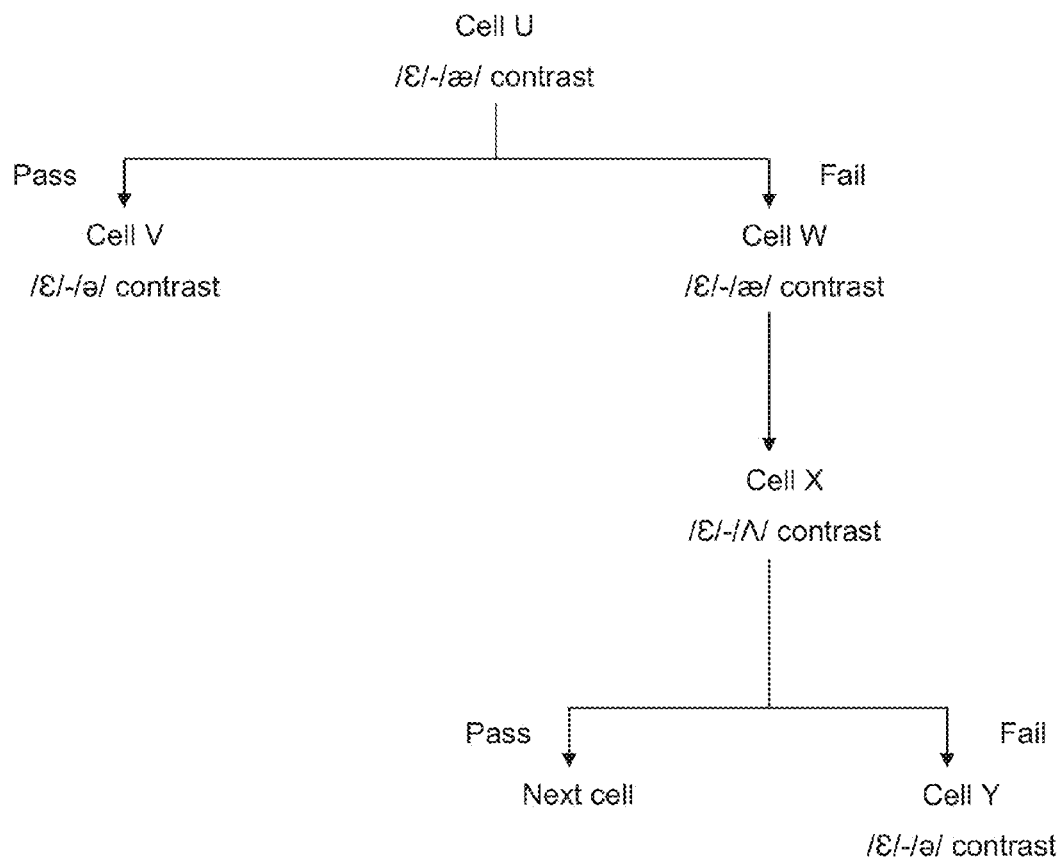
FIG. 11 shows a diagram of an example embodiment of a phoneme identification diagnostic shell and cells for vowels according to the present disclosure.

FIG. 11 shows a diagram of an example embodiment of a phoneme identification diagnostic shell and cells for vowels according to the present disclosure. Such methodology is implemented via the technology described herein. Phoneme identification diagnostic cell U tests patient's ability to distinguish /ɛ/-/æ/ (led, lad). If the patient commits no error, then the process generates cell V to test the /ɛ/-/ə/ contrast (fair, or fur). If the patient commits an error in cell U, then the process generates cell W to confirm the problem with the /ɛ/-/æ/ contrast as well as cell X to test a new contrast /ɛ/-/ʌ/ (bet, or butt). If the patient commits no error in cell X, she proceeds to the next cell. But if she commits an error in cell X, the process generates cell Y to test the /ɛ/-/ə/ contrast.

Further, note that any end user based technology disclosed herein, whether patient based or operator based, can be employed via any graphical user interfaces, whether monochrome, grayscale, or in color. For example, such interface can comprise a structural element, such as a window, a menu, an icon, a control unit/widget, or a tab. Also, for example, such interface can comprise an interaction element, such as a cursor, a selection unit, or an adjustment handle.

Moreover, in some embodiments, the computer 400 can be configured to detect the geolocation of the patient automatically, such as via the geolocating unit 414. Based on such detection, the computer 400 can be configured to at least partially output at least one of the diagnosis phase, whether in part or in whole, and the therapy phase, whether in part or in whole, based on a language or a dialect associated with that geolocation. For example, if the computer 400 detects that the patient is in France, then the computer 400 at least partially outputs at least one of the diagnosis phase, whether in part or in whole, and the therapy phase, whether in part or in whole, based in French, whether in part or in whole. Note that relevant cell data, shell data, game data and so forth can be translated automatically, whether in part or in whole, via the computer 400 and/or be available already pre-translated, whether in part or in whole. Note that such acts can be performed via the computer system 304 and/or the patient computer 308 in any manner. Further note that the patient can override, whether in part or in whole, and/or disable, whether in part or in whole, such feature, such as for travel purposes.

Additionally, in some embodiments, the computer 400 can be configured to detect patient language automatically, as vocally input into the microphone 418, such as via speech or voice recognition software. Then, based on such detection, the computer 400 at least partially outputs at least one of the diagnosis phase, whether in part or in whole, and the therapy based in that language, whether in part or in whole.

Moreover, in some embodiments, the computer 400 can be configured to at least partially employ the NFC circuitry to interact with another NFC circuit during at least partial output at least one of the diagnosis phase, whether in part or in whole, and the therapy phase, whether in part or in whole. For example, based on a cell task, the patient can be instructed to move the computer 400, such as via waving against or touching another object, such as an NFC unit. Upon such movement, the NFC circuitry can instruct the computer 400 whether the task was performed and if so, then whether the task was properly performed.

In addition, in some embodiments, the computer 400, such as the mobile phone 216, can be configured to run a software application, which at least partially embodies at least some of the technology disclosed herein, such as for the diagnosis phase and/or the therapy phase, whether in whole or in part. The software application can run silently in a background of the computer 400. The software application can be configured such that the computer 400 listens to the patient's responses via the microphone 418 when the patient goes about her day and converses with other people, such as at work, school, home, and so forth. Such listening can be whether the patient is using the computer 400, such as via conducting a telephone call or a teleconferencing session, and/or the patient is not using the computer 400, such as when the computer 400 is resting on a table. The application can be configured to automatically filter for background noises and/or voices other than the patient. Further, for privacy and/or for data security purposes, the application can also be configured to automatically delete the background noises and/or the voices other than the patient, as preset in advance. However, for any language, as spoken via the patient and recorded via the application, the system 304 can be configured to process such information, such as upon receipt from the computer 400, and utilize this information for the provision of the diagnosis phase and/or the therapy phase, whether in whole or in part, such as via a diagnosis cell and/or a therapy cell.

Furthermore, in some embodiments, the computer 400 can be implantable, such as a hearing aid, or wearable, such as with an optical head-mounted display (OHMD). Such computer 400 can comprise a vibrator for bone conduction, such as for sound hearing, or a similar device for articulation analysis. For example, the vibrator can provide a vibrational output to a jaw bone such that the jaw bone conducts a sound to an inner ear of the patient. Alternatively, the computer 400 can be configured to provide information on the patient's articulation of particular sounds by monitoring such features as the vibration of the patient's vocal cords and manner of airflow in the patient's oral cavity. Accordingly, the computer 400 can be configured to provide at least partial output of at least one of the diagnosis phase, whether in part or in whole, and the therapy phase, whether in part or in whole, even in the language as selected via the geolocating unit 414 based on the geolocation of the computer 400.

Moreover, in some embodiments, the computer 400 can be configured for facial coding in order to categorize patient facial movements via their facial appearance, such as for emotion determination and articulation training or speech therapy, during at least one of the diagnosis phase, whether in part or in whole, and the therapy phase, whether in part or in whole. Such categorization can be used as an iterative feedback loop to enhance in at least one of the diagnosis phase, whether in part or in whole, and the therapy phase, whether in part or in whole. For example, the computer 400 can detect the patient's face in at least one of the diagnosis phase, whether in part or in whole, and the therapy phase, whether in part or in whole, extract a geometrical feature of the patient's face, produce a temporal profile of each patient facial movement, and then supply such profile, such as to the computer system 304, whether to the first data structure and/or the second data structure, for use as an iterative feedback loop to enhance in at least one of the diagnosis phase, whether in part or in whole, and the therapy phase, whether in part or in whole.

Further, in some embodiments, the computer 400 can be implantable or wearable. Such computer 400 can identify and map problem areas of the patient's brain for language processing as determined through at least one of the diagnosis phrase and therapy phase. As an implanted or wearable device, the computer 400 can monitor activity of nerve cells and use brain signals to correlate physical areas of the brain with the functional areas mapped by the program through at least one of the diagnosis phase and the therapy phase. Such computer 400 can then stimulate brain circuits through corrective action through the therapy phase. Such computer 400 can monitor changes in brain circuitry as determined through brain activation and patient output from the therapy cells. For example, this monitoring of the activated areas in the brain may indicate that a patient is close to reaching a target sound in her approximations during therapy. In such a case, the program intensifies her therapy at this juncture to get her past this goal and reinforces her training to ensure secure acquisition.

In addition, in some embodiments, the computer 400 can be configured for second language learning. In such a case, the first data structure, such as the master matrix, would be configured to predict errors likely to be committed by second language learners for the language or dialect in question. Most of the therapy shells would remain, especially if learners are aiming for native-like fluency. New diagnostic and therapy shells would cover and/or be updated to cover more components of grammar, sentence construction, and pragmatics (language use in context), especially if at least some information is obtained from other patients utilizing the computer system 304.

Further, in some embodiments, the computer 400 can be configured for accent modification in which a patient receives speech therapy to alter her native accent. For example, a person may decide to reduce a regional or stigmatized accent for professional reasons. In such a case, her therapy will focus more on phoneme identification and discrimination and word amplification and less on rapid word recognition. The appropriate therapy cells would have been generated by the diagnostic shells selected for such a program. Namely, the diagnostic shells will primarily cover articulation at the segmental (sound) and prosodic (utterance) levels. In other embodiments, the patient can be a machine that produces human-like speech during task performance, such as for machine learning purposes. In such instances, the computer 400 can be configured to provide corrective training so that the patient-machine approximates natural speech at the segmental, prosodic, and syntactic levels.

Additionally, the applicants conducted a study on a therapy method delivered in person that forms a basis of the present disclosure. An experimental group in this study adopted a flexible, data-driven methodology that used detailed, ongoing linguistic-cognitive profiles of each student to generate individualized training drills. A control group used an Orton-Gillingham-based approach. A comparison of segmentation skill between the experimental group and the control group showed statistically significant transfer effects in the former and a slight drop in the latter. With the experimental group, the combined training in phonemic awareness and rapid automatized naming also resulted in stronger performance in word recognition.

More particularly, the study compared an individualized approach, based on the methodologies disclosed herein, to a standardized approach to intervention for struggling readers in middle school. The Wilson Reading System, based the on Orton-Gillingham principles, served as the standardized approach in the control group. The individualized approach used in the experimental group was a new form of intervention that used creative problem solving to address the specific reading and language processing problems identified in each student. Called responsive intervention here, the approach required the development of detailed linguistic-cognitive profile of each student in order to customize training. The study design followed the recommended criteria of the National Reading Panel (2000) and the Institute of Education Sciences (2013) for efficacy research. The results showed a significant impact difference in segmentation skill between the two methods, providing further confirmation and explanation for the weaknesses of existing intervention programs.

The site of the present study was a public junior high school with an enrollment of over 1,400, with around 260 students in special education. This junior high school was located in a predominantly middle- to upper-middle income area in the state of New York. The study was conducted in conjunction with an afterschool reading program on site that ran from March-June, 2014. The program was organized by the research team and offered as a community service to participants.

This study conformed to the National Reading Panel's (2000) criteria for a well-designed experiment that provides strong evidence for cause as well as those of the Institute of Education Sciences (2013). The National Reading Panel (2000) meta-analysis of reading studies concluded that effect sizes were larger when children received focused and explicit instruction on no more than one or two phonemic awareness (PA) skills. Also, programs that focused on both letters and phonemes were more effective than those that only covered one. In the present study, the experimental group learned IPA (International Phonetic Association) symbols in addition to letters and phonemes. The experimental group practiced recognizing individual sounds in words (phoneme isolation) as the only PA skill taught directly. But the end-of-program assessment tested another PA skill, segmentation, to determine transference.

The National Reading Panel's review also found that effects were greater when students were taught in small groups, compared to classrooms or one-to-one settings. The optimal total time of instruction was found to be five to 18 hours. In the current study, group sizes ranged from an average of seven to 10 students per session. Instruction time averaged 35 minutes each session for a total of 8.25 hours. To ensure internal validity, participants were assigned randomly to the two groups as described below. The two groups were equivalent on key factors (described below), as confirmed by chi-squared tests. A student who was receiving Wilson intervention during school hours was asked to withdraw from the program and was not counted in the statistical analysis.

The National Reading Panel (2000) found that transfer effects were greater when studies used experimenter-devised tests to measure reading improvement since standardized tests may be less sensitive in detecting changes in the skills under investigation. The pretests and posttests used in the present study were developed by the authors to measure segmentation ability. One final recommendation, conducting follow-up posttests to assess the long-term effects of training some time after completion of the intervention, could not be implemented in this study because the program ended at the close of the school year.

Participants were nominated by the school's teachers as students in special education who would benefit from the afterschool reading program. Twenty-six students participated in the afterschool program: 15 from Grade 6 and 11 from Grade 7. To assign participants to the control and experimental groups, the students were first divided by grade. Students in each grade were randomly assigned to either the control or experimental group. Of the 26 students who participated in the program, 18 attended the afterschool sessions to the end of the school year and were included in the control study. There was an equal distribution of sixth and seventh graders in both groups, with nine students each (six in Grade 6, three in Grade 7).

All the students in the control study were from two-parent households. Of these 18 students, five were female (three in control, two in experimental groups) and 13 male (six in control, seven in experimental groups); and seven were minority students (four in control, three in experimental groups). Five of the students in the control group and six in the experimental group were receiving speech/language therapy services. The study's participants all scored at Level 1 or 2 on the New York State's English Language Arts (ELA) test in Grade 4. Level 1 is considered "Below Standard," in which student performance does not demonstrate an understanding of the English language knowledge and skills expected at this grade level (New York State Department of Education, 2012). Performance at Level 2 demonstrates partial understanding. Above it are Level 3 ("Meets Proficiency Standard") and Level 4 ("Exceeds Proficiency Standard"). For one student in the control and one in the experimental group, only their ELA Grade 5 scores were available, and they were both at Level 2. The ELA scores of two of the students in the control group were not available. IQ scores were not considered because these struggling readers could have language-processing problems, which could have affected their IQ scores. A series of chi-squared tests revealed no significant differences between the control and experimental groups in terms of gender, minority status, participation in speech/language therapy, grade level, and two-/single-parent household. Two of the students in the control group and three in the experimental group were overage for their grade levels, suggesting that they had repeated a grade. This factor was also found not to be statistically significant between the two groups.

The afterschool sessions for the control and experimental groups ran for 45 minutes every Tuesday from March-June 2014 except for a one-week midterm break. Instruction time was 35 minutes, after subtracting 10 minutes for settling in and getting ready to take the late bus. Each group was taught by a teacher in a separate classroom (see Control Group and Experimental Group below). Each teacher was supported by a teaching assistant in 75% of the sessions. The teachers kept attendance logs while their teaching assistants recorded the level of participation of each student in their groups (see Fidelity of Implementation below). Both teachers assigned homework that took no more than an hour total a week.

The teacher who taught the control group was hired through a selection process conducted by the school, which screened applicants among its own teachers in special education. The instructor selected had nine years of teaching experience and Wilson Level 1 certification.

The control group strictly followed the Wilson Reading System. The class used the Third Edition of the Wilson Reading System's Instructor Manual, Rules Notebook, and Student Reader One and Two. As explained on the company's website, the Wilson Reading System is a step-by-step program aimed at teaching encoding and decoding skills, proceeding from monosyllabic to multisyllabic words. It asks students to tap out the sounds of words in learning segmentation (Wilson Language Training Corp., 2010).

During the program, the control group worked on closed syllables and exceptions, digraphs (two-letter combinations that form single sounds, such as ee), welded sounds (e.g., all, ing), blending and segmenting, vowels (a, e, i, o, u) and consonants. The teacher introduced new concepts methodically, allowing for practice and review. Class activities were all dictated by the Wilson method and included identifying concepts such as welded sounds in words (ball), blending letters (representing sounds) into words (r-am=ram), filling in sentences with given words, identifying phrasal boundaries in written sentences, completing words with given letters, and reading simple passages. The teacher distributed weekly packets from the Wilson curriculum for review at home.

The teacher in the experimental group was one of the inventors of the present application. That inventor had over 20 years of experience in teaching at the college level, but none at the non-tertiary level. That inventor had worked with students with reading disabilities in one-to-one settings for over eight years, but was not trained in any standardized approach.

The experimental intervention involved responding directly to the language problems seen in each student. Consequently, the form and pace of intervention in the experimental group varied for each student, depending on his or her difficulties and progress. To execute this type of responsive intervention, the initial profiles of the students' language abilities and weaknesses were gathered through a series of short tests designed by the authors to identify each student's problem areas. The tests, which took no more than 15 minutes per student, were administered one-on-one before the start of the program in a quiet classroom. The tests covered basic phonological knowledge. Students were asked to identify vowels in words (/i/ in beat), segment words (/f r e m d/ framed), and break up words into syllables (ad-van-tage).

The initial evaluation was followed by further observation and recording of students' reception and production errors each week. These data sources were used to generate individual profiles that contained information on each student's problems with phonemes (consonants and vowels), phonological processes (e.g., neutralization of unstressed vowels to /ə/), orthography (spelling patterns), morphological structures (word formation), and morphophonemic processes (e.g., devoicing of past tense morpheme in base words ending in voiceless consonants, such as /slæpt/ slapped). The students' linguistic-cognitive profiles included problems in reception (listening and reading) and production (speaking and spelling). Because the program only ran for three months, the experimental class did not cover larger linguistic structures such as lexical (word) collocations, phrases, sentences, and texts. It is generally accepted in the field that phonological, orthographic, and morphological knowledge are key components of reading development (Berninger, Abbott, Nagy, & Carlisle, 2010) and should be taught directly (Torgesen, 2004).

Each student's cumulative profile was used to generate new drills specifically for him or her for the following week. Four of the students in the experimental group had articulation problems and experienced difficulty controlling air flow and voice volume. These students started in the program with articulation exercises, practicing with props as needed. For example, they used hand-held mirrors to check on the movement of their lips (lip spreading or rounding) and lollipops to feel the position of their tongues in vowel production. Regardless of individual pacing, the experimental group as a whole generally progressed from pronunciation, auditory discrimination of phonemes, and representing sounds in the form of phonetic symbols to learning phoneme-grapheme (sound-letter) mappings and spelling patterns.

Drills in the second half of the program focused on rapid naming of words containing the spelling patterns learned earlier. Although rapid automatized naming (RAN) has been used in assessment and research for over three decades (Denckla & Rudel, 1976), the actual nature and role of rapid naming in reading disability is still unclear (see Elliott & Grigorenko's review of studies, 2014). RAN was employed for a different purpose in this study: to catch students' errors in recognizing spelling patterns and use the information gathered to develop future drills. RAN traditionally involved letters, digits, and object names, but in the version of RAN adopted in this study, participants read aloud single words flashed on the screen at prescribed times using MS PowerPoint. Each word list contained an average of 40 words. Most of the words were either monosyllabic, such as rut, or bisyllabic, such as roaster. No more than three of the words in each list contained more than two syllables, such as happiness. A scorer recorded correct and incorrect readings of test words, which were then used to generate new drills for subsequent weeks. For example, when a student misread sitting as sighting, subsequent drills included distinguishing between the spelling patterns for the vowels /ai/ (-ight, -ite, -ie, etc.) and /I/ (i). Instruction in the class was similarly individualized. Much of class time was spent on on-on-one conferencing, collaborative work, and groupwork. Each student received weekly packets tailored to his or her particular problems with language. It is important to note that segmentation skill was not taught directly and explicitly to the class. The students' weekly packets similarly did not include segmentation exercises. This was to see if transference effects occurred.

Fidelity of implementation was considered in line with the *Common Guidelines for Education Research and Development of the IES* (Institute of Education Sciences, 2013) for efficacy research. Fidelity of implementation of the Wilson method in the control group was monitored through a combination of classroom observations, student attendance and participation, class time use, pedagogic strategies, and teaching materials and content. The teacher in the control group prepared lesson plans by filling in fully the Wilson Reading System Lesson Plan forms, spelling out the specific words to be taught. The research team confirmed that she kept close to the plan, with the only modifications being continuation of the material into a second week when needed. Additionally, the teaching assistant in the control group, who was affiliated with the authors' college and not the participating school, served as the observer of the control class. The teaching assistant's observations were made at least once every other week, either in writing or through oral communication. The teaching assistant's reports confirmed that the teacher followed closely the Wilson Reading System®—presenting the structure of language systematically and cumulatively; reinforcing concepts through multisensory channels; using questioning techniques and giving feedback on students' errors. Furthermore, as an experienced instructor, the teacher varied class activity and pacing to keep students engaged.

The teaching assistants in both classes rated the students in their own groups on their level of attention and participation in the classroom based on attendance, attention to task at hand, response to teachers' questions, and distractibility (e.g., cell phone use). On a four-point scale system (Good, Average, Fair, Poor), the control group received the following ratings: Good—3, Average—4, Fair—1, Poor—1. The experimental group received the following ratings: Good—2, Average—3, Fair—2, Poor—2.

The experimental class followed a highly fluid, flexible arrangement that did not allow for easy monitoring of fidelity of implementation. Nevertheless, the following information was gathered from the training sessions each week: student attendance and participation, notes on conferencing with every student in the group, and distribution of individualized weekly packets for every student. The collected data showed that every student present in each session received one-on-one conferencing at least once from the teacher or teaching assistant. Every student present also received an individualized weekly packet. Both classes met and ended at the same time on the same day in the same building.

The same segmentation test was administered a week before the start of the afterschool program (pretest) and the last week of the program (posttest). The segmentation test consisted of a list of 10 common words that contained some monosyllabic words such as praise and bisyllabic ones such as flower. Seven of the words occur as the top 5,000 most frequent words in usage (Davies & Gardner, 2010). The test was administered individually to each student in a quiet room. The student's oral production was transcribed in person into IPA phonetic symbols, with junctures (breaks between sounds) noted. When needed, the students were asked to segment the words in question again to confirm the transcription. All the students in both groups were administered the same test in the same manner. Points were allocated as follows: 0—The test word was uttered as a single unit; the student uttered the wrong sound; the sound was in the wrong position in the word; the student said the letter instead of the sound (e.g., "double U" W instead of /w/ sound); or the student abandoned the attempt to segment the word. 1—A single phoneme or phoneme cluster was given in the right position in the word. (A point was still given for a phoneme cluster even though in this case the student had not segmented the word completely; a comparison of her score and the total would indicate that her segmentation was not complete.)

Close to the end of the program, all participants were tested on their speed in word recognition. Thirty-six words were placed singly into MS PowerPoint slides (Calibri 44 point size font) and set to display at 0.3 second (i.e., 200 words per minute). All the words were in the top 1,000 of the most frequently used words in contemporary American English, such as anything and least (Davies & Gardner, 2010). Three blank slides separated every $10^{th}$ word to allow students to pause between their rapid reading of the words flashing on the screen. The test was administered individually in a quiet area without the presence of the other students. Only readings in the exact forms of the words were accepted. For example, no points were given if a student read response as respond.

The segmentation tests were administered from a test manual that contained the exact instructions to give orally to the students. An example was given to clarify segmentation ("For example, 'cat' is /k æ t/"). Each student was asked to repeat the test word to confirm that the right word was heard before segmenting it into individual sounds (phonemes). Students were given as much time as needed to complete each item. For every test item and response, the testers were friendly but did not offer any feedback. For the RAN test, the testers checked with the students to make sure that they were ready to read the words on the screen. Ten blank slides preceded the first word to give the students time to prepare. The testers used a word list in the order of the slide presentation to check off the correct readings.

Some of the inventors of the present application served as testers and had practiced using the same protocols for administering and scoring the same segmentation test for other students for over a year prior to this study. To determine inter-rater reliability, all the segmentation pretests were scored independently by both authors, and 33.3% of the segmentation posttests were scored by a second evaluator. Inter-rater reliability was 99.4% for the pretests and 99.7% for the posttests. Inter-rater reliability was not monitored for the RAN test since scoring only involved checking off correct readings of test words on a list.

A series of analyses of covariance (ANCOVAs) were run to examine the effect of the intervention on segmentation skill. Both ELA and segmentation pretest scores were entered as covariates. Table 1 shows unadjusted and adjusted means for these analyses. The ANCOVA for the segmentation test revealed a significant effect of the intervention, $F(1, 12)=15.11$, $p=0.002$, $\eta^2=0.557$ (see Table 2). Students in the experimental group performed better than control students on this assessment. The segmentation scores of two students in the control group were not included in the calculation because their ELA scores were not available. But their performance on the pretest and posttest fell within the range of the scores of others in their control group (pretest: 20 and 20 out of 59; posttest: 13 and 17 out of 59).

Both groups of students started in the program with similar unadjusted mean scores (25 v. 26 out of 59) but diverged significantly at the end (45 v. 21). Four members of the control group actually showed substantial drops in scores, with three of them experiencing decreases of over 20.0%. In contrast, five students out of the nine in the experimental group showed gains of over 33.9%. At the beginning of the program, both groups generally could only divide words into syllables, not phonemes, as seen in their pretest scores. After the intervention, all the students in the experimental group were able to segment a majority of the test words into single phonemes. The only student in the experimental group who was not able to score above 40 out of 59 in the posttest missed a month of sessions in the middle of the program.

RAN was part of the responsive intervention program of the experimental group. As noted earlier, RAN was used to detect weaknesses in the application of spelling rules at the speed needed for fluent reading. At the beginning of intervention, all of the students in the experimental group made errors even at speeds slower than 60 words per minute (wpm), and most of them could not perform the task above 120 wpm. Typically developing students in Grade 4 and above are expected to achieve 120-180 correct words per minute (cwpm) (Shaywitz, 2003, p. 277). Two months into the program, students in the experimental group were able to perform at speeds between 120-200 wpm. For example, one student misread the /u/ sound in roosting, toot, rooted, and noose in an earlier RAN assessment. After further practice, he was able to read the words tooting, drooping, loose, and croon correctly in a subsequent RAN test at 200 wpm.

Close to the end of the program, a RAN test was administered to both groups to see if the combined PA and speed training improved the experimental group's accuracy in word recognition. Each student in the experimental group read an average of 44.4% of test words correctly at 200 wpm, compared to 31.0% for the control group. More importantly, five students out of the nine in the experimental group scored above 50.0% compared to only one in the control group.

TABLE 1

Descriptive statistics of unadjusted and adjusted means of segmentation posttest by group

| | Unadjusted means | | | Adjusted means | | | |
|---|---|---|---|---|---|---|---|
| | | | | | | 95% Confidence Interval | |
| Group | Mean | Std. Deviation | N | Mean | Std. Error | Lower Bound | Upper Bound |
| Control | 23.2857 | 10.67262 | 7 | 23.667[a] | 3.766 | 15.461 | 31.873 |
| Experimental | 45.3333 | 7.08872 | 9 | 45.037[a] | 3.226 | 38.008 | 52.065 |
| Total | 35.6875 | 14.14081 | 16 | | | | |

[a]Covariates appearing in the model are evaluated at the following values: ELA Grade 4 score = 626.88, segmentation pretest score = 26.2500.

TABLE 2

Segmentation posttest: Tests of between-subjects effects

| Source | Type III Sum of Squares | df | Mean Square | F | Sig. | Partial Eta Squared | Observed Power[c] |
|---|---|---|---|---|---|---|---|
| Corrected Model | 2112.652[b] | 3 | 704.217 | 9.529 | .002 | .704 | .977 |
| Intercept | .778 | 1 | .778 | .011 | .920 | .001 | .051 |
| ELA Grade 4 | 17.658 | 1 | 17.658 | .239 | .634 | .020 | .074 |
| Segmentation Pretest | 165.954 | 1 | 165.954 | 2.246 | .160 | .158 | .281 |
| Group | 1116.269 | 1 | 1116.269 | 15.105 | .002 | .557 | .945 |
| Error | 886.785 | 12 | 73.899 | | | | |
| Total | 23377.000 | 16 | | | | | |
| Corrected Total | 2999.438 | 15 | | | | | |

[b]R Squared = .704 (Adjusted R Squared = .630)
[c]Computed using alpha = .05

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

In some embodiments, an apparatus or system comprise at least one processor, and memory storing instructions that, when executed by the at least one processor, cause the apparatus or system to perform one or more methodological acts as described herein. In some embodiments, the memory stores data, such as one or more structures, metadata, lines, tags, blocks, strings, or other suitable data organizations.

As will be appreciated by one skilled in the art, aspects of this disclosure can be embodied as a system, method or computer program product. Accordingly, aspects of the present disclosure can take the form of an entirely hardware embodiment, an entirely software embodiment (including firmware, resident software, micro-code, etc.) or as embodiments combining software and hardware aspects that can all generally be referred to herein as a "circuit," "module" or "system." Furthermore, aspects of the disclosure can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific example (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain, or store a program for use by or in connection with an instruction execution system, apparatus, or device.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be any computer readable medium that is not a computer readable storage medium and that can communicate, propagate, or transport a program for use by or in connection with an instruction execution system, apparatus, or device. Program code embodied on a computer readable medium can be transmitted using any appropriate medium, including but not limited to wireless, wireline, optical fiber cable, radiofrequency (RF), etc., or any suitable combination of the foregoing.

Computer program code for carrying out operations for aspects of the present disclosure can be written in any combination of one or more programming language, including an object oriented programming language, such as Java, Smalltalk, C++ or the like and conventional procedural programming language, such as the "C" programming language or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

What is claimed is:

1. A method comprising:
    diagnosing a language-related disorder automatically via:
        obtaining, by a first computer, a first set of criteria, wherein the first set of criteria is based at least in part on a first automated analysis of a patient data structure against a master data structure, wherein the patient data structure comprises a set of actual patient task responses, wherein the master data structure comprises a set of cell generation data and a set of predicted patient task responses for a plurality of patients;
        storing, by the first computer, a first cell result in the patient data structure, wherein the first cell result is received from a second computer, wherein the second computer is at least one of implantable or wearable, wherein the second computer comprises a vibrator configured to vibrate such that a first sound is conducted along a jaw bone of a patient to an inner ear of the patient, wherein the patient is associated with the patient data structure, wherein the first cell result is based at least in part on the first computer selecting a first diagnostic shell based at least in part on the first set of criteria, generating a first diagnostic cell dynamically based at least in part on the first diagnostic shell, the set of actual patient task responses, and the set of cell generation data, and communicating the first diagnostic cell to the second computer such that the second computer is able to output the first diagnostic cell via the vibrator vibrating such that the first sound is conducted along the jaw bone to the inner ear, wherein the first sound comprises the first diagnostic cell, wherein the first diagnostic cell comprises a first diagnostic cell content which is created dynamically by the first computer based at least in part on an incorrect actual patient task response sourced from the set of actual patient task responses;
        obtaining, by the first computer, a second set of criteria, wherein the second set of criteria is based at least in part on a second automated analysis of the patient data structure, including the first cell result, against the master data structure;
        determining, by the first computer, based at least in part on the second set of criteria at least one of whether to generate a second diagnostic cell dynamically based at least in part on the first diagnostic shell such that the second computer is able to output the second diagnostic cell via the vibrator vibrating such that a second sound is conducted along the jaw bone to the inner ear, the set of actual patient task responses, and the set of cell generation data, whether to select a second diagnostic shell, or whether to provide a diagnosis of the language-related disorder to the second computer, wherein the first diagnostic shell and the second diagnostic shell are different in task type, wherein the second sound comprises the second diagnostic cell, wherein the second diagnostic cell comprises a second diagnostic cell content which is created dynamically by the first computer without relying on a second predetermined cell content.

2. The method of claim 1, wherein the disorder is at least one of dyslexia, specific language impairment, auditory processing disorder, or aphasia.

3. The method of claim 1, further comprising:
    providing therapy of the language-related disorder automatically based at least in part on the diagnosis via:
        obtaining, by the first computer, a third set of criteria, wherein the third set of criteria is based at least in part on a third automated analysis of the patient data structure, including the first cell result, against the master data structure;
        storing, by the first computer, a second cell result in the patient data structure, wherein the second cell result is received from the second computer, wherein the second cell result is based at least in part on the first computer selecting a first therapy shell based at least in part on the third set of criteria, generating a first therapy cell dynamically based at least in part on the first therapy shell, the set of actual patient task responses, and the set of cell generation data, and communicating the first therapy cell to the second computer;
        obtaining, by the first computer, a fourth set of criteria, wherein the fourth set of criteria is based at least in part on a fourth automated analysis of the patient data structure, including the first cell result and the second cell result, against the master data structure;
        determining, by the first computer, based at least in part on the fourth set of criteria at least one of whether to generate a second therapy cell dynamically based at least in part on the first therapy shell, the set of actual patient task responses, and the set of cell generation data, whether to select a second therapy shell, or whether to complete the therapy, wherein the first therapy shell and the second therapy shell are different in task type.

4. The method of claim 3, wherein at least one of the first therapy cell or the second therapy cell comprises a training unit and an evaluation unit.

5. The method of claim 3, wherein the first therapy shell and the second therapy shell is at least one of a phoneme discrimination therapy shell, a rapid word recognition therapy shell, or a word amplification therapy shell.

6. The method of claim 3, further comprising:
gamifying, by the first computer, at least one of the first diagnostic cell, the second diagnostic cell, the first therapy cell, or the second therapy cell, wherein the gamifying is interactive and age based;
rewarding, based at least in part on the gamifying, the patient via a reward system running on the first computer, wherein the patient operates the second computer.

7. The method of claim 1, further comprising a third diagnostic shell, wherein the first diagnostic shell is a phoneme identification diagnostic shell, the second diagnostic shell is a sound-symbol matching diagnostic shell, and the third diagnostic shell is at least one of a syllabification diagnostic shell, a rapid naming diagnostic shell, or a word segmentation diagnostic shell, wherein the third diagnostic shell follows the second diagnostic shell.

8. A system comprising:
a computer system configured to diagnose a language-related disorder automatically via:
obtaining a first set of criteria, wherein the first set of criteria is based at least in part on a first automated analysis of a patient data structure against a master data structure, wherein the patient data structure comprises a set of actual patient task responses, wherein the master data structure comprises a set of cell generation data and a set of predicted patient task responses for a plurality of patients;
storing a first cell result in the patient data structure, wherein the first cell result is received from a computing device over a communication network, wherein the computing device is at least one of implantable or wearable, wherein the computing device comprises a vibrator configured to vibrate such that a first sound is conducted along a jaw bone of a patient to an inner ear of the patient, wherein the patient is associated with the patient data structure, wherein the first cell result is based at least in part on the computer system selecting a first diagnostic shell based at least in part on the first set of criteria, generating a first diagnostic cell dynamically based at least in part on the first diagnostic shell, the set of actual patient task responses, and the set of cell generation data, and communicating the first diagnostic cell to the computing device over the communication network such that the computing device is able to output the first diagnostic cell via the vibrator vibrating such that the first sound is conducted along the jaw bone to the inner ear, wherein the first sound comprises the first diagnostic cell, wherein the first diagnostic cell comprises a first diagnostic cell content which is created dynamically by the computer system based at least in part on an incorrect actual patient task response sourced from the set of actual patient task responses;
obtaining a second set of criteria, wherein the second set of criteria is based at least in part on a second automated analysis of the patient data structure, including the first cell result, against the master data structure;
determining based at least in part on the second set of criteria at least one of whether to generate a second diagnostic cell dynamically based at least in part on the first diagnostic shell such that the computing device is able to output the second diagnostic cell via the vibrator vibrating such that a second sound is conducted along the jaw bone to the inner ear, the set of actual patient task responses, and the set of cell generation data, whether to select a second diagnostic shell, or whether to provide a diagnosis of the language-related disorder to the computing device over the communication network, wherein the first diagnostic shell and the second diagnostic shell are different in task type, wherein the second sound comprises the second diagnostic cell, wherein the second diagnostic cell comprises a second diagnostic cell content which is created dynamically by the computer system without relying on a second predetermined cell content.

9. The system of claim 8, wherein the disorder is at least one of dyslexia, specific language impairment, auditory processing disorder, or aphasia.

10. The system of claim 8, wherein the computer system is further configured to provide therapy of the language-related disorder automatically based at least in part on the diagnosis via:
obtaining a third set of criteria, wherein the third set of criteria is based at least in part on a third automated analysis of the patient data structure, including the first cell result, against the master data structure;
storing a second cell result in the patient data structure, wherein the second cell result is received from the computing device over the communication network, wherein the second cell result is based at least in part on the computer system selecting a first therapy shell based at least in part on the third set of criteria, generating a first therapy cell dynamically based at least in part on the first therapy shell, the set of actual patient task responses, and the set of cell generation data, and communicating the first therapy cell to the computing device over the communication network;
obtaining a fourth set of criteria, wherein the fourth set of criteria is based at least in part on a fourth automated analysis of the patient data structure, including the first cell result and the second cell result, against the master data structure;
determining based at least in part on the fourth set of criteria at least one of whether to generate a second therapy cell dynamically based at least in part on the first therapy shell, the set of actual patient task responses, and the set of cell generation data, whether to select a second therapy shell, or whether to complete the therapy, wherein the first therapy shell and the second therapy shell are different in task type.

11. The system of claim 10, wherein at least one of the first therapy cell or the second therapy cell comprises a training unit and an evaluation unit.

12. The system of claim 10, wherein the first therapy shell and the second therapy shell is at least one of a phoneme discrimination therapy shell, a rapid word recognition therapy shell, or a word amplification therapy shell.

13. The system of claim 10, further comprising:
gamifying, by the computer system, at least one of the first diagnostic cell, the second diagnostic cell, the first therapy cell, or the second therapy cell, wherein the gamifying is interactive and age based;
rewarding, based at least in part on the gamifying, the patient via a reward system running on the computer system, wherein the patient operates the computing device.

14. The system of claim 8, further comprising a third diagnostic shell, wherein the first diagnostic shell is a phoneme identification diagnostic shell, the second diagnostic shell is a sound-symbol matching diagnostic shell, and the third diagnostic shell is at least one of a syllabification diagnostic shell, a rapid naming diagnostic shell, or a word segmentation diagnostic shell, wherein the third diagnostic shell follows the second diagnostic shell.

15. A computer-readable storage device storing a set of instructions for execution via a processing circuit, wherein the set of instructions is instructive for the processing circuit to implement a method, wherein the method comprises:
diagnosing dyslexia automatically via:
obtaining, by a first computer, a first set of criteria, wherein the first set of criteria is based at least in part on a first automated analysis of a patient data structure against a master data structure, wherein the patient data structure comprises a set of actual patient task responses, wherein the master data structure comprises a set of cell generation data and a set of predicted patient task responses for a plurality of patients;
storing, by the first computer, a first cell result in the patient data structure, wherein the first cell result is received from a second computer over a communication network, wherein the second computer is at least one of implantable or wearable, wherein the second computer comprises a vibrator configured to vibrate such that a first sound is conducted along a jaw bone of a patient to an inner ear of the patient, wherein the patient is associated with the patient data structure, wherein the first cell result is based at least in part on the first computer selecting a first diagnostic shell based at least in part on the first set of criteria, generating a first diagnostic cell dynamically based at least in part on the first diagnostic shell, the set of actual patient task responses, and the set of cell generation data, and communicating the first diagnostic cell to the second computer over the communication network such that the second computer is able to output the first diagnostic cell via the vibrator vibrating such that the first sound is conducted along the jaw bone to the inner ear, wherein the first sound comprises the first diagnostic cell, wherein the first diagnostic cell comprises a first diagnostic cell content which is created dynamically by the first computer based at least in part on an incorrect actual patient task response sourced from the set of actual patient task responses;
obtaining, by the first computer, a second set of criteria, wherein the second set of criteria is based at least in part on a second automated analysis of the patient data structure, including the first cell result, against the master data structure;
determining, by the first computer, based at least in part on the second set of criteria at least one of whether to generate a second diagnostic cell dynamically based at least in part on the first diagnostic shell such that the second computer is able to output the second diagnostic cell via the vibrator vibrating such that a second sound is conducted along the jaw bone to the inner ear, the set of actual patient task responses, and the set of cell generation data, whether to select a second diagnostic shell, or whether to provide a diagnosis of the dyslexia to the second computer over the communication network, wherein the first diagnostic shell and the second diagnostic shell are different in task type, wherein the second sound comprises the second diagnostic cell, wherein the second diagnostic cell comprises a second diagnostic cell content which is created dynamically by the first computer without relying on a second predetermined cell content.

16. The computer-readable storage device of claim 15, wherein the method further comprises:
providing therapy of the dyslexia automatically based at least in part on the diagnosis via:
obtaining, by the first computer, a third set of criteria, wherein the third set of criteria is based at least in part on a third automated analysis of the patient data structure, including the first cell result, against the master data structure;
storing, by the first computer, a second cell result in the patient data structure, wherein the second cell result is received from the second computer over the communication network, wherein the second cell result is based at least in part on the first computer selecting a first therapy shell based at least in part on the third set of criteria, generating a first therapy cell dynamically based at least in part on the first therapy shell, the actual patient task responses, and the set of cell generation data, and communicating the first therapy cell to the second computer over the communication network;
obtaining, by the first computer, a fourth set of criteria, wherein the fourth set of criteria is based at least in part on a fourth automated analysis of the patient data structure, including the first cell result and the second cell result, against the master data structure;
determining, by the first computer, based at least in part on the fourth set of criteria at least one of whether to generate a second therapy cell dynamically based at least in part on the first therapy shell, the set of actual patient task responses, and the set of cell generation data, whether to select a second therapy shell, or whether to complete the therapy, wherein the first therapy shell and the second therapy shell are different in task type.

17. The computer-readable storage device of claim 16, wherein at least one of the first therapy cell or the second therapy cell comprises a training unit and an evaluation unit.

18. The computer-readable storage device of claim 16, wherein the first therapy shell and the second therapy shell is at least one of a phoneme discrimination therapy shell, a rapid word recognition therapy shell, or a word amplification therapy shell.

19. The computer-readable storage device of claim 16, wherein the method further comprises:
gamifying, by the first computer, at least one of the first diagnostic cell, the second diagnostic cell, the first therapy cell, or the second therapy cell, wherein the gamifying is interactive and age based;

rewarding, based at least in part on the gamifying, the patient via a reward system running on the first computer, wherein the patient operates the computing device.

20. The computer-readable storage device of claim 15, wherein the method further comprises a third diagnostic shell, wherein the first diagnostic shell is a phoneme identification diagnostic shell, the second diagnostic shell is a sound-symbol matching diagnostic shell, and the third diagnostic shell is at least one of a syllabification diagnostic shell, a rapid naming diagnostic shell, or a word segmentation diagnostic shell, wherein the third diagnostic shell follows the second diagnostic shell.

\* \* \* \* \*